US012239614B2

(12) United States Patent
Denny et al.

(10) Patent No.: US 12,239,614 B2
(45) Date of Patent: *Mar. 4, 2025

(54) PHARMACOLOGICAL PROPHYLACTICS AGAINST STRESS-INDUCED AFFECTIVE DISORDERS IN FEMALES

(71) Applicants: The Trustees of Columbia University in the City of New York, New York, NY (US); The Research Foundation for Mental Hygiene, Inc., Menands, NY (US)

(72) Inventors: Christine Ann Denny, Ho-Ho-Kus, NJ (US); Briana Kaying Chen, New York, NY (US)

(73) Assignees: THE TRUSTEES OF COLUMBIA UNIVERSITY IN THE CITY OF NEW YORK, New York City, NY (US); THE RESEARCH FOUNDATION FOR MENTAL HYGIENE, INC., Menands, NY (US)

( * ) Notice: Subject to any disclaimer, the term of this patent is extended or adjusted under 35 U.S.C. 154(b) by 179 days.

This patent is subject to a terminal disclaimer.

(21) Appl. No.: 17/954,864

(22) Filed: Sep. 28, 2022

(65) Prior Publication Data

US 2023/0233485 A1     Jul. 27, 2023

Related U.S. Application Data

(63) Continuation of application No. 16/761,338, filed as application No. PCT/US2018/060082 on Nov. 9, 2018, now Pat. No. 11,491,120.

(60) Provisional application No. 62/583,774, filed on Nov. 9, 2017.

(51) Int. Cl.
| | | |
|---|---|---|
| *A61K 31/135* | (2006.01) | |
| *A61P 25/24* | (2006.01) | |
| *A61K 9/00* | (2006.01) | |
| *A61K 45/06* | (2006.01) | |

(52) U.S. Cl.
CPC ............ *A61K 31/135* (2013.01); *A61P 25/24* (2018.01); *A61K 9/0019* (2013.01); *A61K 9/0043* (2013.01); *A61K 9/0053* (2013.01); *A61K 45/06* (2013.01)

(58) Field of Classification Search
CPC .................................................. A61K 31/135
See application file for complete search history.

(56) References Cited

U.S. PATENT DOCUMENTS

| | | | |
|---|---|---|---|
| 3,254,124 A | 5/1966 | Stevens | |
| 6,727,231 B1 | 4/2004 | Page et al. | |
| 8,785,500 B2 | 7/2014 | Charney et al. | |
| 9,801,865 B2 | 10/2017 | Moran | |
| 11,110,070 B2 * | 9/2021 | Brachman | A61P 25/22 |
| 11,491,120 B2 * | 11/2022 | Denny | A61P 43/00 |
| 11,622,948 B2 | 4/2023 | McGowan et al. | |
| 2004/0067963 A1 | 4/2004 | Shapira et al. | |
| 2004/0138298 A1 | 7/2004 | Mermelstein et al. | |
| 2006/0116341 A1 | 6/2006 | Compan | |
| 2009/0105222 A1 | 4/2009 | Kranzler et al. | |
| 2009/0170899 A1 | 7/2009 | Debonnel et al. | |
| 2011/0213219 A1 | 9/2011 | Bilello et al. | |
| 2011/0218213 A1 | 9/2011 | Royster, Jr. | |
| 2013/0236573 A1 | 9/2013 | Singh et al. | |
| 2014/0057988 A1 | 2/2014 | Weg | |
| 2015/0342947 A1 | 12/2015 | Pollard et al. | |
| 2016/0067196 A1 | 3/2016 | Charney et al. | |
| 2016/0313355 A1 | 10/2016 | Aerts et al. | |
| 2017/0007618 A1 | 1/2017 | Goosens et al. | |
| 2017/0049780 A1 | 2/2017 | Wainer et al. | |
| 2018/0325844 A1 | 11/2018 | Brachman et al. | |
| 2019/0046506 A1 | 2/2019 | Friedhoff et al. | |
| 2019/0046554 A1 | 2/2019 | Deisseroth et al. | |
| 2019/0092809 A1 | 3/2019 | Runyon et al. | |

FOREIGN PATENT DOCUMENTS

| | | |
|---|---|---|
| JP | 2012013415 A | 1/2012 |
| WO | 2003020275 A1 | 3/2003 |
| WO | 2008118785 A2 | 10/2008 |
| WO | 2013056229 A1 | 4/2013 |
| WO | 2013149102 A1 | 10/2013 |
| WO | 2014020155 A1 | 2/2014 |
| WO | 2014045023 A1 | 3/2014 |
| WO | 2014169272 A1 | 10/2014 |
| WO | 2014171826 A1 | 10/2014 |
| WO | 2015037248 A1 | 3/2015 |
| WO | 2015121166 A1 | 8/2015 |
| WO | 2016025581 A1 | 2/2016 |
| WO | 2016047677 A1 | 3/2016 |

(Continued)

OTHER PUBLICATIONS

Al-Harbi KS. Treatment-resistant depression: therapeutic trends, challenges, and future directions. Patient Prefer Adherence. 2012; 6:369-88.

Abdallah et al., "Glutamate Metabolism in Major Depressive Disorder", The American Journal of Psychiatry, 171(12), 1320-1327, 2014.

Abdallah et al., "Ketamine and rapid-acting antidepressants: a window into a new neurobiology for mood disorder therapeutics", Annu Rev Med. 2015; 66: pp. 509-523.

Adriana Feder et al: "Efficacy of Intravenous Ketamine for Treatment of Chronic Posttraumatic Stress Disorder a Randomized Clinical Trial", JAMA Psychi, 2014, vol. 71, No. 6, pp. 681-688.

Al Shirawi MI, Kennedy SH, Ho KT, Byrne R, Downar J. Oral Ketamine in Treatment-Resistant Depression: A Clinical Effectiveness Case Series. J Clin Psychopharmacol. 2017; 37(4):464-7.

(Continued)

*Primary Examiner* — Rei Tsang Shiao

(57) ABSTRACT

Methods for prophylactically treating a stress-induced affective disorder or stress-induced psychopathology in a subject are provided. Also provided are methods for inducing and/or enhancing stress resilience in a subject. In certain embodiments, an effective amount of (R,S)-ketamine or (2R,6R)-hydroxynorketamine ((2R,6R)-HNK) is administered to a female or male subject prior to a stressor.

20 Claims, 44 Drawing Sheets

(56) References Cited

FOREIGN PATENT DOCUMENTS

| WO | 2017082103 A1 | 10/2016 |
|---|---|---|
| WO | 2017003935 A1 | 1/2017 |
| WO | 2017087691 A1 | 5/2017 |
| WO | 2018109935 A1 | 6/2018 |
| WO | 2018222781 A2 | 12/2018 |

OTHER PUBLICATIONS

Aleksandrova et al., "Antidepressant effects of ketamine and the roles of AMPA glutamate receptors and other mechanisms beyond NMDA receptor antagonism", J Psychiatry Neurosci 2017; 42(4): 222-229.

Alquraan et al., "Omega-3 Fatty Acids Prevent Post-Traumatic Stress Disorder-Induced Memory Impairment", Biomolecules. Mar. 12, 2019;9(3):100.

Altemus et al., "Sex differences in anxiety and depression clinical perspectives", Front Neuroendocrinol 2014; 35(3): 320-330.

Amat et al., "Previous Ketamine Produces an Enduring Blockade of Neurochemical and Behavioral Effects of Uncontrollable Stress", J Neuro_ 2016; 36(1):153-61.

Author Unknown, "Blood test unlocks new frontier in treating depression", UT Southwestern Medical Center, Mar. 29, 2017, last downloaded from https://www.sciencedaily.com/releases/2017/03/170329145732.htm on Nov. 23, 2021.

Autry AE, Adachi M, Nosyreva E, Na ES, Los MF, Cheng PF, et al. (2011): NMDA receptor blockade at rest triggers rapid behavioural antidepressant responses. Nature 475:91-95.

Averill et al., "Glutamate dysregulation and glutamatergic therapeutics for PTSD: Evidence from human studies", Neurosci Lett. May 10, 2017;649:147-155.

Bach et al., "Blocking human fear memory with the matrix metalloproteinase inhibitor doxycycline", Mol Psychiatry. Jul. 2018;23(7):1584-1589.

Baratta et al., "Stress Enables Reinforcement-Elicited Serotonergic Consolidation of Fear Memory", Biol Psychiatry. May 15, 2016;79(10):814-822.

Bartoli et al., "Metabolic syndrome in people suffering from post-traumatic stress disorder: a systematic review and meta-analysis", Metab Syndr Relat Disord. Oct. 2013;11(5):301-8.

Brachman et al, "Ketamine as a prophylactic against stress-induced depressive-like behavior", Biol Psychiatry. 2016, 79 (9): 776-786.

Brachman et al., "A single injection of ketamine confers robust, long-term protection against stress-induced depressive-like behaviors", Society for Neuroscience conference, Presentation Abstract on Nov. 17, 2014.

Brent Miles as told to Troy Farah, I Used Ketamine to Treat My Depression, Vice, Jan. 15, 2015 [retrieved from https://www.vice.com/en_us/article/4w7eyd/i-used-ketamine-to-treat-my-depression-122].

Browne CA, Lucki I. Antidepressant effects of ketamine: mechanisms underlying fastacting novel antidepressants. Front Pharmacol. 2013; 4.

Caddy C, Giaroli G, White TP, Shergill SS, Tracy DK (2014): Ketamine as the prototype glutamatergic antidepressant: Pharmacodynamic actions, and a systematic review and meta-analysis of efficacy. Ther Adv Psychopharmacol 4:75-99.

Carrier N, Kabbaj M. Sex differences in the antidepressant-like effects of ketamine. Neuropharmacology _ 2013; 170:27-34.

Cattaneo et al., "Absolute Measurements of Macrophage Migration Inhibitory Factor and Interleukin-1-β mRNA Levels Accurately Predict Treatment Response in Depressed Patients", Int J Neuropsychopharmacol. Sep. 30, 2016;19(10).

Chen et al., "Ovarian hormones mediate the prophylactic efficacy of (R,S)-ketamine and (2R,6R)-hydroxynorketamine in female mice", bioRxiv, 712752, Jul. 24, 2019.

Christine Denny, "Analysis of the role of hippocampal adult-born neurons in behavior and physiology", NIH Grant #: 5F31MH084529-03, Budget Start Jul. 1, 2011, Budget End Jun. 30, 2012.

Christine Denny, "Optogenetic dissection of hippocampal circuitry underlying Alzheimers disease", NIH Grant #: 1DP5OD017908-01, Budget StartSep. 19, 2013, Budget End Aug. 31, 2014.

Cieślak et al., "The roles of purinergic signaling in psychiatric disorders", Acta Biochim Pol. 2016;63(1):1-9.

Clinical Trial #: NCT02019654, "An investigation of the biological and neuronal mechanisms of post traumatic stress disorder, depression and post-concussive syndrome onset following a traumatic brain injury", Sponsor: National Institute of Nursing Research, Dec. 20, 2013.

Clinical Trial #: NCT02517190, "Effects of repeated short-term microgravity during parabolic flight conditions on neuro-endocrine, immune and metabolic changes (COSI@PFC)", Sponsor: University Hospital, Caen, Jul. 23, 2015.

Clinicaltrials.gov, Rapid Antidepressant Effects of Ketamine in Major Depression, National Institute of Mental Health (NIMH), Identifier: NCT00088699 [retrieved from https://clinicaltrials.gov/ct2/show/NCT00088699; First Posted: Aug. 2, 2004; Results First Posted: Oct. 12, 2018] [retrieved on Dec. 6, 2018].

Dalla et al., "Females do not Express Learned Helplessness like Males do", Neuropsychopharmacology _ 2007; 33(7): 4559-69.

Daly et al., "Efficacy and Safety of Intranasal Esketamine Adjunctive to Oral Antidepressant Therapy in Treatment Resistant Depression: A Randomized Clinical Trial", JAMA 2018, 75(2): 139-148.

David DJ, Samuels BA, Rainer Q,Wang JW, Marsteller D, Mendez I, et al. (2009): Neurogenesis-dependent and -independent effects of fluoxetine in an animal model of anxiety/depression. Neuron 62:479-493.

Davidson RJ, Pizzagalli D, Nitschke JB, Putnam K. Depression: perspectives from affective neuroscience. Ann Rev Psychology_ 2002; 53:545-74.

De Souza et al., "Posttraumatic stress disorder-type behaviors in streptozotocin-induced diabetic rats can be prevented by prolonged treatment with vitamin E", Behav Brain Res. Feb. 1, 2019;359:749-754.

Denny CA, Burghardt NS, Schachter DM, Hen R, Drew MR (2012): 4- to 6-week-old adult-born hippocampal neurons influence novelty-evoked exploration and contextual fear conditioning. Hippocampus 22:1188-1201.

Denny et al., "Hippocampal Memory Traces Are Differentially Modulated by Experience, Time, and Adult Neurogenesis", Neuron. 2014; 83(1):189-201.

Diazgranados et al., "A randomized add-on trial of an N-methyl-D-aspartate antagonist in treatment-resistant bipolar depression", Arch Gen Psychiatry. Aug. 2010;67(8):793-802.

Dolzani et al., "Inhibition of a Descending Prefrontal Circuit Prevents Ketamine-Induced Stress Resilience in Females", eNeuro 2018; 5(1).

Domino, EF, "Taming the Ketamine Tiger," Anesthesiology, 2010, vol. 113, pp. 678-686.

Donahue RJ, Muschamp JW, Russo SJ, Nestler EJ, Carlezon WA Jr (2014): Effects of striatal deltaFosB overexpression and ketamine on social defeat stress-induced anhedonia in mice. Biol Psychiatry 76:550-558.

Dossat et al., "Behavioral and biochemical sensitivity to low doses of ketamine: influence of estrous cycle in C57BU6 mice", Neuropharmacology 2018; 130: 30-41.

Drew et al., "Arrest of adult hippocampal neurogenesis in mice impairs single- but not multiple-trial contextual fear conditioning", Behav Neurosci. 2010; 124(4):446-54.

Dulawa SC, Holick KA, Gundersen B, Hen R (2004): Effects of chronic fluoxetine in animal models of anxiety and depression. Neuropsychopharmacology 29:1321-1330.

Dunlop et al., "The hypothalamic-pituitary-adrenal axis in PTSD: Pathophysiology and treatment interventions", Prog Neuropsychopharmacol Biol Psychiatry. Mar. 8, 2019;89:361-379.

E.D. Ballard et al., Improvement in suicidal ideation after ketamine infusion: Relationship to reductions in depression and anxiety, J. Psychiatry Research vol. 58 pp. 161-166 Nov. 2014.

Elhabazi et al., "Assessment of morphine-induced hyperalgesia and analgesic tolerance in mice using thermal and mechanical nociceptive modalities", J Vis Exp. Jul. 29, 2014;(89).

(56) References Cited

OTHER PUBLICATIONS

Flory JD, Yehuda R. Comorbidity between post-traumatic stress disorder and major depressive disorder: alternative explanations and treatment considerations. Dialogues Clin Neurosci. 2015; 17(2):141-50.
Franceschelli et al.: "Sex differences in the rapid and the sustained antidepressant-like effects of ketamine in stress-naïve and "depressed" mice exposed to chronic mild stress", Neuroscience. Apr. 2, 2015;290:49-60.
Fukumoto et al., "Antidepressant Potential of (R)-Ketamine in Rodent Models: Comparison with (S)-Ketamine", J Pharmacol Exp Ther. Apr. 2017;361(1):9-16.
Gardier et al., "Ketamine as a prophylactic against stress-induced depressive-like behavior", Biol Psychiatry, vol. 79 (9), p. 776-86, May 2016.
Zarate et al. A randomized trial of an N-methyl-D-aspartate antagonist in treatment-resistant major depression. Arch Gen Psychiatry_ 2006; 63(8):856-64.
Zarate et al., "Relationship of ketamine's plasma metabolites with response, diagnosis, and side effects in major depression", Biol Psychiatry_ 2012; 72(4):331-8.
Zarate et al., "Replication of ketamine's antidepressant efficacy in bipolar depression: a randomized controlled add-on trial", Biol Psychiatry. 2012; 71 (11):939-46.
Zhang et al., "R (-)-ketamine shows greater potency and longer lasting antidepressant effects than S +)-ketamine", Pharmacol Biochem Behav_ 2014; 116:137-41.
Zheng et al., "Identification and validation of urinary metabolite biomarkers for major depressive disorder", Mol Cell Proteomics. Jan. 2013;12(1):207-14.
Faye et al., "Rapid anxiolytic effects of a serotonin type 4 receptor agonist involve prefrontal cortex/brainstem neural circuit recruitment", European Neuropsychopharmacology, vol. 28, Supplement 1, 2018, pp. S21-S22.
Official Action issued in CN Pat. App. No. 2020800422524 dated Aug. 8, 2023.
Hammack SE, Cooper MA, Lezak KR (2012): Overlapping neurobiology of learned helplessness and conditioned defeat: Implications for PTSD and mood disorders. Neuropharmacology 62:565-575.
Hasler et al., "Reduced Prefrontal Glutamate/Glutamine and γ-Aminobutyric Acid Levels in Major Depression Determined Using Proton Magnetic Resonance Spectroscopy", Arch Gen Psychiatry. Feb. 2007;64(2):193-200.
Honack et al., "Sex differences in NMDA receptor mediated responses in rats", Brain Res 1993; 620(1): 167-170.
Howlett et al., "Prevention of Trauma and Stressor-Related Disorders: A Review. Neuropsychopharmacology", Jan. 2016;41(1):357-69.
Huang et al., "New Treatment Strategies of Depression: Based on Mechanisms Related to Neuroplasticity", Neural Plast. 2017.
International Search Report and Written Opinion dated Feb. 3, 2017 corresponding to International Patent Application No. PCT/US16/62562, 16 pages.
International Search Report and Written Opinion of corresponding International Application PCT/US2018/059834, mailed on Feb. 25, 2019.
International Search Report and Written Opinion of corresponding International Application PCT/US2018/060082, mailed on Jan. 24, 2019.
Ionescu et al., "A single infusion of ketamine improves depression scores in patients with anxious bipolar depression", Bipolar Disord. Jun. 2015;17(4):438-43.
J Craig Nelson, "The evolving story of folate in depression and the therapeutic potential of I-methylfolate", Am J Psychiatry. Dec. 2012;169(12):1223-5.
Janice B. Schwartz, "The influence of sex on pharmacokinetics", Clin Pharmacokinet 2003; 42(2): 107-121.
Jha et al., "Can C-reactive protein inform antidepressant medication selection in depressed outpatients? Findings from the CO-MED trial", Psychoneuroendocrinology, vol. 78, Apr. 2017, pp. 105-113.

Jinnah et al., "Metabolic disorders of purine metabolism affecting the nervous system", Handb Clin Neurol. 2013;113:1827-36.
Johnson et al., "Metabolomics: beyond biomarkers and towards mechanisms", Nat Rev Mol Cell Biol 17, 451-459 (2016).
Joo et al., "Chronic immobilization stress induces anxiety- and depression-like behaviors and decreases transthyretin in the mouse cortex", Neurosci Lett. 2009; 461(2):121-5.
Kaddurah-Daouk et al., "Pretreatment metabotype as a predictor of response to sertraline or placebo in depressed outpatients: a proof of concept", Transl Psychiatry. 2011;1(7).
Kearns et al., "Early interventions for PTSD: a review", Depress Anxiety. Oct. 2012;29(10):833-42.
Kessler et al., "Posttraumatic stress disorder in the National Comorbidity Survey", Arch Gen Psychiatry. Dec. 1995;52(12):1048-60.
Kessler RC, Berglund P, Demler 0, Jin R, Merikangas KR, Walters EE. Lifetime prevalence and age-of-onset distributions of DSM-IV disorders in the National Comorbidity Survey Replication. Arch Gen Psychiatry. 2005; 62(6): p. 93-602.
Khalid, "Treatment-resistant depression; therapeutic trends, challenges and future directions", Patient Prefer Adherence, p. 369-388, May 6, 2012.
Knoll et al., "Anxiolytic-Like Effects of k-Opioid Receptor Antagonists in Models of Unlearned and Learned Fear in Rats", J Pharmacol Exp Ther. Dec. 2007;323(3):838-45.
Kokras et al., "Sex differences in animal models of psychiatric disorders", Br J Pharmacol 2014; 171 (20): 4595-4619.
Kornstein SG, Schatzberg AF, Thase ME, Yonkers KA, McCullough JP, Keitner GI, et al. Gender differences in treatment response to sertraline versus imipramine in chronic depression. Am J Psychiatry_ 2000; 157(9): 1445-52.
Lagamma et al., "Antidepressant but Not Prophylactic Ketamine Administration Alters Calretinin and Calbindin Expression in the Ventral Hippocampus", Front Mol Neurosci. Nov. 6, 2018;11:404.
Maier SF, Seligman MEP (1976): Learned helplessness: Theory and evidence. J Exp Psychol 105:3-46.
Martinac et al., "Metabolic syndrome, activity of the hypothalamic-pituitary-adrenal axis and inflammatory mediators in depressive disorder", Acta Clin Croat. Mar. 2014;53(1):55-71.
Mastrodonato et al., "Ventral CA3 Activation Mediates Prophylactic Ketamine Efficacy Against Stress-Induced Depressive-like Behavior", Biol Psychiaty. 2018; 84(11): 846-856.
Mathew et al.: "Riluzole for relapse prevention following intravenous ketamine in treatment-resistant depression: a pilot randomized, placebo-controlled continuation trial", International Journal of Neuropsychopharmacology, vol. 13 / Issue 1. pp. 71-82, 2010.
Matt McMillen, Ketamine: The Future of Depression Treatment? WedMD.com, Depression Health Center, Sep. 23, 2014 [retrieved from https://www.webmd.com/depression/news/20140923/ketamine-depression#1].
McGhee LL, Maani CV, Garza TH, DeSocio PA, Gaylord KM, Black IH (2009): The effect of propranolol on posttraumatic stress disorder in burned service members. J Burn Care Res 30:92-97.
McGowan et al., "Prophylactic ketamine alters nucleotide and neurotransmitter metabolism in brain and plasma following stress", Neuropsychopharmacology 2018; 43 (9): 1813-1821.
McGowan JC, LaGamma CT, Lim SC, Tsitsiklis M, Neria Y, Brachman RA, et al. Prophylactic Ketamine Attenuates Learned Fear. Neuropsychopharmacology_ 2017; 42(8): 1577-89.
McNulty et al., "Compounded oral ketamine for severe depression, anxiety, and pain in a hospice patient with end-stage chronic obstructive pulmonary disease, cardiopulmonary failure, and severe renal insufficiency: a case report", International Journal of Pharmaceutical Compounding, 2012, 16(5), 364-368.
Mendez-David et al., "Rapid anxiolytic effects of a 5-HT(4) receptor agonist are mediated by a neurogenesis-independent mechanism", Neuropsychopharmacology 39 (6): 1366-1378; 2014.
Meyerhoff et al., "Cortical gamma-aminobutyric acid and glutamate in posttraumatic stress disorder and their relationships to self-reported sleep quality", Sleep. May 1, 2014;37(5):893-900.
Micheli et al., "Neurological disorders of purine and pyrimidine metabolism", Curr Top Med Chem. 2011;11(8):923-47.

(56) References Cited

OTHER PUBLICATIONS

Miller et al., "Personalized medicine in major depressive disorder—opportunities and pitfalls." Metabolism: clinical and experimental vol. 62 Suppl 1,0 1 (2013): S34-9.

Mion et al., "Ketamine Pharmacology: An Update (Pharmacodynamics and Molecular Aspects, Recent Findings)", CNS Neurosci Ther. 2013; 19(6):370-80.

Muller JM, Morelli E, Ansorge M, Gingrich JA (2011): Serotonin transporter deficient mice are vulnerable to escape deficits following inescapable shocks. Genes Brain Behav 10:166-175.

Murrough et al, "Antidepressant Efficacy of Ketamine in Treatment-Resistant Major Depression: A two-site randomized controlled trial", Am. J. Psychiatry, 2013, vol. 170, Issue 10, pp. 1134-1142.

Murrough et al., "Ketamine for rapid reduction of suicidal ideation: a randomized controlled trial", Psychol Med. Dec. 2015;45(16):3571-80.

Murrough et al.: "Rapid and longer-term antidepressant effects of repeated ketamine infusions in treatment-resistant major depression": Biological Psychiatry, vol. 74 / Issue 4, pp. 250-6, 2013.

National Research Council. "Depression in parents, parenting, and children: Opportunities to improve identification, treatment, and prevention." (2009).

Nikiforuk Agnieszka et al: "Ketamine prevents stress-induced cognitive inflexibility in rats", Psychoneuroendocrinology, 2013, vol. 40, pp. 119-122.

Palomero-Gallagher et al., "AMPA, kainate, and NMDA receptor densities in the hippocampus of untreated male rats and females in estrus and diestrus", J Comp Neurol 2003; 459(4): 468-474.

Pan et al., "GTP-cyclohydrolase deficiency responsive to sapropterin and 5-HTP supplementation: relief of treatment-refractory depression and suicidal behaviour", BMJ Case Rep. Jun. 9, 2011, 2011.

Pan et al., "Neurometabolic Disorders: Potentially Treatable Abnormalities in Patients With Treatment Refractory Depression and Suicidal Behavior", The American journal of psychiatry 174(1), 42-50.

Pan et al., "Neuropsychiatric Symptoms in Inborn Errors of Metabolism: Incorporation of Genomic and Metabolomic Analysis into Therapeutics and Prevention", Current genetic medicine reports 1(1), 65-70.

Pan et al., "Effects of Ketamine on Metabolomics of Serum and Urine in Cynomolgus Macaques (*Macaca fascicularis*)." Journal of the American Association for Laboratory Animal Science : JAALAS vol. 55,5 (2016): 558-64.

Papakostas et al., "L-methylfolate as adjunctive therapy for SSRI-resistant major depression: results of two randomized, double-blind, parallel-sequential trials", Am J Psychiatry. Dec. 2012;169(12):1267-74.

Parise Eric M et al: "Repeated Ketamine Exposure Induces an Enduring Resilient Phenotype in Adolescent and Adult Rats", Biological Psychiatry, 2013, vol. 74, No. 10, pp. 750-759.

Park et al., "Purine and pyrimidine metabolism: Convergent evidence on chronic antidepressant treatment response in mice and humans", Sci Rep. Oct. 12, 2016;6:35317.

Paul et al., "(R,S)-Ketamine metabolites (R,S)-norketamine and (28,6S)-hydroxynorketamine increase the mammalian target of rapamycin function", Anesthesiology_ 2014; 121(1): pp. 149-159.

Pehrson et al., "Altered γ-aminobutyric acid neurotransmission in major depressive disorder: a critical review of the supporting evidence and the influence of serotonergic antidepressants", Drug Des Devel Ther. Jan. 19, 2015;9:603-24.

Peselow et al., "Prophylactic efficacy of fluoxetine, escitalopram, sertraline, paroxetine, and concomitant psychotherapy in major depressive disorder: outcome after long-term follow-up". Psychiatry Res. Feb. 28, 2015;225(3):680-6.

Pham et al., "Common Neurotransmission Recruited in (R,S)-Ketamine and (2R,6R)-Hydroxynorketamine-Induced Sustained Antidepressant-like Effects", Biol Psychiatry 2018; 84 (1): e3-e6.

Piccinelli et al., "Gender differences in depression. Critical review", Br J Psychiatry. 2000; 177: pp. 486-492.

Pittig et al., "The role of associative fear and avoidance learning in anxiety disorders: Gaps and directions for future research", Neurosci Biobehav Rev. May 2018;88:117-140.

Porsolt et al., "Depression: a new animal model sensitive to antidepressant treatments", Nature 1977; 266(5604): 730-732.

Price et al. "Effects of intravenous ketamine on explicit and implicit measures of suicidality in treatment-resistant depression." Biological psychiatry vol. 66,5 (2009): 522-6.

Rachel Yarmolinsky, Could a Dose of Ketamine Prevent Psychiatric Disorders Such as PTSD?, Columbia University Department of Psychiatry, Jul. 2, 2015 [retrieved from https://www.columbiapsychiatry.org/news/could-dose-ketamine-prevent-psychiatric-disorders-such-ptsd].

Ramaekers et al., "Clinical recognition and aspects of the cerebral folate deficiency syndromes", Clin Chem Lab Med. Mar. 1, 2013;51(3):497-511.

Ramirez et al., "Activating positive memory engrams suppresses depression-like behaviour", Nature 522, 335-339 (2015).

Rasmussen et al., "Serial infusions of low-dose ketamine for major depression", J Psychopharmacol. 2013; 27(5):444-50.

Reardon, Rave drug holds promise for treating depression fast, Nature, 517, 130-131 (2015).

Redei et al., "Blood transcriptomic biomarkers in adult primary care patients with major depressive disorder undergoing cognitive behavioral therapy", Transl Psychiatry. Sep. 16, 2014;4(9).

Richardson-Jones JW, Craige CP, Guiard BP, Stephen A, Metzger KL, Kung HF, et al. (2010): 5-HT1A Autoreceptor Levels Determine Vulnerability to Stress and Response to Antidepressants. Neuron 65(1): 40-52.

Rissman et al., "Estrogen receptors are essential for female sexual receptivity", Endocrinology_ 1997; vol. 138 (1):507-10.

Rotroff et al., "Metabolomic signatures of drug response phenotypes for ketamine and esketamine in subjects with refractory major depressive disorder: New mechanistic insights for rapid acting antidepressants", Sep. 2016, Translational Psychiatry 6(9):e894.

Saland et al., "Hedonic sensitivity to low-dose ketamine is modulated by gonadal hormones in a ?ex-dependent manner", Sci Rep_ 2016; 6.

Saxe et al., "Ablation of hippocampal neurogenesis mpairs contextual fear conditioning and synaptic plasticity in the dentate gyrus", Proc Natl Acad Sci 2006; 103( 46): H501-17506.

Schiller D, Monfils MH, Raio CM, Johnson DC, LeDoux JE, Phelps EA (2010): Preventing the return of fear in humans using reconsolidation update mechanisms. Nature 463:49-53.

Serafini G, Howland RH, Rovedi F, Girardi P, Amore M. The Role of Ketamine in Treatment-Resistant Depression: A Systematic Review. Curr Neuropharmacol. 2014; 12(5):444-61.

Serchov et al., "Increased Signaling via Adenosine A1 Receptors, Sleep Deprivation, Imipramine, and Ketamine Inhibit Depressive-like Behavior via Induction of Homer1a", Neuron. Aug. 5, 2015;87(3):549-62.

Shansky et al., "Estrogen promotes stress sensitivity in a prefrontal cortex-amygdala pathway", Cerebral cortex (New York, NY: 1991) 2010; 20(11): 2560-2567.

Shin et al., "The neurocircuitry of fear, stress, and anxiety disorders", Neuropsychopharmacology. Jan. 2010;35(1):169-91.

Shirayama et al., "R-ketamine: a rapid-onset and sustained antidepressant without psychotomimetic side effects", Transl Psychiatry. Sep. 1, 2015;5(9):e632.

Singh et al., "Intravenous Esketamine in Adult Treatment-Resistant Depression: A Double-Blind, DoubleRandomization, Placebo-Controlled Study", Biol Psychiatly 2016; 80(6): 424-431.

Soldin et al., "Sex differences in pharmacokinetics and pharmacodynamics", Clin Pharmacokinet 2009; 48 (3): 143-157.

Soumier et al., "New Hippocampal Neurons Mature Rapidly in Response to Ketamine But Are Not Required for Its Acute Antidepressant Effects on Neophagia in Rats", eNeuro_ 2016; 3(2).

Strom et al., "Ovariectomy and 17β-estradiol Replacement in Rats and Mice: A Visual Demonstration", Journal of Visualized Experiments, 2012 (64):e4013.

Sugiyama et al., "Systemic administration of a delta opioid receptor agonist, KNT-127, facilitates extinction learning of fear memory in rats", J Pharmacol Sci. Mar. 2019;139(3):174-179.

(56) References Cited

OTHER PUBLICATIONS

Supplementary European Search Report in corresponding European Application EP 16867149.3, dated Nov. 6, 2019.
Suzuki, K., Nosyreva, E., Hunt, K et al. Effects of a ketamine metabolite on synaptic NMDAR function. Nature 546, E1-E3 (2017).
Tabak et al., "Interaction of CD38 Variant and Chronic Interpersonal Stress Prospectively Predicts Social Anxiety and Depression Symptoms Over Six Years", Clin Psychol Sci. Jan. 1, 2016;4(1):17-27.
Thelen et al., "Repeated ketamine treatment induces sex-specific behavioral ?nd neurochemical effects in mice", Behav Brain Res_ 2016; 312:305-12.
Trouch S, Sasaki JM, Tu T, Reijmers LG (2013): Fear extinction causes target-specific remodeling of perisomatic inhibitory synapses. Neuron 80:1054-1065.
Unknown, "Blood test unlocks new frontier in treating depression", Science Daily, Mar. 29, 2017.
Van't Veer et al., "Role of kappa-opioid receptors in stress and anxiety-related behavior." Psychopharmacology vol. 229,3 (2013): 435-52.
Watanabe et al., "Gene expression-based biological test for major depressive disorder: an advanced study", Neuropsychiatr Dis Treat. Feb. 21, 2017;13:535-541.
Waxman et al., "Sex differences in the expression of hepatic drug metabolizing enzymes", Mol Pharmacol 2009; 76(2): 215-228.
Weckmann et al., "Time-dependent metabolomic profiling of Ketamine drug action reveals hippocampal pathway alterations and biomarker candidates", Transl Psychiatry. Nov. 11, 2014;4(11).
WHO. Depression Fact Sheet. World Health Organization. 2017.
Womble, AL, "Effects of Ketamine on Major Depressive Disorder in a Patient with Posttraumatic Stress Disorder," AANA Journal, Apr. 2013, vol. 81, No. 2, pp. 118-119.
Wood et al., "Acute toxicity associated with the recreational use of the ketamine derivative methoxetamine", European Journal of Clinical Pharmacology, 68(5), 853-856, 2012.
World Health Organization. List of Essential Medicines. Adults: 19th Edition. Apr. 2015.
Yamaguchi et al., "(2R,6R)-Hydroxynorketamine is not essential for the antidepressant actions of (R)-ketamine in mice", Neuropsychopharmacology, 2018.
Yang et al. "Potential metabolite markers of schizophrenia." Molecular psychiatry vol. 18,1 (2013): 67-78. doi:10.1038/mp.2011.131.
Zanos et al., "NMDAR inhibition-independent antidepressant actions of ketamine metabolites", Nature_ 2016; 533(7604):481-6.
Zarate et al, Ketamine for depression: evidence, challenges and promise, World Psychiatry. 2015;14(3):348-50.
EP Communication pursuant to Article 94(3) EPC dated Mar. 14, 2024 issued in EP Pat. Appln. No. 20786878.7.
Official Action issued in CN Pat. App. No. 2020800422524 dated Feb. 29, 2024.
Official Action issued in JP Pat. Appln. No. 2021-560628 dated Mar. 5, 2024.
Highland et al., "Group II metabotropic glutamate receptor blockade promotes stress resilience in mice", Neuropsychopharmacology. Sep. 2019;44(10):1788-1796.
Lucas et al., "Serotonin (4) (5-HT(4) receptor agonists are putative antidepressants with a rapid onset of action", Neuron, vol. 55, Issue 5, p. 712-725, Sep. 2007.
Examination Report issued in AU Pat. Appln. No. 2020271839 dated Oct. 30, 2024.

* cited by examiner

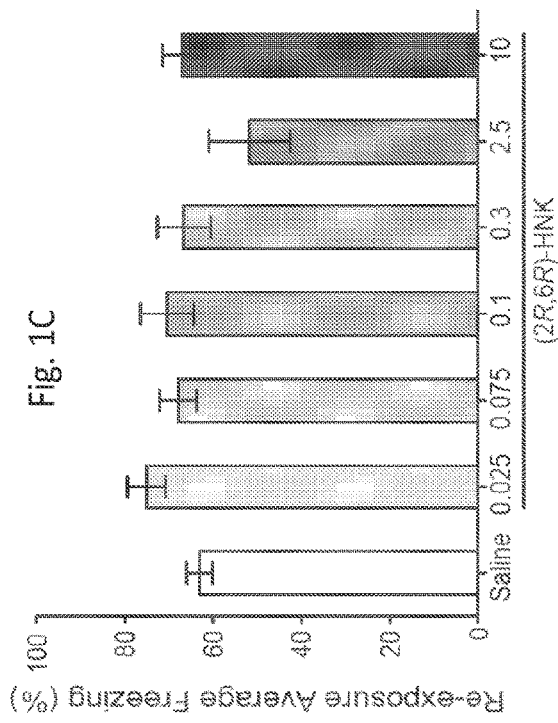
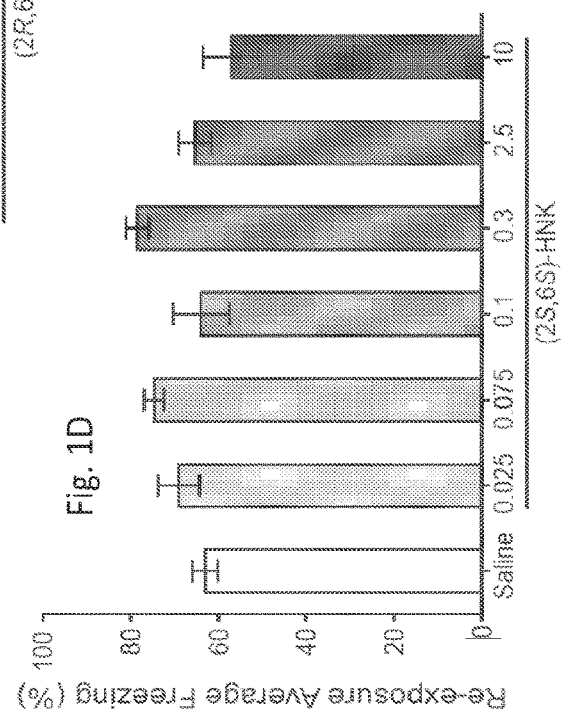
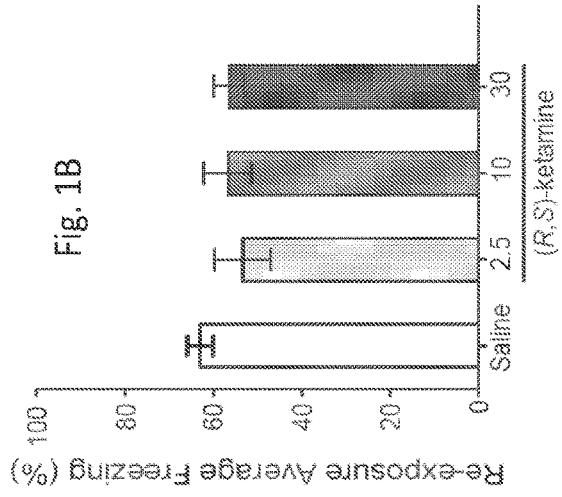

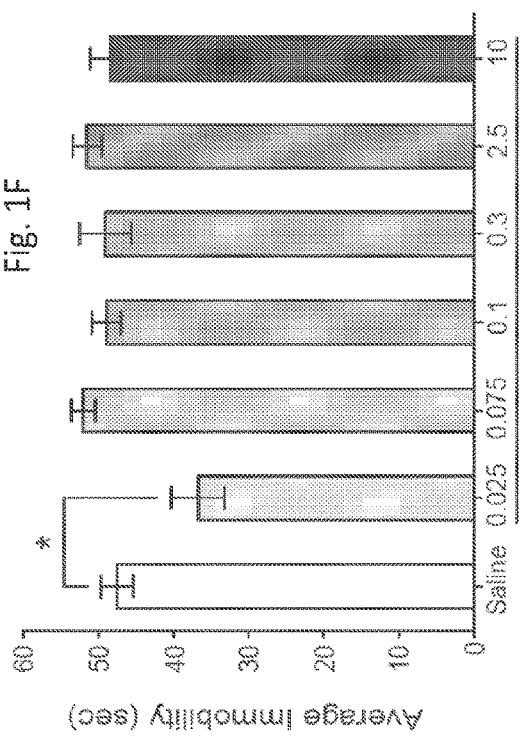
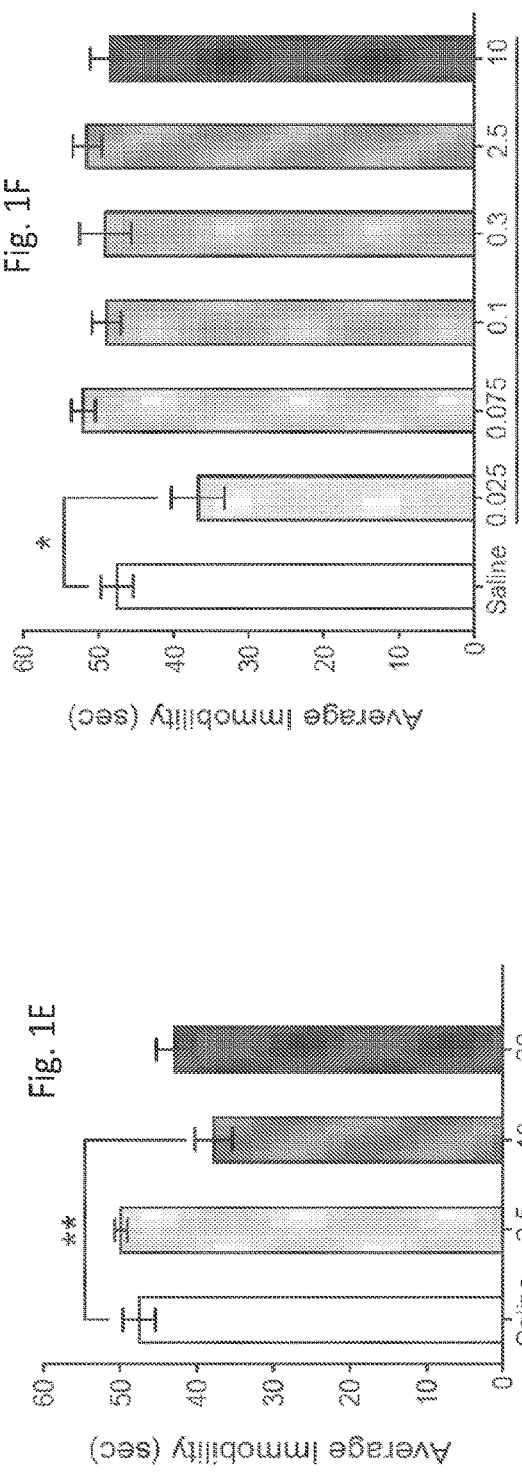
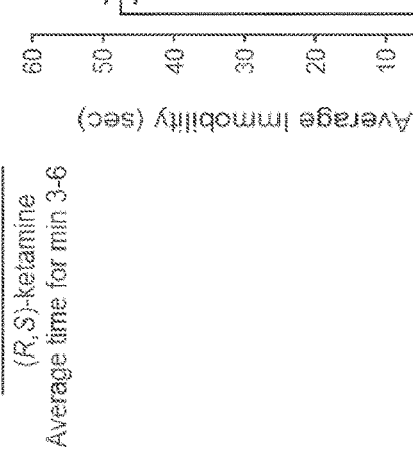

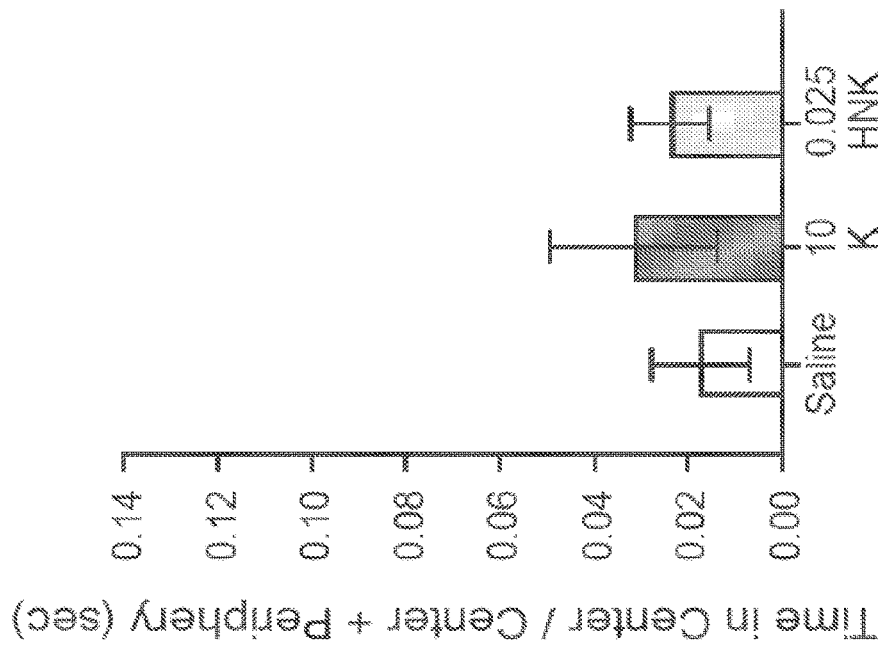
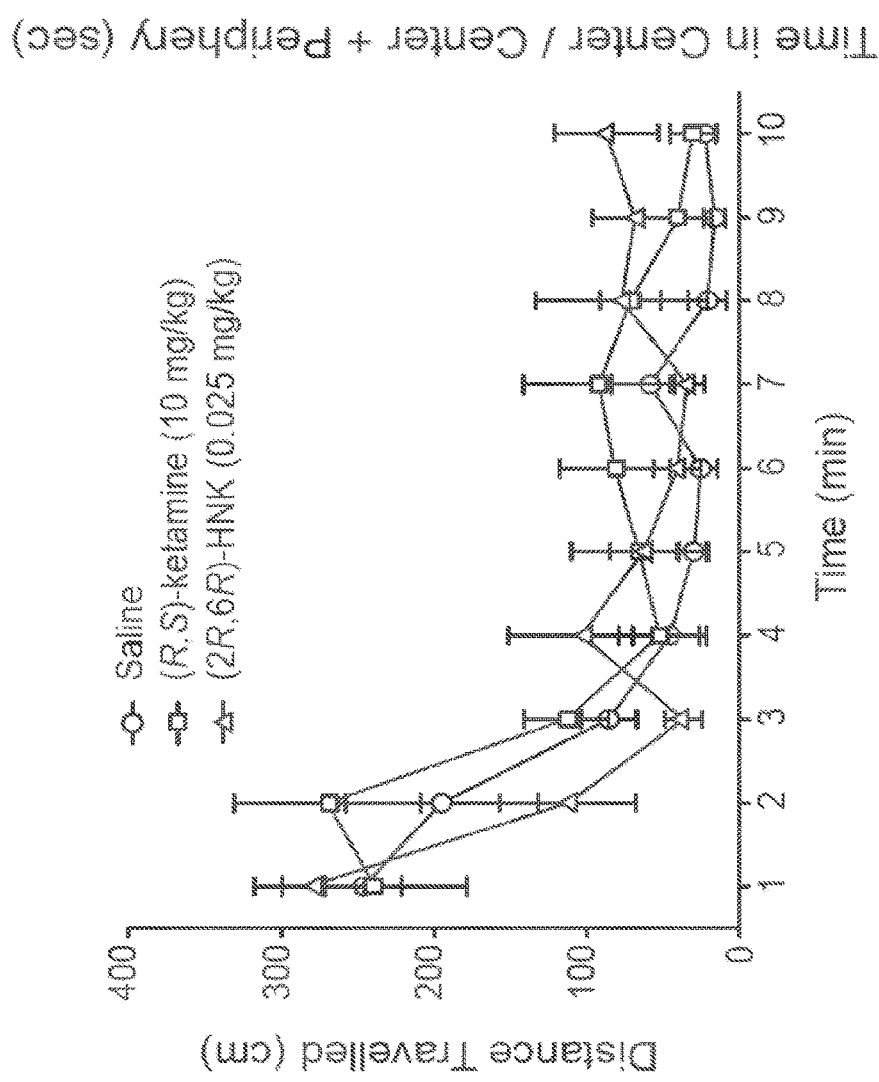
Fig. 1H
Fig. 1I

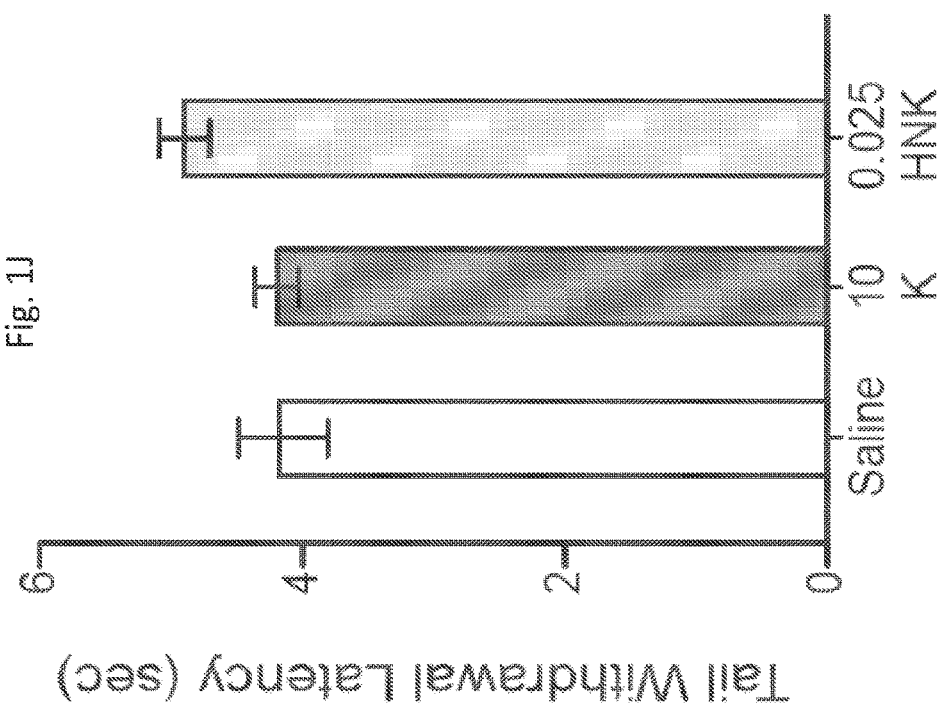

Forced Swim Test

Forced Swim Test

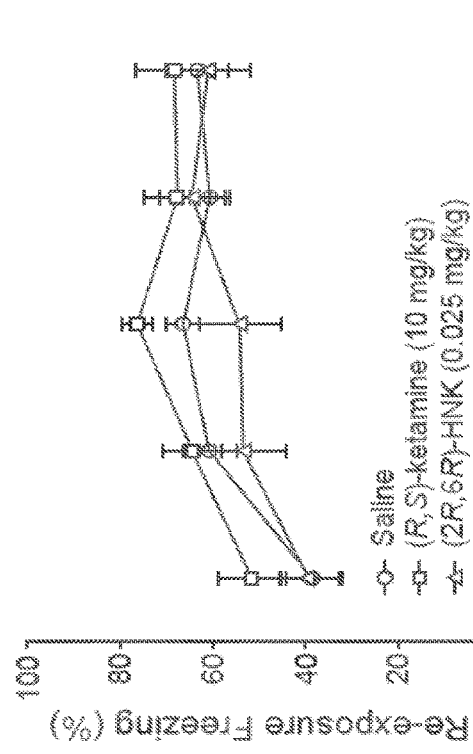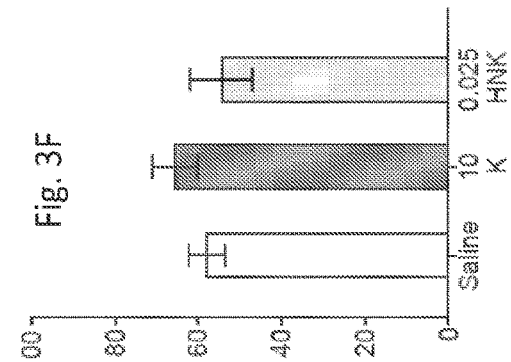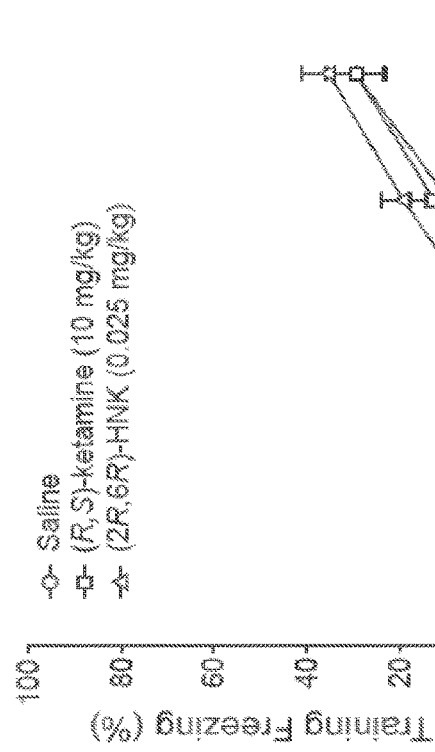

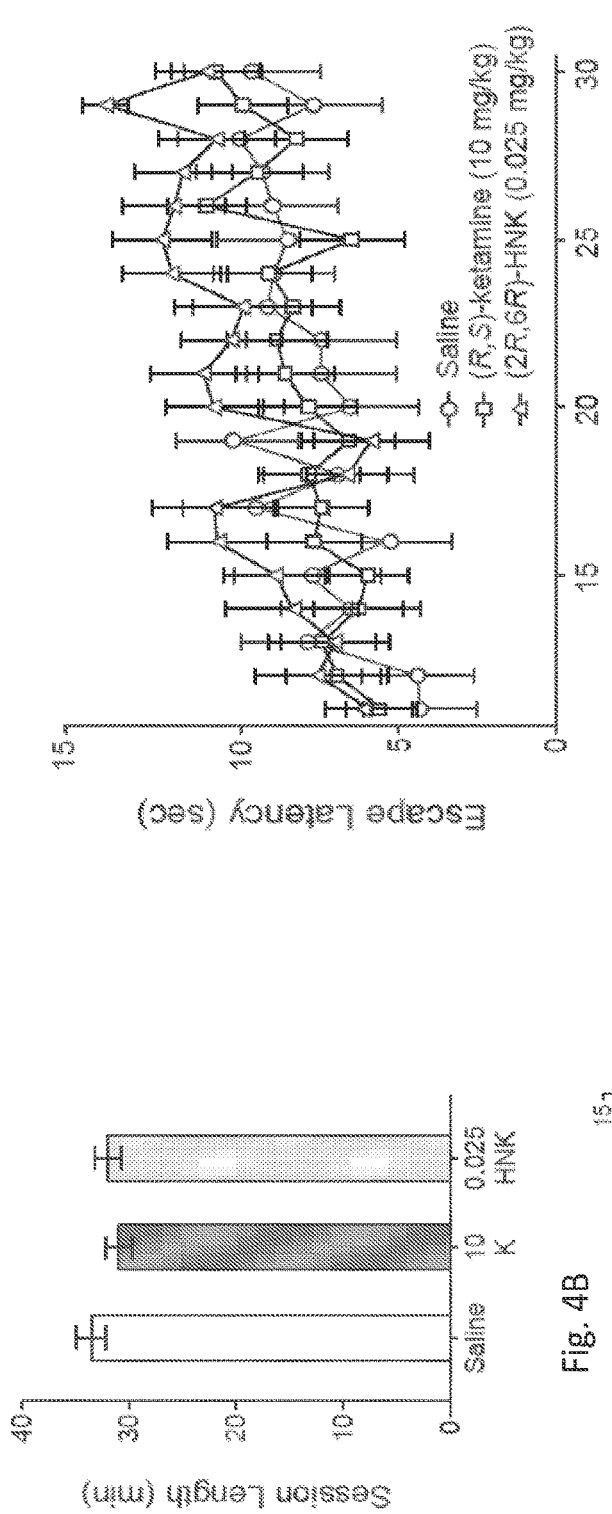

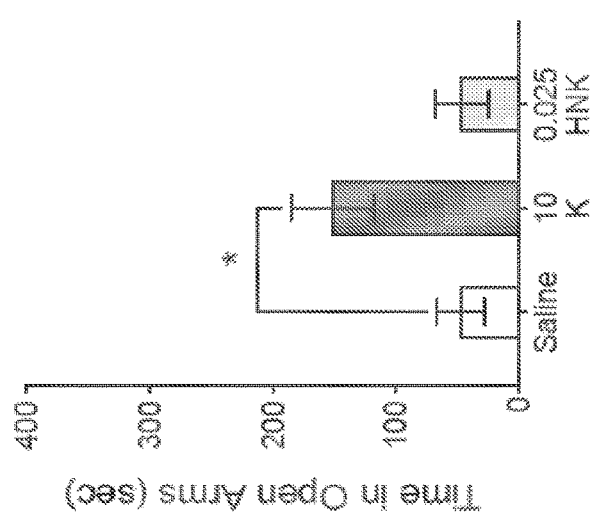
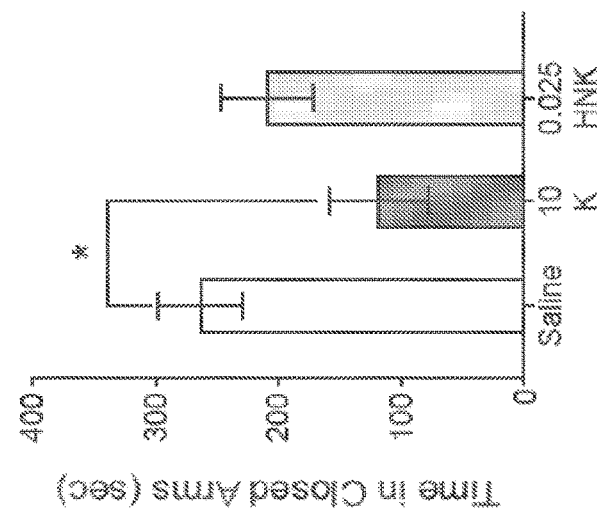
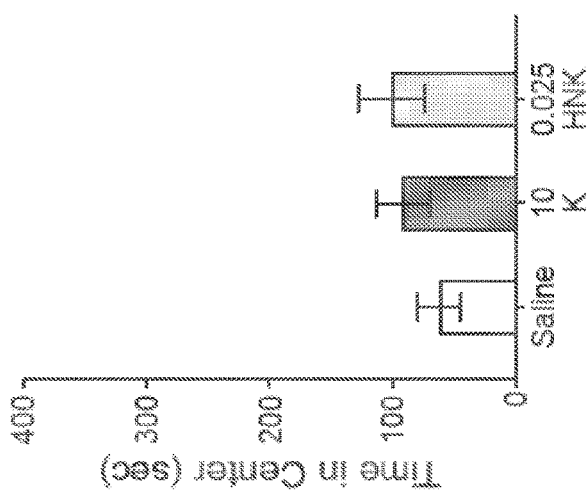
Elevated Plus Maze
Fig. 4G
Fig. 4H
Fig. 4I

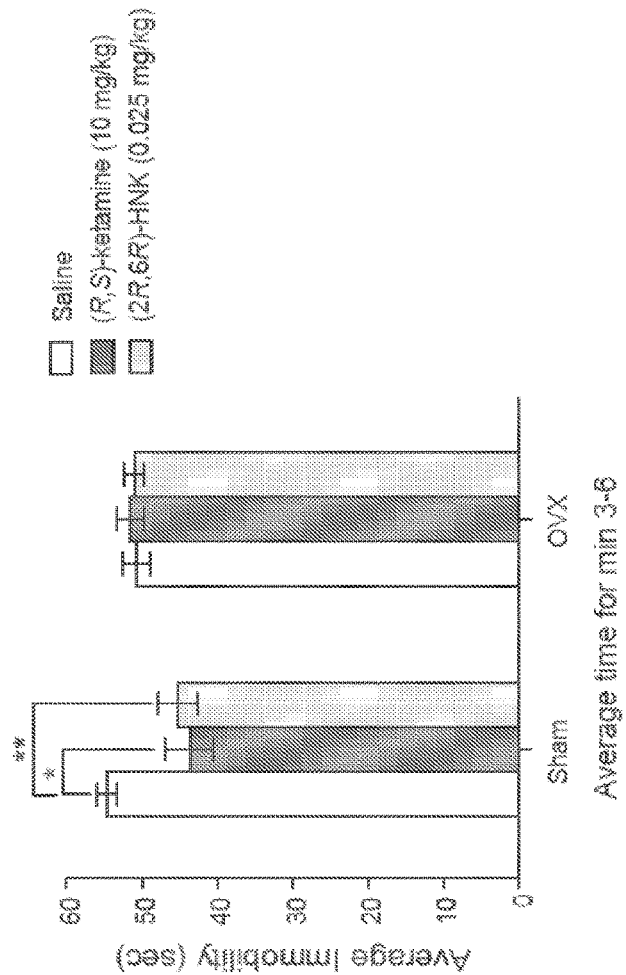
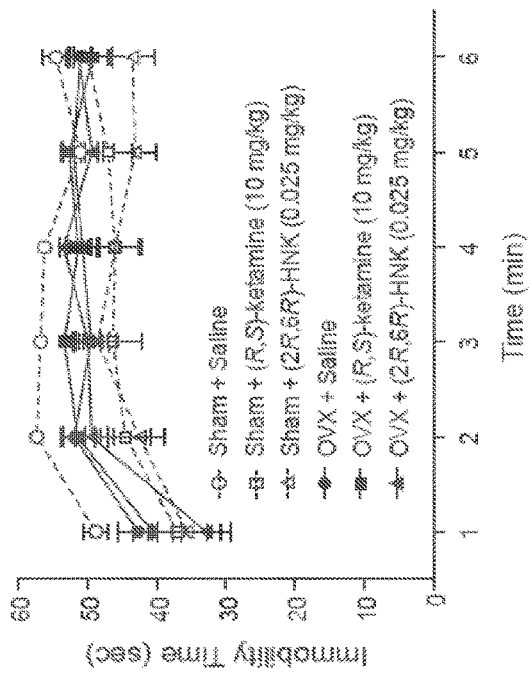
Fig. 5B
Fig. 5C

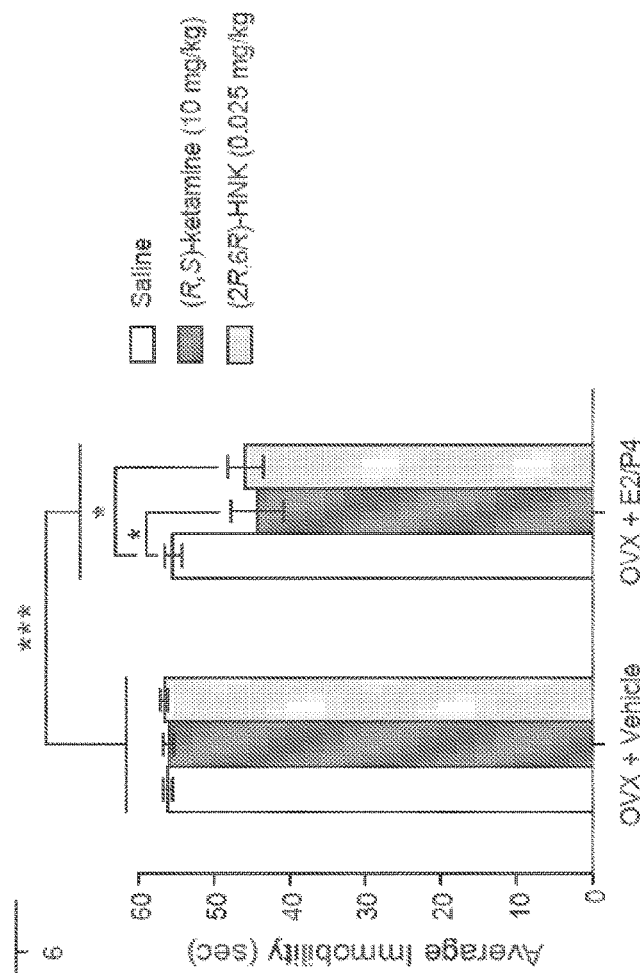
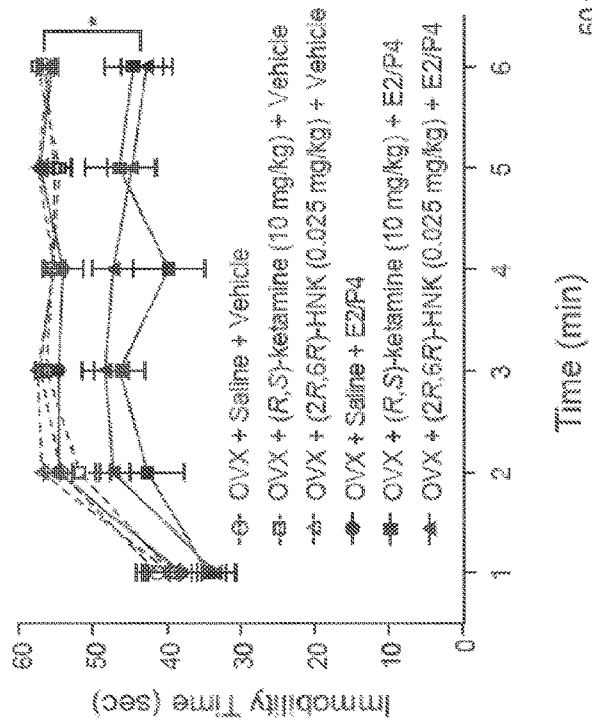
Fig. 5E
Fig. 5F

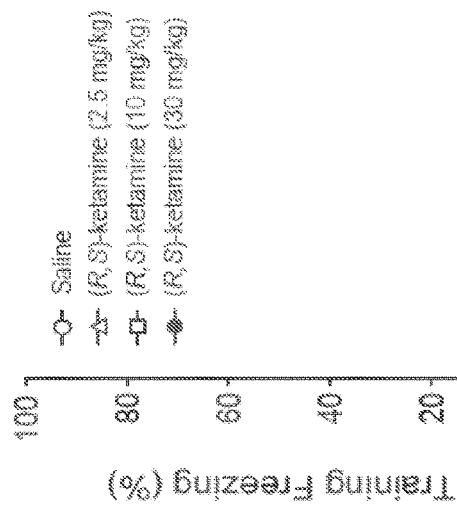
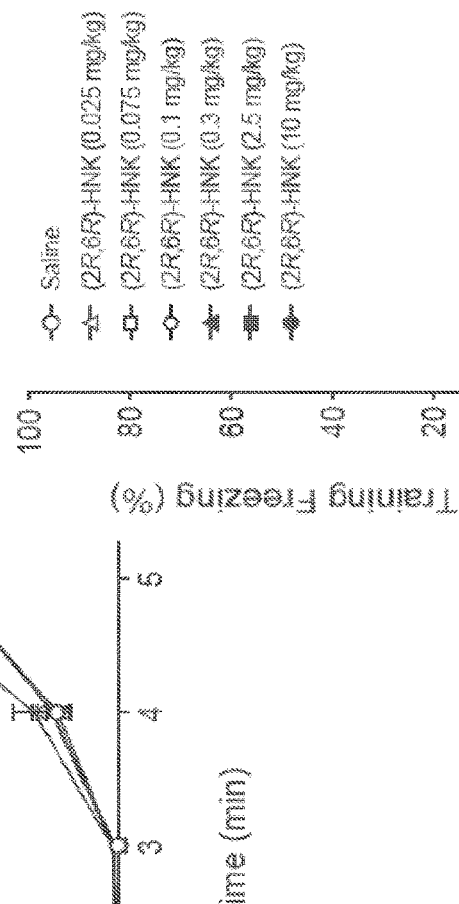
Fig. 6A
Fig. 6B
Contextual Fear Conditioning

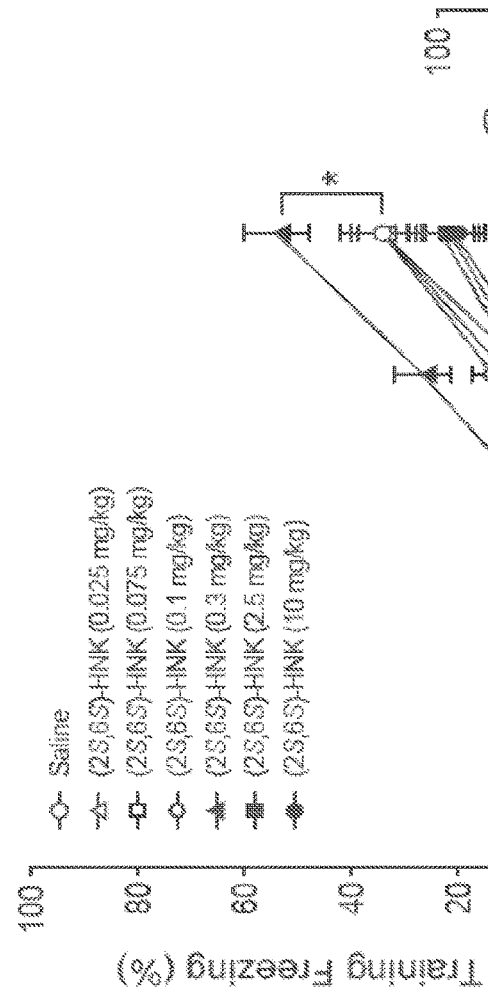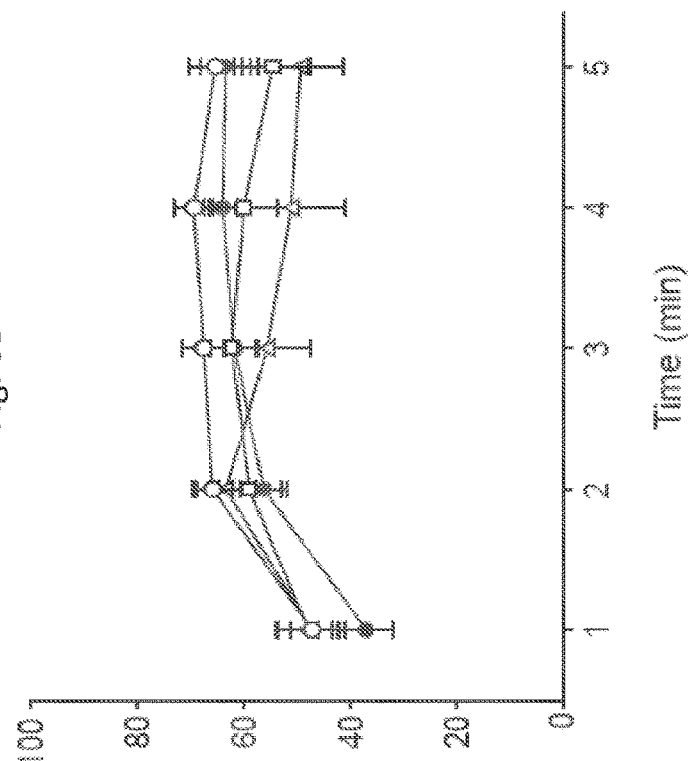
Fig. 6C
Fig. 6D

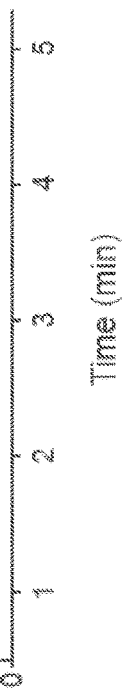
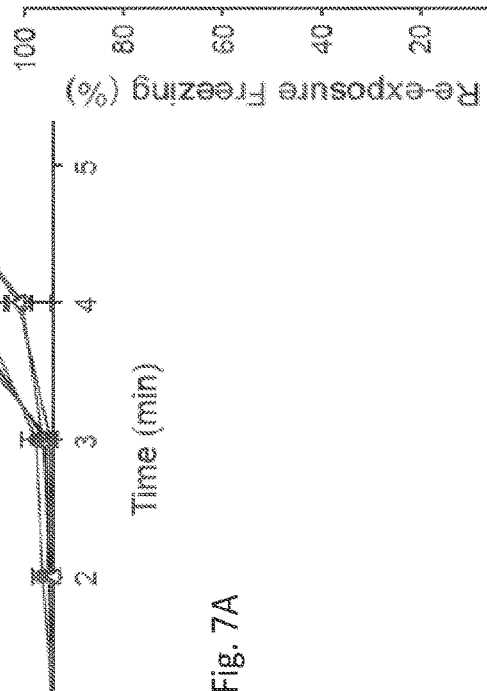
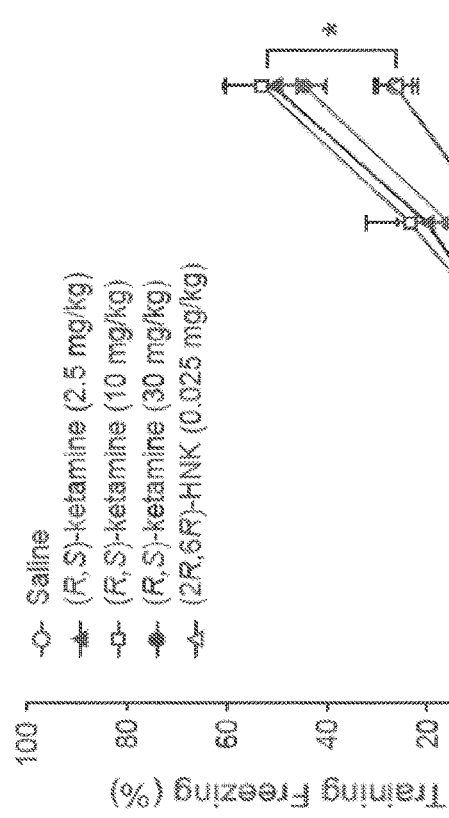
Fig. 7A
Fig. 7B

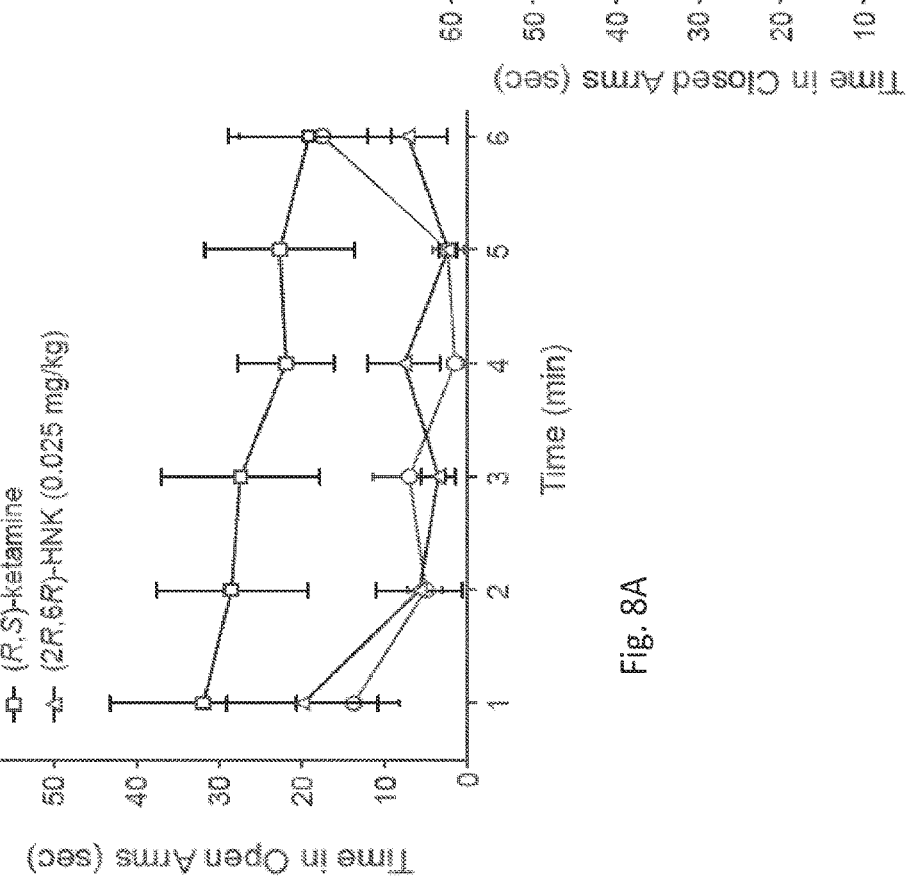

Elevated Plus Maze

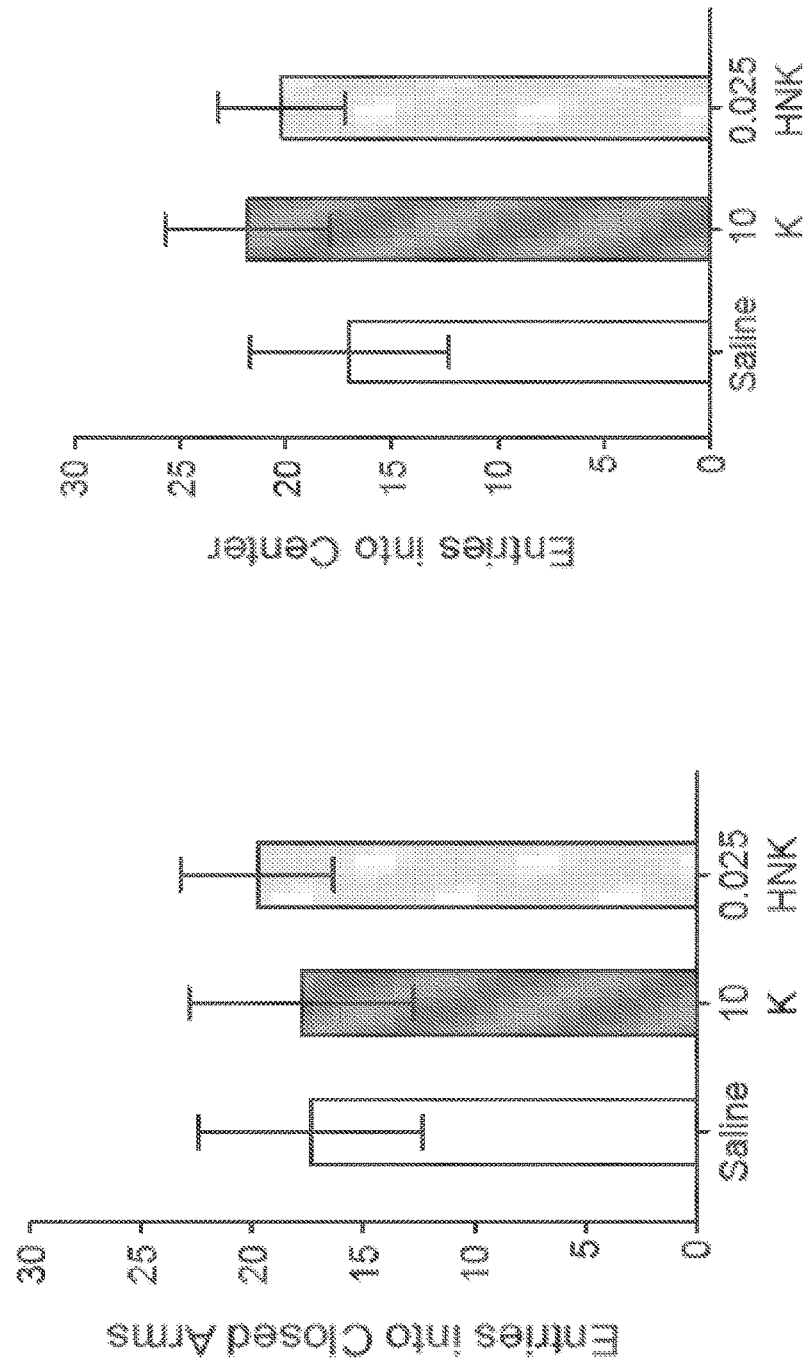

Contextual Fear Conditioning

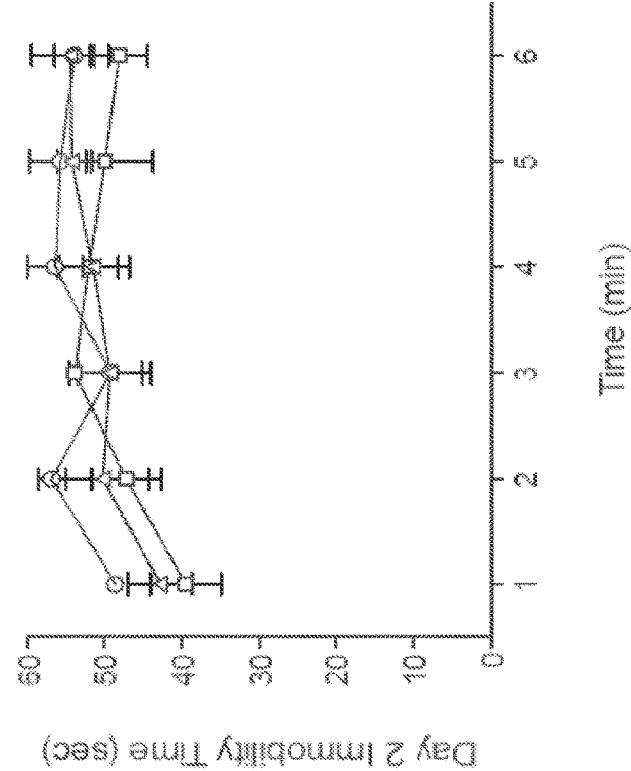
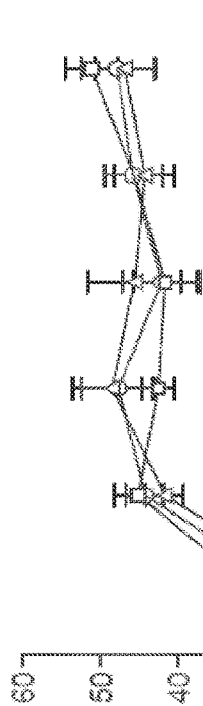
Fig. 9F
Fig. 9G

Contextual Fear Conditioning

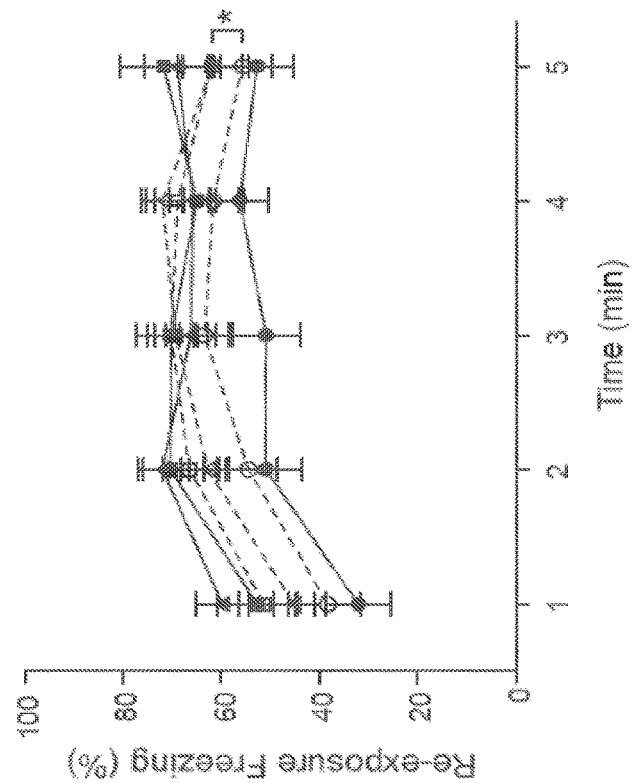
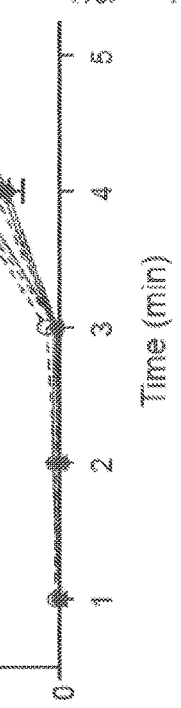
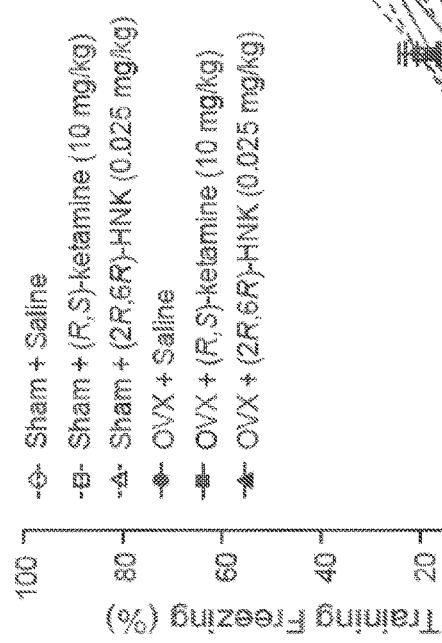
Fig. 10A
Fig. 10B

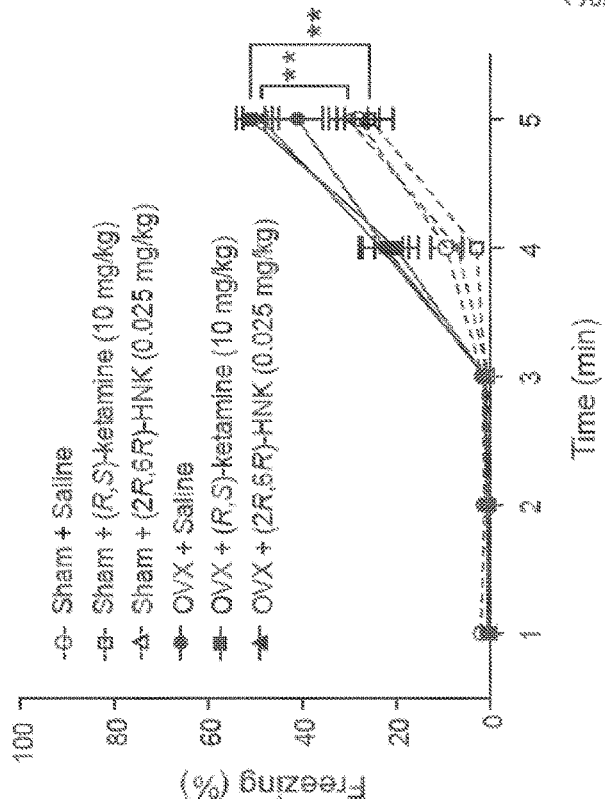
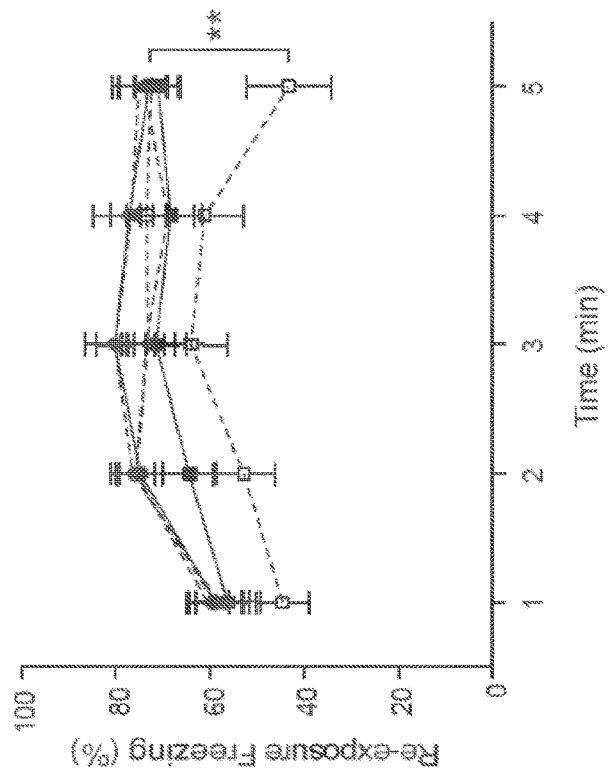
Fig. 10D
Fig. 10E

PHARMACOLOGICAL PROPHYLACTICS AGAINST STRESS-INDUCED AFFECTIVE DISORDERS IN FEMALES

The present application is a continuation of U.S. patent application Ser. No. 16/761,338 filed on May 4, 2020, now U.S. Pat. No. 11,491,120, issued on Nov. 8, 2022, which is a 371 of international Patent Application No. PCT/US2018/060082 filed on Nov. 9, 2018, and claims priority to U.S. Provisional Patent Application No. 62/583,774 filed on Nov. 9, 2017, each of which is incorporated herein by reference herein in its entirety.

PARTIES TO A JOINT RESEARCH AGREEMENT

The presently claimed invention was made by or on behalf of the below listed parties to a joint research agreement. The joint research agreement was in effect on or before the effective filing date of the claimed invention, and the claimed invention was made as a result of activities undertaken within the scope of the joint research agreement. The parties to the joint research agreement are THE TRUSTEES OF COLUMBIA UNIVERSITY IN THE CITY OF NEW YORK and the RESEARCH FOUNDATION FOR MENTAL HYGIENE, INC.

FIELD OF THE INVENTION

The present invention relates to ketamine and ketamine metabolite compositions and their use in methods of treatment or prevention of stress-induced affective disorders such as post-traumatic stress disorder (PTSD). In certain aspects, a ketamine composition can be administered prior to a stressor.

BACKGROUND OF THE INVENTION

MDD is the leading cause of disability worldwide, affecting more than 300 million people, and results from social, psychological, and biological factors (1). In 80% of cases, a traumatic event triggers the first major depressive episode, after which symptoms persist throughout an individual's lifetime (2). MDD has a high comorbidity rate with other psychiatric disorders, including post-traumatic stress disorder (PTSD); approximately half of patients suffering from PTSD are concurrently diagnosed with depression, the majority of which are women (3-5). Regardless of age or socioeconomic status, women are twice as likely as men to be diagnosed with depression and develop MDD earlier in life (1,5). fMRI data also suggest that women experience fear more strongly than men and process trauma through distinct brain circuits (6). Given these sex-specific differences, it is necessary to develop more specific and efficacious treatments for female populations.

Current treatments for MDD include cognitive behavioral therapy (CBT), lifestyle changes, and medication, but these treatments are not sex-specific. Moreover, antidepressant medications were developed in male, but not female, animal models and have been shown to exhibit sex-specific differences in efficacy. One study found that tricyclic antidepressants were more effective in men whereas selective serotonin re-uptake inhibitors (SSRIs) were more effective in women (7). Furthermore, the response rate to SSRI treatment was shown to be significantly higher in pre-menopausal women than in post-menopausal women (7). Another study found that SSRIs were more effective in post-menopausal women concurrently undergoing hormone replacement therapy (HRT) than in women who were not administered HRT (8). Thus, systemic levels of gonadal hormones, either endogenous or exogenous, may impact antidepressant efficacy and treatment outcome in women.

Despite the prevalence of antidepressants, these drugs are slow to take effect and fail to alleviate symptoms in up to 30% of patients (9). Alternatively, ketamine has become a promising antidepressant for treatment-resistant MDD (TRD) (10). When given at sub-anesthetic doses, ketamine has a rapid antidepressant onset of 2 hours in humans and 30 minutes in mice and can last up to 2 weeks (11-12). Moreover, antidepressant ketamine has been shown to act in a sex-specific manner (13-15). Controlling for weight, females are more sensitive than males to ketamine and require a lower concentration to reverse depressive-like behaviors; doses beneficial to males are depressogenic and anxiogenic in females (16-17). These data underscore the need for further sex-specific investigation into the use of ketamine in MDD treatment.

However, few studies have explored pharmacologically-based approaches to prevent the development of MDD. It has been shown that a single sub-anesthetic dose of ketamine, administered one week prior to a stressor, can protect against the onset of stress-induced depressive-like behavior and social avoidance, and attenuate learned fear in male mice, suggesting the possibility of developing resilience-enhancing pharmacotherapy (18-19). This effect has since been replicated in both mice and rats (20-21).

While the molecular mechanisms underlying ketamine's prophylactic efficacy remain unclear, exploring the metabolism of ketamine may offer insights into its in vivo actions. Ketamine is racemic mixture of R and S enantiomers, and studies to determine potential efficacy differences in enantiomers are ongoing (Paul et al., (R,S)-Ketamine metabolites (R,S)-norketamine and (2S,6S)-hydroxynorketamine increase the mammalian target of rapamycin function. Anesthesiology. 2014 July; 121(1): pp. 149-59). Ketamine, and its metabolite hydroxynorketamine (HNK), have been shown in numerous studies to be an effective treatment for depressive symptoms in mice.

Ketamine is stereoselectively metabolized into a variety of compounds, including (R,S)-norketamine and (2R,6R;2S, 6S)-hydroxynorketamine (HNK). (2R,6R;2S,6S)-HNK is the major metabolite found in the brain following ketamine infusion, comprising 15% of the original ketamine dose (22-23). Several studies have indicated that HNK may be an effective treatment route for MDD; however, the relative potency of each of its diastereoisomers ((2S,6S)-HNK; (2R,6R)-HNK) remains controversial. The lack of information on the influence of HNK stereoisomers and sex differences have limited its use. Although some studies suggest that the R enantiomer of HNK, (2R,6R)-HNK, may be necessary for the antidepressant effects of racemic ketamine, the data remain unclear. For example, whereas Zanos et al. have demonstrated that administering an altered form of (R,S)-ketamine that cannot be metabolized to (2R,6R)-HNK is not antidepressant, data from the Hashimoto group show that blocking the metabolism of ketamine using cytochrome P450 enzyme inhibitors does not impede the antidepressant actions of the precursor (24-25). Thus, further investigation is needed to determine if (2R,6R)-HNK may be developed for future use as an effective antidepressant or prophylactic. In addition, previous work has led to the widespread belief that only the S enantiomer of hydroxynorketamine is biologically active. Our study shows that (2R,6R)-HNK is more active than its S enantiomer in preventing depression in both sexes. This discovery could help form the basis for the development of novel compounds that can effectively prevent stress-induced depression in both men and women. Moreover, our identification of the active metabolite enantiomer could translate to more effective and longer-lasting prophylactics with fewer unintended side-effects.

SUMMARY

The present disclosure provides for a method for preventing or delaying a stress-induced affective disorder or stress-induced psychopathology in a female subject. The present disclosure provides for a method for inducing and/or enhancing stress resilience in a female subject. The method may comprise administering a pharmaceutic composition to the female subject prior to a stressor (e.g., prior to the onset of a stressor).

The pharmaceutic composition may comprise an effective amount of an agent. The agent may be selected from the group consisting of ketamine, a ketamine analog, a ketamine derivative, a metabolite of ketamine or a ketamine analog, and a pharmaceutically acceptable salt thereof.

In certain embodiments, the effective amount of the agent is no greater than 90%, no greater than 80%, no greater than 70%, no greater than 60%, no greater than 50%, no greater than 40%, no greater than 30%, no greater than 20%, or no greater than 10%, about 10% to about 90%, about 15% to about 80%, about 20% to about 70%, about 25% to about 60%, about 30% to about 50%, about 30% to about 40%, about 25% to about 40%, about 20% to about 30%, about 25% to about 35%, about 10% to about 30%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 20% to about 50%, about 12.5% to about 80%, about 20% to about 70%, about 25% to about 60%, or about 25% to about 50%, about of an effective amount of the agent administered to a male subject.

In certain embodiments, the pharmaceutic composition is administered to the female subject at a time point $T_f$ hours (or days, weeks, months, years, etc.) prior to a stressor, wherein $T_f$ is no greater than 90%, no greater than 80%, no greater than 70%, no greater than 60%, no greater than 50%, no greater than 40%, no greater than 30%, no greater than 20%, no greater than 10%, about 10% to about 90%, about 15% to about 80%, about 20% to about 70%, about 25% to about 60%, about 30% to about 50%, about 30% to about 40%, about 25% to about 40%, about 20% to about 30%, about 25% to about 35%, about 10% to about 30%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 20% to about 50%, about 12.5% to about 80%, about 20% to about 70%, about 25% to about 60%, or about 25% to about 50%, of a time point $T_m$ hours (or days, weeks, months, years, etc.) prior to a stressor for administration to a male subject.

The agent may be (R,S)-ketamine. The agent may be (2R,6R)-hydroxynorketamine ((2R,6R)-HNK). The agent may be any compound described herein.

The agent may be an antagonist of the glutamate N-methyl-D-aspartate (NMDA) receptor. The antagonist of the NMDA receptor may comprise ketamine, a ketamine analog, or a pharmaceutically acceptable salt, derivative, or metabolite thereof.

The agent may be an α-amino-3-hydroxy-5-methyl-4-isoxazolepropionic acid (AMPA) receptor agonist. The AMPA receptor agonist may be selected from the group consisting of glutamate, AMPA, 5-fluorowillardiine, domoic acid, quisqualic acid, and (2R,6R)-hydroxynorketamine, CX546, or a pharmaceutically acceptable salt, derivative, or metabolite thereof.

The pharmaceutic composition may be administered to the subject about 48 hours to about 3 weeks, about 72 hours to about 2 weeks, about 1 week, about 13 days, about 12 days, about 11 days, about 10 days, about 9 days, about 8 days, about 7 days, about 6 days, about 5 days, about 4 days, about 3 days, about 2 days, or about 1 day, prior to a stressor.

The pharmaceutic composition may be administered to the subject once prior to a stressor. The pharmaceutical composition may be administered in a booster series.

The pharmaceutic composition may be administered orally, intravenously, intranasally, or via injection to the subject.

The stress-induced affective disorder may comprise major depressive disorder (MDD) and/or posttraumatic stress disorder (PTSD).

The stress-induced affective disorder may be selected from the group consisting of: depressive-like behavior and associated affective disorders, anhedonic behavior and associated affective disorders, anxiety and associated affective disorders, cognitive impairments and deficits and associated disorders, and combinations thereof.

The stress-induced affective disorder may comprise stress-induced psychopathology.

The stress-induced psychopathology may comprise depressive and/or anxious behavior.

The subject may be a mammal, such as a human.

The method may prevent or delay stress-induced cognitive impairment and/or decline.

The method may further comprise administering an effective amount of an anti-depressant, an anxiolytic, or combinations thereof.

The method may further comprise administering an effective amount of a selective serotonin reuptake inhibitor (SSRI), or a pharmaceutically acceptable salt or derivative thereof.

The method may further comprise administering an effective amount of fluoxetine, paroxetine, sertraline, lithium, riluzole, prazosin, lamotrigine, ifenprodil, or combinations thereof.

BRIEF DESCRIPTION OF THE DRAWINGS

FIGS. 1A-1J. (R,S)-ketamine and (2R,6R)-HNK protect against stress-induced depressive-like behavior in female mice. (A) Experimental design. (B), (C), (D) Racemic ketamine, (2R,6R)-HNK, and (2S,6S)-HNK do not significantly alter freezing during re-exposure to the training context. (E) (R,S)-ketamine (10 mg/kg) mice showed significantly reduced average immobility on FST Day 2. (F) Similarly, (2R,6R)-HNK (0.025 mg/kg) mice were significantly less immobile than control saline mice on FST Day 2. (G) All doses of (2S,6S)-HNK failed to reduce average immobility. Average immobility time was averaged over the last 4 minutes of the test. (H), (I) (R,S)-ketamine (10 mg/kg) and (2R,6R)-HNK (0.025 mg/kg) did not alter distance travelled or time in the center of the OF compared to saline. (J) Similarly, nociception was not significantly affected by prophylactic drug administration in female mice. (n=8-22 female mice per group). Error bars represent ±SEM. * $p<0.05$. ** $p<0.01$. Sal, Saline; K, Ketamine; HNK, hydroxynorketamine; CFC, contextual fear conditioning; FST, forced swim test; OF, open field; TI, tail immersion test; sec, seconds; cm, centimeters; min, minutes.

FIGS. 3A-3F. (R,S)-ketamine and (2R,6R)-HNK are efficacious as prophylactics against CIS in female mice. (A) Experimental design. (B, C) (R,S)-ketamine and (2R,6R)-HNK mice exhibited significantly reduced immobility in the FST when compared to saline mice. (D) There were no significant changes in fear acquisition between the groups. (E) There was no change in freezing behavior during context re-exposure. (F) Average freezing during re-exposure was similar across all groups. (n=9-10 mice per group). Error bars represent ±SEM. * $p<0.05$. ** $p<0.01$. Sal, Saline; K, ketamine; HNK, hydroxynorketamine; CIS, chronic immobilization stress; FST, forced swim test; CFC, contextual fear conditioning; sec, seconds; min, minutes.

FIGS. 4A-4I. (R,S)-ketamine and (2R,6R)-HNK are prophylactic in a LH stress model in female mice. (A) Experimental design. (B), (C), (D) (R,S)-ketamine and (2R,6R)-HNK did not alter session length or escape latency when compared to saline in the LH assay. (E), (F) (R,S)-ketamine (10 mg/kg) and (2R,6R)-HNK (0.025 mg/kg) significantly lowered immobility on FST Day 2 when compared to saline. (G) On average, mice administered (R,S)-ketamine spent more time in the open arms of the EPM compared to mice administered saline. (H) (R,S)-ketamine (10 mg/kg) mice spent significantly less time in the closed arms of the EPM compared to saline mice. (I) All groups spent a comparable amount of time in the center of the EPM. (n=10-15 female mice per group). Error bars represent ±SEM. * $p<0.05$. *** $p<0.0001$. Sal, Saline; K, ketamine; HNK, hydroxynorketamine; LH, learned helplessness; LH, learned helplessness; FST, forced swim test; EPM, elevated plus maze; sec, seconds; min, minutes.

FIGS. 5A-5F. Ovarian hormones are necessary and sufficient for the prophylactic efficacy of (R,S)-ketamine and (2R,6R)-HNK in female mice. (A) Experimental design. (B) (C) On FST Day 2, in the sham group, (R,S)-ketamine (10 mg/kg) and (2R,6R)-HNK (0.025 mg/kg) reduced immobility compared to saline controls. In mice administered OVX surgery, this prophylactic effect was ablated, and all drug groups displayed comparable immobility. (D) Experimental design. (E), (F) In ovariectomized mice administered vehicle controls, immobility in the FST was comparable across all drug groups. However, when E2 and P4 were restored cyclically, (R,S)-ketamine and (2R,6R)-HNK significantly reduced immobility when compared to saline controls. (n=10 mice per group). Error bars represent ±SEM. * $p<0.05$.  $p<0.01$. * $p<0.0001$. OVX, ovariectomy; E2, estrogen; P4, progesterone; Sal, saline; K, ketamine; HNK, hydroxynorketamine; CFC, contextual fear conditioning; FST, forced swim test; sec, seconds; min, minutes.

FIGS. 6A-6F. (R,S)-ketamine, (2R,6R)-HNK, and (2S, 6S)-HNK do not attenuate learned fear in female mice. (A), (B), (C) There was a significant effect of Drug and Time as well as an interaction during CFC Training. (A) (R,S)-ketamine (2.5, 10, or 30 mg/kg) did not alter freezing during 3-shock CFC training, (B) (2R,6R)-HNK (10 mg/kg) significantly lowered freezing when compared to saline. (C) (2S,6S)-HNK (0.1 mg/kg) mice froze significantly less while (2S,6S)-HNK (0.3 mg/kg) mice froze significantly more than saline mice. (D), (E), (F) (R,S)-ketamine, (2R, 6R)-HNK, and (2S,6S)-HNK did not alter overall freezing upon context re-exposure. Error bars represent ±SEM. * $p<0.05$. HNK, hydroxynorketamine; min, minutes.

FIGS. 7A-7F. Prophylactic (2R,6R)-HNK administered before 1 week prior to stress does not affect fear behavior in females. (A) R,S)-ketamine (2.5 and 10 mg/kg) significantly increased freezing during the last minute of the CFC Training session when compared to saline. All other experimental drug groups did not affect freezing behavior compared to saline mice. (B), (C) There is no significant difference in freezing between control saline and experimental drug groups during context re-exposure. (D) (2R,6R)-HNK (0.025 mg/kg) did not alter fear learning during CFC training when administered 24 hours before stress, (E), (F) nor did it alter fear expression during re-exposure. (n=9-10 female mice per group). Error bars represent ±SEM. * $p<0.05$. HNK, hydroxynorketamine; min, minutes.

FIGS. 8A-8I. (R,S)-ketamine and (2R,6R)-HNK does not affect fear behavior when administered before LH stress. There was no Drug×Time interaction for (A) time spent in the open arms, (B) time spend in the closed arms, or (C) time spent in the center of the EPM. (D) All groups of mice had a comparable amount of entries into the (D) open arms, (E) closed arms, and (F) center. During CFC, all groups of mice froze comparably during (G) training and (H), (I) re-exposure. (n=5-10 female mice per group). Error bars represent ±SEM. K, ketamine; HNK, hydroxynorketamine; sec, seconds; min, minutes.

FIGS. 9A-9K. (R,S)-ketamine and (2R,6R)-HNK are not efficacious as antidepressants in 129S6/SvEv female mice. (A) Experimental design. (B) Mice displayed comparable levels of immobility across all drug groups on FST Day 1. (C) (R,S)-ketamine mice were significantly less immobile than saline mice during the first minute, but immobility was comparable between the groups for the remainder of the session. (2R,6R)-HNK did not affect immobility throughout the FST. (D) Average immobility during the FST Day 2 was comparable across all groups. (n=5 female mice per group). (E) Experimental design. (F), (G), (H) Neither (R,S)-ketamine nor (2R,6R)-HNK significantly affected immobility time compared to saline during FST Day 1 and FST Day 2. (I) Although there was a significant interaction between Drug and Time during CFC training, a Fisher's PLSD revealed no significant differences in freezing between experimental drug and control saline groups. (J), (K) All groups froze comparably during re-exposure to the training context. Error bars represent ±SEM. * $p<0.05$. Sal, saline; K, ketamine; HNK, hydroxynorketamine; FST, forced swim test; CFC, contextual fear conditioning; sec, seconds; min, minutes.

FIGS. 10A-10F. (R,S)-ketamine and (2R,6R)-HNK do not significantly affect fear behavior in mice administered OVX or hormone replacement. (A) In both sham and OVX surgery groups, mice administered saline, (R,S)-ketamine (10 mg/kg), or (2R,6R)-HNK (0.025 mg/kg) displayed comparable freezing levels during CFC Training. (B), (C) During CFC Re-exposure, there was a significant effect of Drug but no significant effect of Surgery or of Drug×Surgery. A Fisher's PLSD revealed that sham (R,S)-ketamine and sham (2R,6R)-HNK groups had significantly altered freezing when compared to sham saline. (D) Mice administered E2/P4+(R,S)-ketamine froze significantly more than mice administered vehicle+(R,S)-ketamine. Similarly, E2/P4+ (2R,6R)-HNK mice exhibited increased freezing when compared to vehicle+(2R,6R)-HNK mice. (E), (F) A 2-way ANOVA revealed a significant effect of Drug during CFC re-exposure. There was no significant effect of Hormone and no Drug×Hormone interaction. In the vehicle group, (R,S)-ketamine mice froze significantly less than saline mice. Vehicle+saline and vehicle+(2R,6R)-HNK mice froze at comparable levels. There was no difference in freezing between experimental and control drug groups in the E2/P4 condition. (n=7-14 female mice per group). Error bars represent ±SEM. * p<0.05,  p<0.01, * p<0.001. E2, estrogen; P4, progesterone; OVX, ovariectomized.

DETAILED DESCRIPTION OF THE INVENTION

Figure 1A:
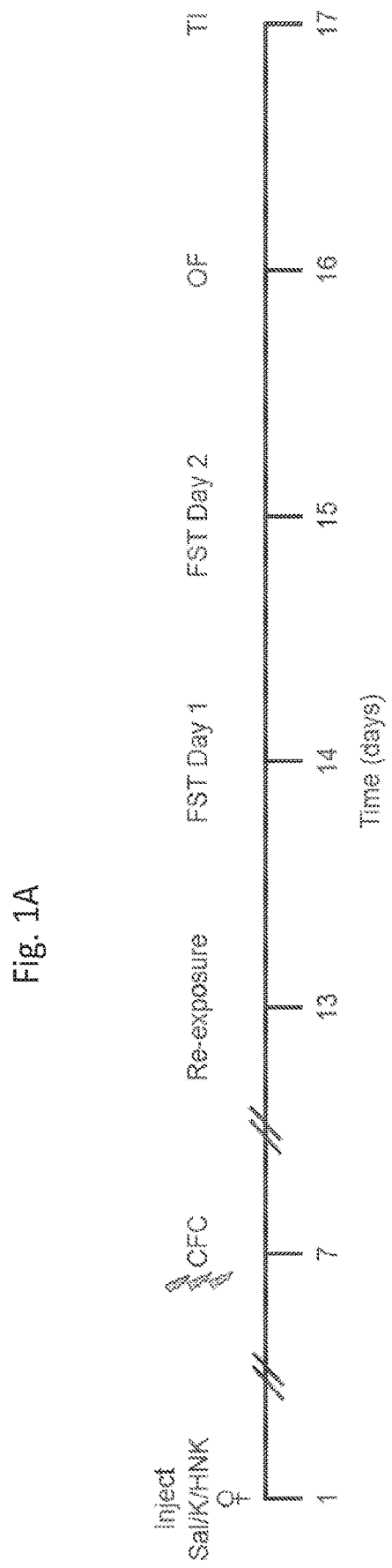

The present disclosure provides for an effective, sex-specific prophylactic treatment for depressive behaviors. A single administration of sub-anesthetic (R,S)-ketamine or (2R,6R)-hydroxynorketamine (HNK) may be dosed in a sex-specific manner, which can protect against the onset of depression in both female and male subjects. The present method/composition provides a potent and effective ketamine-derived prophylactic and antidepressant for both females and males. The present method/composition also prevents depression with sex-specific doses of ketamine, ketamine analogues, ketamine metabolites, ketamine derivatives, and pharmaceutically acceptable salts thereof.

The present method/composition may provide protection against the onset of depression in a female subject. The present composition can be sex-specifically dosed to prevent depression in a female or male subject.

The present disclosure provides for prophylaxis and treatment of depression. In one embodiment, sex-specific ketamine dosing strategy is used for treating and/or preventing depression. The present disclosure also provides for a research tool for studying sex differences in depression and efficacy of treatment. Also encompassed by the present disclosure are treatment and prophylactic for anxiety, PTSD, PMDD, post-partum depression, etc. The present disclosure provides for targeted drug development of ketamine analogues, ketamine metabolites, ketamine derivatives, and pharmaceutically acceptable salts thereof.

The present disclosure provides for a method for preventing or delaying a stress-induced affective disorder or stress-induced psychopathology in a female subject. The present disclosure provides for a method for inducing and/or enhancing stress resilience in a female subject.

The method may comprise administering a pharmaceutic composition to the female subject prior to a stressor. The effective amount of the agent for administration to a female subject may be no greater than 90%, no greater than 80%, no greater than 70%, no greater than 60%, no greater than 50%, no greater than 40%, no greater than 30%, no greater than 20%, no greater than 10%, about 10% to about 90%, about 15% to about 80%, about 20% to about 70%, about 25% to about 60%, about 30% to about 50%, about 30% to about 40%, about 25% to about 40%, about 20% to about 30%, about 25% to about 35%, about 10% to about 30%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 20% to about 50%, about 12.5% to about 80%, about 20% to about 70%, about 25% to about 60%, or about 25% to about 50%, of the effective amount/dose administered to a male subject.

The pharmaceutic composition may comprise an effective amount of an agent selected from the group consisting of ketamine, a ketamine analog, a ketamine derivative, a metabolite of ketamine or a ketamine analog, and a pharmaceutically acceptable salt thereof.

The method may comprise administering a pharmaceutic composition to the female subject prior to a stressor. The pharmaceutic composition may be administered to the female subject at a time point $T_f$ hours (or days, weeks, months, years, etc.) prior to a stressor (e.g., prior to the onset of a stressor), where $T_f$ is no greater than 90%, no greater than 80%, no greater than 70%, no greater than 60%, no greater than 50%, no greater than 40%, no greater than 30%, no greater than 20%, no greater than 10%, about 10% to about 90%, about 15% to about 80%, about 20% to about 70%, about 25% to about 60%, about 30% to about 50%, about 30% to about 40%, about 25% to about 40%, about 20% to about 30%, about 25% to about 35%, about 10% to about 30%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 20% to about 50%, about 12.5% to about 80%, about 20% to about 70%, about 25% to about 60%, or about 25% to about 50%, of a time point $T_m$ hours (or days, weeks, months, years, etc.) prior to a stressor for administration to a male subject.

In one embodiment, the agent is (R,S)-ketamine. In another embodiment, the agent is (2R,6R)-hydroxynorketamine ((2R,6R)-HNK).

The present disclosure describes that ketamine and ketamine metabolites exhibit primary prophylactic efficacy. The present disclosure provides methods for prophylactically treating a stress-induced affective disorder or stress-induced psychopathology in a subject. Also encompassed by the present disclosure are methods for inducing and/or enhancing stress resilience in a subject. In certain embodiments, an effective amount of an antagonist of the glutamate N-methyl-D-aspartate (NMDA) receptor, such as ketamine or a pharmaceutically acceptable salt or derivative thereof, is administered to a subject prior to a stressor.

The present agent/composition may be administered therapeutically to achieve a therapeutic benefit or prophylactically to achieve a prophylactic benefit. By therapeutic benefit is meant eradication or amelioration of the underlying stress-induced affective disorder being treated, and/or eradication or amelioration of one or more of the symptoms associated with the underlying disorder. By prophylactic benefit is meant prevention or delay of the onset of a stress-induced affective disorder, and/or prevention or delay of the onset of one or more of the symptoms associated with a stress-induced affective disorder. In certain embodiments, an effective amount of the present agent/composition to be administered prevents stress-related disorders from developing or being exacerbated into more serious conditions.

In certain embodiments, for prophylactic administration, the present agent/composition may be administered to a patient at risk of developing a stress-induced affective disorder, or to a patient reporting one or more of the physiological symptoms of a stress-induced affective disorder, even though a diagnosis of a stress-induced affective disorder may not have yet been made. In certain embodiments, prophylactic administration is applied to avoid the onset of the physiological symptoms of the underlying disorder, before the symptom manifests cyclically. In this latter embodiment, the therapy is prophylactic with respect to the associated physiological symptoms instead of the underlying indication. In certain embodiments, the present agent/composition is administered prior to recurrence of a stressor. In certain embodiments, the present agent/composition is administered prior to the onset of a particular symptom.

In a further embodiment, the present invention provides for the use of the present agent or a pharmaceutically acceptable salt or solvate thereof, or a physiologically functional derivative thereof, in the preparation of a medicament for the treatment of a stress-induced affective disorder.

"Treating" or "treatment" of a state, disorder or condition includes:
(1) preventing or delaying the appearance of clinical symptoms of the state, disorder, or condition developing in a person who may be afflicted with or predisposed to the state, disorder or condition but does not yet experience or display clinical symptoms of the state, disorder or condition; or
(2) inhibiting the state, disorder or condition, i.e., arresting, reducing or delaying the development of the disease or a relapse thereof (in case of maintenance treatment) or at least one clinical symptom, sign, or test, thereof; or
(3) relieving the disease, i.e., causing regression of the state, disorder or condition or at least one of its clinical or sub-clinical symptoms or signs.

The benefit to a subject to be treated is either statistically significant or at least perceptible to the patient or to the physician.

A "prophylactically effective amount" refers to an amount effective, at dosages and for periods of time necessary, to achieve the desired prophylactic result. In certain embodiments, since a prophylactic dose is used in subjects prior to or at an earlier stage of a disorder, the prophylactically effective amount is less than the therapeutically effective amount. In certain embodiments, the prophylactically effective amount is similar to, identical to, or more than, the therapeutically effective amount.

A therapeutically effective amount, or an effective amount, of a drug is an amount effective to demonstrate a desired activity of the drug. A "therapeutically effective amount" will vary depending on the compound, the disorder and its severity and the age, weight, physical condition and responsiveness of the subject to be treated. In certain embodiments, a effective amount of ketamine, or a pharmaceutically acceptable salt or solvate thereof, or a physiologically functional derivative thereof, is an amount effective to prevent or delay the onset of a stress-induced affective disorder, and/or effective to alleviate, one or more of the symptoms of a stress-induced affective disorder.

In certain embodiments, an effective amount of the present agent is a sub-anesthetic amount of ketamine, or a pharmaceutically acceptable salt or solvate thereof, or a physiologically functional derivative thereof. In certain embodiments, an effective amount of the present agent is a sub-analgesic amount of ketamine, or a pharmaceutically acceptable salt or solvate thereof, or a physiologically functional derivative thereof.

In certain embodiments, a subject is treated with ketamine, or a pharmaceutically acceptable salt or solvate thereof, or a physiologically functional derivative thereof, via intravenous, oral, transdermal or intranasal administration. In certain embodiments, a subject is injected with ketamine, or a pharmaceutically acceptable salt or solvate thereof, or a physiologically functional derivative thereof.

In certain embodiments, a subject is treated with a single dose of an effective amount of ketamine, or a pharmaceutically acceptable salt or solvate thereof, or a physiologically functional derivative thereof, prior to and/or after a stressor. In some aspects, a subject is treated with multiple doses of an effective amount of ketamine, or a pharmaceutically acceptable salt or solvate thereof, or a physiologically functional derivative thereof, prior to and/or after a stressor.

In certain embodiments, the present agent, such as ketamine, or a pharmaceutically acceptable salt or solvate thereof, or a physiologically functional derivative thereof, is administered in a composition comprising a pharmaceutically acceptable carrier, excipient or diluent. Also provided herein is a pharmaceutical composition that comprises ketamine, or a pharmaceutically acceptable salt or solvate thereof, or a physiologically functional derivative thereof, and a pharmaceutically acceptable carrier, excipient or diluent, for use in the prophylactic treatment of a stress-induced affective disorder.

"Patient" or "subject" refers to mammals and includes human and veterinary subjects. In certain embodiments, the subject is mammalian.

Ketamine

Ketamine ((RS)-2-(2-chlorophenyl)-2-(methylamino)cyclohexanone) is an antagonist of the glutamate N-methyl-D-aspartate (NMDA) receptor (NMDAR). Ketamine also acts on opioid receptors, sigma receptors, muscarinic receptors, monoamine transporters, etc.

Ketamine is a chiral compound. As used herein, the term "ketamine" may refer to (S)-ketamine (also referred to as S(+)-ketamine or esketanine), (R)-ketamine (R(−)-ketamine), or a racemic mixture of (S)-ketamine and (R)-ketamine. In certain embodiments, the ketamine compositions contain different proportions of the S(+) and R(−) stereoisomers. In certain embodiments, the ketamine compositions contain only (S)-ketamine or (R)-ketamine, or are enantiomerically enriched for a ketamine enantiomer. In certain embodiments, the ketamine composition is enriched to contain, for example, greater than 60%, greater than 70%, greater than 80%, greater than 90%, greater than 95%, greater than 99%, or greater than 99.9 of (S)-ketamine or (R)-ketamine.

Paul et al., "Comparison of racemic ketamine and S-ketamine in treatment-resistant major depression: report of two cases", World J. of Bio. Psych., 2009, pp 241-244, Vol. 10(3); Paskalis et al., Oral Administration of the NMDA Receptor Antagonist S-Ketamine as Add-on Therapy of Depression: A Case Series, Pharmacopsychiatry, 2010, pp 33-35, Vol. 40; Noppers et al., Absence of long-term analgesic effect from a short-term S-ketamine infusion on fibromyalgia pain: A randomized, prospective, double blind, active placebo-controlled trial", Eur. J. of Pain., 2011, 15(9): 942-9; Matthews et al., Ketamine for Treatment-Resistant Unipolar Depression, CNS Drugs, 2012, 1-16; and International Patent Publication No. WO2013138322.

The term "pharmaceutically acceptable derivative" refers to any pharmaceutically acceptable salt, solvate or prodrug, e.g. ester, of a compound which upon administration to the recipient is capable of providing (directly or indirectly) a compound or an active metabolite or residue thereof. Such derivatives are recognizable to those skilled in the art, without undue experimentation. Derivatives are described, for example, in Burger's Medicinal Chemistry and Drug Discovery, 5th Edition, Vol 1: Principles and Practice, which is incorporated herein by reference. In certain embodiments, pharmaceutically acceptable derivatives include salts, solvates, esters, carbamates, and phosphate esters. In one embodiment, the present composition contains a hydrochloride salt of ketamine.

The present agent may be administered by various routes, including intravenous (i.v. or IV), intranasal (i.n. or IN), intramuscular (i.m. or IM), caudal, intrathecal, and subcutaneous (s.c.) routes.

NMDA receptor antagonists-Ketamine and other compounds NMDA receptor antagonists are compounds that antagonize, or inhibit, the action of the NMDA receptor. An NMDA receptor antagonist may be a competitive antagonist, an uncompetitive antagonist, a noncompetitive antagonist, and/or a glycine antagonist.

Non-limiting examples of NMDA receptor antagonists include, ketamine, dextromethorphan (DXM), histogranin, memantine, meperidine, methadone, methoxetamine (MXE), phencyclidine (PCP), nitrous oxide ($N_2O$), AP5 (APV, R-2-amino-5-phosphonopentanoate), AP7 (2-amino-7-phosphonoheptanoic acid), CPPene ((3-[(R)-2-carboxypiperazin-4-yl]-prop-2-enyl-1-phosphonic acid), Selfotel, Amantadine, Atomoxetine, AZD6765, Agmatine, chloroform, dextrallorphan, dextromethorphan, dextrorphan, diphenidine, dizocilpine (MK-801), ethanol, eticyclidine, gacyclidine, ibogaine, magnesium, memantine, nitromemantine, rolicyclidine, tenocyclidine, methoxydine, tiletamine, neramexane, eliprodil, dexoxadrol, etoxadrol, remacemide, delucemine, WMS-2539, NEFA, 8A-PDHQ, HU-211, Aptiganel (Cerestat, CNS-1102), rhynchophylline, kynurenic acid, Rapastinel (GLYX-13), NRX-1074, 7-Chlorokynurenic acid, 4-Chlorokynurenine (AV-101), TK-40, 1-Aminocyclopropanecarboxylic acid (ACPC), L-Phenylalanine, Xenon, or analogs or derivatives thereof. Ketamine derivatives such as Rapastinel or Glyx-13 are also included. Rapastinel is an NMDA receptor glycine site partial agonist. It is an amidated tetrapeptide (Thr-Pro-Pro-Thr-$NH_2$) which rapidly crosses the blood brain barrier, but is not active orally.

Compounds that are mechanistically similar to ketamine are expected to be protective against stress-induced de novo psychopathology. Such compounds include:

Ro 25-6981, a GluN2B-selective antagonist (Miller O H, et al. (2014), eLife 3:e03581), which has been shown to have rapid antidepressant actions in rodent models of depression.

CP-101,606, a GluN2B-selective antagonist (Preskorn S, et al. (2007): A placebo-controlled trial of the NR2B specific NMDA antagonist CP-101, 606 plus paroxetine for treatment resistant depression (TRD). *American Psychological Association meeting*), which has been shown to be protective in animal models of brain injury and stroke.

GLYX-13, a novel N-methyl-D-aspartate receptor (NMDAR) glycine-site functional partial agonist and rapid-acting antidepressant (Burgdorf J, et al. (2013), *Neuropsychopharmacology* 38:729-42). GLYX-13 received Breakthrough Therapy designation from the U.S. Food and Drug Administration (FDA) for adjunctive treatment of MDD in January, 2016, and CX546 (Tocris), an ampakine (an AMPA receptor agonist) (Zhou W, et al. (2014), *Eur. Psychiatry* 29:419-23), which relieves the respiratory depression induced by fentanyl.

Non-limiting examples of the NMDA receptor antagonists also include anti-receptor antibodies, anti-ligand antibodies, etc.

Several synthetic opioids function as NMDA receptor-antagonists, such as pethidine, methadone, meperidine, dextropropoxyphene, tramadol, levorphanol, and ketobemidone.

AMPA Receptor Agonists

AMPA receptor agonists are compounds that activate the action of the α-amino-3-hydroxy-5-methyl-4-isoxazolepropionic acid (AMPA) receptor. It is expected that compounds that activate the AMPA receptor, including metabolites, will have a similar effect as the present effects shown with ketamine, in view of recent findings that a ketamine metabolite's antidepressant activity in mice was due to sustained activation of the AMPA receptor, rather than inhibiting NMDAR. (See, Zanos et al., (2016). "NMDAR inhibition-independent antidepressant actions of ketamine metabolites. Nature, 533: 481-486.)

Thus, in certain embodiments, AMPA receptor agonists may be used in the methods described herein. Non-limiting examples of the AMPA receptor agonists include glutamate, AMPA, 5-fluorowillardiine, domoic acid, quisqualic acid, (2R,6R)-hydroxynorketamine, CX546, etc.

Ketamine Metabolites

Ketamine is a derivative of arylcyclohexylamine and contains a chiral center. Since the 1950s, a large number of arylcyclohexylamines have been synthesized: these compounds have shown a wide range of possible pharmacological activities. When administered orally, it undergoes first-pass metabolism, where it is stereo selectively metabolized into a broad array of metabolites, including norketamine, hydroxyketamines, dehydronorketamine and hydroxynorketamine (HNK). After ketamine administration, (2S,6S;2R,6R)-HNK are the two major HNK metabolites found in the plasma and brain. Interestingly, a recent study has shown that the (2R,6R)-HNK metabolite is: 1) essential for the antidepressant effects of ketamine, 2) dependent on α-amino-3-hydroxy-5-methyl-4-isoxazolepropionic acid (AMPA) receptor activation, and 3) non-hypnotic (Zanos et al., 2016). All of these compounds are expected to behave similarly in the presently described methods, including enantiomers and non-psychotomimetic metabolites of ketamine.

The present disclosure also encompasses ketamine's enantiomers and non-psychotomimetic metabolites. Such compounds include:

1. (2R,6R)-HNK, a metabolite of ketamine that may mediate the antidepressant effects of ketamine and lacks the ketamine-related side effects (Zanos et al., 2016)
2. (2S,6S)-HNK, a metabolite of ketamine (Zanos et al., 2016, synthesis of these compounds (2R,6R)-HNK and (2S,6S)-HNK are described in Zanos et al. 2016 and Wainer et al. WO 2013/056229 (2013), The use of (2R,6R)-hydroxynorketamine, (S)-dehydronorketamine and other stereoisomeric dehydro and hydroxylated metabolites of (R,S)-ketamine in the treatment of depression and neuropathic pain).
3. (R)-ketamine, the R-enantiomer of ketamine, which has rapid-onset and sustained antidepressant effects without psychotomimetic side effects (Yang et al., 2015), and
4. (S)-ketamine, the S-enantiomer of ketamine, which is being developed as an intranasal spray, currently in phase III clinical trials for treatment-resistant depression.

Finally, other ketamine analogs are also expected to be protective. Such compounds include:

5. Fluorodeschloroketamine, an analog of ketamine where the chlorine (Cl) group has been replaced by fluorine (F), and
6. Tiletamine, an analog of ketamine commonly used as a veterinary anesthetic.

Pharmaceutical Compounds

The compounds used in the present methods include all hydrates, solvates, and complexes of the compounds. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

When the structure of the compounds used in this invention includes an asymmetric carbon atom such compound can occur as racemates, racemic mixtures, and isolated single enantiomers. All such isomeric forms of these compounds are expressly included in this invention. Each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "*Enantiomers, Racemates and Resolutions*" by J. Jacques, A. Collet and S. Wilen, Pub. John Wiley & Sons, N Y, 1981. For example, the resolution may be carried out by preparative chromatography on a chiral column.

The present disclosure is also intended to include use of all isotopes of atoms occurring on the compounds disclosed herein. Isotopes include those atoms having the same atomic number but different mass numbers. Isotopically-labeled compounds can generally be prepared by conventional techniques known to those skilled in the art or by processes analogous to those described in the Examples disclosed herein using an appropriate isotopically-labeled reagents in place of the non-labeled reagents employed.

The compounds of the instant invention may be in a salt form. As used herein, a "salt" is a salt of the instant compound which has been modified by making acid or base, salts of the compounds. In the case of compounds used for treatment of mammals, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately treating a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

The present methods also encompass administering a physiologically functional derivative of the present compound. As used herein, the term "physiologically functional derivative" refers to a compound (e.g, a drug precursor) that is transformed in vivo to yield the present compound or its active metabolite, or a pharmaceutically acceptable salt, hydrate or solvate of the compound. The transformation may occur by various mechanisms (e.g., by metabolic or chemical processes), such as, for example, through hydrolysis in blood. Prodrugs are such derivatives, and a discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Dosages

In certain embodiments, the effective amount of the present compound is a dose of about 0.01 to about 3 mg of ketamine per kilogram of body weight of the subject (mg/kg), i.e., from about 0.01 mg/kg to about 3 mg/kg body weight. In certain embodiments, the effective amount of the present compound ranges 0.001 to approximately 3 mg/kg body weight, 0.001 to approximately 2 mg/kg body weight, from about 0.01 mg/kg to about 3 mg/kg body weight, from about 0.01 to about 2 mg/kg of body weight, about 0.01 to about 1.5 mg/kg of body weight, about 0.05 to about 1.4 mg/kg of body weight, about 0.05 to about 1.3 mg/kg of body weight, about 0.05 to about 1.2 mg/kg of body weight, about 0.05 to about 1.1 mg/kg of body weight, about 0.01 to about 1 mg/kg of body weight, or about 0.05 to about 0.7 mg/kg of body weight. In some aspects, the dose is about 0.05 to about 0.5 mg/kg. In some aspects, the dose is less than about 0.5 mg/kg, less that about 0.4 mg/kg, or less than about 0.3 mg/kg body weight. In some aspects, the effective amount of the present compound is a dose in the range of from about 0.01 mg/kg to about 1.5 mg/kg body weight. In some aspects, the effective amount of the present compound is a dose in the range of from about 0.01 mg/kg to about 1 mg/kg body weight. In some aspects, the effective amount of the present compound is a dose in the range of from about 0.01 mg/kg to about 0.75 mg/kg body weight. In some aspects, the effective amount of the present compound is a dose in the range of from about 0.75 mg/kg to about 1.5 mg/kg body weight. In some aspects, the effective amount of the present compound is a dose in the range of from about 0.5 mg/kg to about 1.2 mg/kg body weight. In some aspects, the effective amount of the present compound is a dose in the range of from about 0.05 mg/kg to about 0.5 mg/kg. In some aspects, the effective amount of the present compound is a dose of about 0.2 mg/kg or about 0.4 mg/kg body weight. In some aspects, the dose of the present compound is, about 0.01 to about 1 mg/kg, about 0.1 to about 0.5 mg/kg, about 0.8 to about 1.2 mg/kg, about 0.7 to about 1.1 mg/kg, about 0.05 to about 0.7 mg/kg, about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, about 1.9 mg/kg, about 2.0 mg/kg, or about 3 mg/kg body weight.

In certain embodiments, the dose of the present compound per administration is from about 1 to about 250 mg, from about 10 mg to about 300 mg, about 10 mg to about 250 mg, about 10 to about 200 mg, about 15 to about 175 mg, about 20 to about 175 mg, about 8 mg to about 32 mg, about 50 mg to about 75 mg, about 25 to about 150 mg, about 25 to about 125 mg, about 25 to about 100 mg, about 50 to about 100 mg, about 50 mg to about 75 mg, about 75 mg to about 100 mg, or about 75 mg to about 200 mg, about 1 mg, 2 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, and 250 mg. In some aspects, the dose of the present compound is about 50 mg. In some aspects, the dose of the present compound is about 75 mg. In some aspects, the total dose of the present compound is about 100 mg.

In some aspects, the therapeutically effective amount of the present compound is a sub-anesthetic dose. In some aspects, the therapeutically effective amount of the present compound is a sub-analgesic dose. In certain embodiments, the therapeutically effective amount of the present compound is below the level that results in one or more side effects of the compound. In certain embodiments, the therapeutically effective amount of the present compound is an anesthetic dose or analgesic dose. U.S. Patent Publication No. 20160067196.

In some aspects, the (therapeutically) effective amount of the present compound is about 0.01 mg to about 1000 mg, from about 0.01 mg to about 500 mg, from about 0.1 mg to about 250 mg, or any amount or range therein. In another aspect, the (therapeutically) effective amount of the present compound is, e.g., 0.01 mg, 0.025 mg, 0.05 mg, 0.1 mg, 0.5 mg, 1 mg, 5 mg, 10 mg, 25 mg, 50 mg, 55 mg, 60 mg, 65 mg, 70 mg, 75 mg, 80 mg, 90 mg, 95 mg, 100 mg, 150 mg, 200 mg, 250 mg, or 500 mg.

In certain embodiments, a therapeutically effective dose of the present compound may be adjusted depending on conditions of the disease/disorder to be treated or prophetically treated, the age, body weight, general health conditions, sex, and diet of the subject, dose intervals, administration routes, excretion rate, and combinations of drugs.

An initial dose of the present compound may be larger, followed by one or more smaller maintenance doses. Other ranges are possible, depending on the subject's response to the treatment. An initial dose may be the same as, or lower or higher than subsequently administered doses.

The dose may be administered daily, weekly, biweekly, several times daily, semi-weekly, every other day, bi-weekly, quarterly, several times per week, semi-weekly, monthly etc., to maintain an effective dosage level. The duration and frequency of treatment may depend upon the subject's response to treatment.

In certain embodiments, a subject may be administered 1 dose, 2 doses, 3 doses, 4 doses, 5 doses, 6 doses or more of the present composition. In certain embodiments, a single dose of the present agent/composition is administered in the present method. In certain embodiments, multiple doses of the present agent/composition (e.g., 2 doses, 3 doses, 4 doses, 5 doses, 6 doses, 7 doses, 8 doses, 9 doses, 10 doses or more) are administered in the present method.

In certain embodiments, when there are more than one doses of the present compound/composition administered to a subject, the second dose is lower than the first dose. In certain embodiments, the second dose is an amount that is at most one-half, one-quarter, or one-tenth the amount of the first dose.

The number and frequency of doses may be determined based on the subject's response to administration of the composition, e.g., if one or more of the patient's symptoms improve and/or if the subject tolerates administration of the composition without adverse reaction.

In certain embodiments, the present agent/composition is administered at least once a day, at least twice a day, at least three times per day, or more. In certain embodiments, the present agent/composition is administered at least once a week, at least twice a week, at least three times per week, or more frequently. In certain embodiments, the present agent/composition is administered at least twice per month, or at least once per month.

Treatment using the present method can continue as long as needed.

Dosing Time Frame

In certain embodiments, the present agent/composition is administered to a subject prior to a stressor. In certain embodiments, the present agent/composition is administered to a subject both prior to and after a stressor. In certain embodiments, the present agent/composition is administered to a subject after a stressor. In certain embodiments, the present agent/composition is administered to a subject prior to a stressor, and again prior to a recurrence of the stressor or a different stressor.

In certain embodiments, the present agent/composition is administered to the subject about 12 hours to about 4 weeks, about 18 hours to about 4 weeks, about 1 day to about 3.5 weeks, about 2 days to about 3 weeks, about 3 days to about 3 weeks, about 4 days to about 3 weeks, about 5 days to about 3 weeks, about 6 days to about 3 weeks, about 2 days to about 2.5 weeks, about 3 days to about 2.5 weeks, about 4 days to about 2.5 weeks, about 5 days to about 2.5 weeks, about 6 days to about 2.5 weeks, about 1 week to about 2.5 weeks, about 1 week to about 2.5 weeks, about 1 week to about 2 weeks, about 3 days, about 4 days, about 5 days, about 6 days, about 1 week, about 8 days, about 9 days, about 10 days, about 11 days, about 12 days, about 13 days, about 2 weeks, about 2.5 weeks, about 3 weeks, about 3.5 weeks, or about 4 weeks, prior to, and/or after a stressor.

In certain embodiments, the administration of the present agent/composition is continued over a period of up to 2 days, up to 3 days, up to 4 days, up to 5 days, up to 6 days, up to 1 week, up to 2 weeks, up to 3 weeks, up to 4 weeks, 2 weeks, 3 weeks, 4 weeks, 5 weeks, 6 weeks, 7 weeks, 8 weeks, 9 weeks, 10 weeks, or longer.

In certain embodiments, the present agent/composition is administered once, twice, at least twice, at least three times, at least four times, at least five time, at least six times, at least seven times, at least eight times, at least nine times, or more per treatment.

In certain embodiments, the present agent/composition is administered at least once a day, at least twice a day, at least three times per day, at least once a week, at least twice a week, at least three times a week, at least once per month, at least twice per month, or more frequently. Treatment can continue as long as needed.

Stressors

A stressor is a stimulus that causes stress. It can be an event or other factor that disrupts the body's homeostasis of temperature, blood pressure, and/or other functions. In certain embodiments, a stressor is a traumatic or stressful event. Because humans have sophisticated brains and thought processes, anticipating a disruption can also be a stressor. In certain embodiments, a stressor is injury, trauma, combat, warfare, surgery, an accident, a criminal assault, child abuse, natural or human-caused disasters, a crash, grief, hunger, heat, cold, chemical exposure, autoimmune disease, infectious disease, viral infection, cancer, exhaustion, physical distress, neuropathy, hyperalgesia, allodynia, emotional distress, or depression. A traumatic event may be an event or something that threatens the person's life or the life of a close one or it could be something witnessed. U.S. Patent Application No. 20140018339.

A stressor may be acute, or may be chronic.

There are numerous physiological processes that are altered in response to stress. Among these are altered cortisol, corticotropin, catecholamine and serotonin levels. These levels return to baseline after an acute stressor is removed (McEwen N Eng J Med 1998 338(3):171-179). These biochemical markers of stress in turn lead to ill health and psychosocial disorders. Consequently, stress plays a major role in physical and mental health. Stress can affect the onset of, or susceptibility to disease. It can also affect the progression or course of disease even when there is another underlying pathophysiology of the disease. Recovery from an existing disease can also be delayed due to stress. For example, stress is a contributing factor to high blood pressure, heart disease, headaches, colitis, irritable bowel syndrome, temporo-mandibular joint disorder, cancer, peptic ulcers, insomnia, skin disorders and asthma. Stress can also aggravate other conditions such as multiple sclerosis, diabetes, herpes, mental illness, substance abuse and psychiatric disorders characterized by the presence of violent or aggressive tendencies. Particularly, stress contributes to functional somatic disorders, affective disorders and major depressive disorder. These include disorders such as chronic fatigue syndrome (CFS), fibromyalgia (FMS), Gulf War Syndrome, anxiety and post-traumatic stress disorder (PTSD). Stressors that disrupt normal exercise or sleep patterns.

Additional examples of use include administration prior to military deployment to protect Service members (active combat soldiers, battlefield surgeons, etc.) and even military working dogs against stress. Potential non-military use cases include, but are not limited to: police, firefighters, first responders, EMTs, ER doctors, prison guards (and prisoners), humanitarian aid workers, and refugees.

In certain embodiments, a subject may be administered the present agent or composition prior to a situation in which the subject (such as an early responder or military personnel) is likely to be exposed to traumatic stress, immediately after exposure to traumatic stress, and/or when the subject feels that his or her PTSD symptoms are likely to appear.

Resilience to Stress

Resilience to stress refers to the capacity of a subject to adapt or change successfully, and/or to maintain physiological, neurological, or psychological homeostasis, in the face of a stressor (e.g., adversity). As used herein, the term "enhancing resilience" refers to increasing the ability of a subject to experience a stressor (e.g., a traumatic event) without suffering a stress-induced affective disorder, and/or with less post-event symptomatology or disruption of homeostasis and/or normal activities of daily living. In certain embodiments, improving resilience can prevent a stress-induced affective disorder. In certain embodiments, improving resilience can reduce at least one of the signs, symptoms, or symptom clusters of a stress-induced affective disorder. In certain embodiments, the present method enhances a subject's resilience to stress, helps protect against developing stressor-related psychopathology, decrease the functional consequences of stressor-induced disorders (e.g., PTSD, etc.), and reduce medical morbidity and mortality.

The Connor-Davidson Resilience Scale (CD-RISC) is a 25-item self-report scale, each rated on a 5-point scale (0-4), with higher scores reflecting greater resilience (Connor K M & Davidson, J R T. Development of a new resilience scale: the Connor-Davidson Resilience Scale (CD-RISC). Depression and Anxiety, 2003: 18: 71-82).

Resilience, psychological growth and life satisfaction may be measured with the CD-RISC, the Purpose in Life Scale, the abbreviated MOS Social Support Survey, the PTGI, and the Q-LES-Q.

Combination Therapy

The present compound or composition may be administered to a subject alone, or may be administered to a subject in combination with one or more other treatments/agents.

In certain embodiments, the second agent is an antidepressant, an anxiolytic, or combinations thereof. In certain embodiments, the second agent is a serotonin reuptake inhibitor (SRI), or a selective serotonin reuptake inhibitor (SSRI). In certain embodiments, the second agent is fluoxetine, paroxetine, sertraline, lithium, riluzole, prazosin, lamotrigine, ifenprodil, or combinations thereof. In certain embodiments, the second agent is a dual serotonin norepinephrine reuptake inhibitor compound (DRI). In certain embodiments, the second agent is venlafaxine, duloxetine, milnacipran, or combinations thereof. In certain embodiments, the second agent is a non-tricyclic triple reuptake inhibitor (TRI).

In certain embodiments, the present compound or composition is administered to a subject in combination with one or more treatments/agents such as antidepressants, analgesics, muscle relaxants, anorectics, stimulants, antiepileptic drugs, and sedative/hypnotics. Non-limiting examples of compounds that can be administered in combination with the present compound or composition include, neurontin, pregabalin, pramipexole, L-DOPA, amphetamine, tizanidine, clonidine, tramadol, morphine, tricyclic antidepressants, codeine, carbamazepine, sibutramine, amphetamine, valium, trazodone and combinations thereof.

In certain embodiments, combination therapy means simultaneous administration of the compounds in the same dosage form, simultaneous administration in separate dosage forms, or separate administration of the compounds.

In certain embodiments, the second agent/treatment is used as adjunctive therapy to the present compound or composition. In certain embodiments, the treatment includes a phase wherein treatment with the second agent/treatment takes place after treatment with the present compound or composition has ceased. In certain embodiments, the treatment includes a phase where treatment with the present compound or composition and treatment with the second agent/treatment overlap.

Combination therapy can be sequential or can be administered simultaneously. In either case, these drugs and/or therapies are said to be "co-administered." It is to be understood that "co-administered" does not necessarily mean that the drugs and/or therapies are administered in a combined form (i.e., they may be administered separately (e.g., as separate compositions or formulations) or together (e.g., in the same formulation or composition) to the same or different sites at the same or different times).

In certain embodiments, a subject is treated concurrently (or concomitantly) with the present compound or composition and a second agent. In certain embodiments, a subject is treated initially with the present compound or composition, followed by cessation of the present compound or composition treatment and initiation of treatment with a second agent.

In certain embodiments, the present compound or composition is used as an initial treatment, e.g., by administration of one, two or three doses, and a second agent is administered to prolong the effect of the present compound or composition, or alternatively, to boost the effect of the present compound or composition. A person of ordinary skill in the art will recognize that other variations of the presented schemes are possible, e.g., initiating treatment of a subject with the present compound or composition, followed by a period wherein the subject is treated with a second agent as adjunct therapy to the present compound or composition treatment, followed by cessation of the present compound or composition treatment.

The present compound and the other pharmaceutically active agent(s) may be administered together or separately and, when administered separately this may occur simultaneously or sequentially in any order. The amounts of the present compound and the other pharmaceutically active agent(s) and the relative timings of administration will be selected in order to achieve the desired combined therapeutic effect.

In various embodiments, the therapies (e.g., a composition provided herein and a second agent in a combination therapy) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In certain embodiments, the therapies are administered no more than 24 hours apart or no more than 48 hours apart. In certain embodiments, two or more therapies are administered within the same patient visit. In other embodiments, the composition provided herein and the second agent are administered concurrently. In other embodiments, the composition provided herein and the second agent are administered at about 2 to 4 days apart, at about 4 to 6 days apart, at about 1 week part, at about 1 to 2 weeks apart, or more than 2 weeks apart. In certain embodiments, administration of the same agent may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same agent may be repeated and the administration may be separated by at least at least 1 day, 2 days, 3 days, 5 days, 10 days, 15 days, 30 days, 45 days, 2 months, 75 days, 3 months, or 6 months. In certain embodiments, a composition provided herein and a second agent are administered to a subject in a sequence and within a time interval such that the composition provided herein can act together with the other agent to provide an increased benefit than if they were administered otherwise. For example, the second active agent can be administered at the same time or sequentially in any order at different points in time; however, if not administered at the same time, they should be administered sufficiently close in time so as to provide the desired therapeutic or prophylactic effect. In one embodiment, the composition provided herein and the second active agent exerts their effect at times which overlap. Each second active agent can be administered separately, in any appropriate form and by any suitable route. In other embodiments, the composition provided herein is administered before, concurrently or after administration of the second active agent. The term "about" refers to +10% of the referenced value. In other embodiments, courses of treatment are administered concurrently to a patient, i.e., individual doses of the second agent are administered separately yet within a time interval such that the compound provided herein can work together with the second active agent. For example, one component can be administered once per week in combination with the other components that can be administered once every two weeks or once every three weeks. In other words, the dosing regimens are carried out concurrently even if the therapeutics are not administered simultaneously or during the same day. The second agent can act additively or synergistically with the compound provided herein. In one embodiment, the composition provided herein is administered concurrently with one or more second agents in the same pharmaceutical composition. In another embodiment, a composition provided herein is administered concurrently with one or more second agents in separate pharmaceutical compositions. In still another embodiment, a composition provided herein is administered prior to or subsequent to administration of a second agent. Also contemplated are administration of a composition provided herein and a second agent by the same or different routes of administration, e.g., oral and parenteral. In certain embodiments, when the composition provided herein is administered concurrently with a second agent that potentially produces adverse side effects including, but not limited to, toxicity, the second active agent can advantageously be administered at a dose that falls below the threshold that the adverse side effect is elicited.

Encompassed by the present disclosure are methods to prophylactically treat a subject prior to a stressor. In certain embodiments, the present method prevents or delays a stress-induced affective disorder or stress-induced psychopathology in a subject. In certain embodiments, stress-induced affective disorders include major depressive disorder and posttraumatic stress disorder.

Stress-Induced Affective Disorders

There are numerous disorders that are either caused by or exacerbated by stress. These include addictive disorders such as substance abuse, anorexia, bulimia, obesity, smoking addiction, and weight addiction; anxiety disorders such as agoraphobia, anxiety disorder, obsessive compulsive disorder, panic attacks, performance anxiety, phobias, and posttraumatic stress disorder; autoimmune diseases such as allergies, arthritis, fibromyalgia, fibromytosis, lupus, multiple sclerosis, rheumatoid arthritis, Sjogren's syndrome, and vitiligo; cancer such as bone cancer, brain cancer, breast cancer, cervical cancer, colon cancer, Hodgkin's disease, leukemia, liver cancer, lung cancer, lymphoma, multiple myeloma, ovarian cancer, pancreatic cancer, and prostate cancer; cardiovascular disorders such as arrhythmia, arteriosclerosis, Burger's disease, essential hypertension, fibrillation, mitral valve prolapse, palpitations, peripheral vascular disease, Raynaud's disease, stroke, tachycardia, and Wolff-Parkinson-White Syndrome; and developmental disorders such as attention deficit disorder, concentration problems, conduct disorder, dyslexia, hyperkinesis, language and speech disorders, and learning disabilities.

Anxiety Disorders

The five major types of anxiety disorders are: panic disorder, obsessive-compulsive disorder, post-traumatic stress disorder, generalized anxiety disorder and phobias (including social phobia, also called social anxiety disorder). Each anxiety disorder has its own distinct features, but they are all bound together by the common theme of excessive, irrational fear and dread. It is common for an anxiety disorder to accompany depression, eating disorders, substance abuse, or another anxiety disorder.

Panic disorder is characterized by repeated episodes of intense fear that strike often and without warning. Physical symptoms include chest pain, heart palpitations, shortness of breath, dizziness, abdominal distress, feelings of unreality, and fear of dying. Obsessive-compulsive disorder is characterized by repeated, unwanted thoughts or compulsive behaviors that seem impossible to stop or control. Generalized Anxiety Disorder is characterized by exaggerated worrisome thoughts and tension about everyday routine life events and activities, lasting at least six months. Almost always anticipating the worst even though there is little reason to expect it; accompanied by physical symptoms, such as fatigue, trembling, muscle tension, headache, or nausea. Phobias are characterized into two major types of phobias, social phobia and specific phobia. People with social phobia have an overwhelming and disabling fear of scrutiny, embarrassment, or humiliation in social situations, which leads to avoidance of many potentially pleasurable and meaningful activities. People with specific phobia experience extreme, disabling, and irrational fear of something that poses little or no actual danger; the fear leads to avoidance of objects or situations and can cause people to limit their lives unnecessarily.

Posttraumatic Stress Disorder (PTSD)

Typically, a subject suffering from PTSD was exposed to a traumatic event in which the person experienced, witnessed, or was confronted with an event or events that involved actual or threatened death or serious injury, or a threat to the physical integrity of self or others and the person's response involved intense fear, helplessness, or horror.

Having repeated intrusive memories of the trauma exposure is one of the core symptoms of PTSD. Patients with PTSD are known to display impairments in learning and memory during neuropsychological testing. Other core symptoms of PTSD include heightened stress sensitivity (startle), tension and anxiety, memory disturbances, and dissociation.

In certain embodiments, the present method prevents or inhibits the development of post-traumatic stress disorder (PTSD) in a subject. In certain embodiments, the present method prevents or inhibits the development of one or more PTSD-like symptoms. In certain embodiments, a subject may be administered the present agent or composition prior to a situation in which the subject (such as an early responder or military personnel) is likely to be exposed to traumatic stress, immediately after exposure to traumatic stress, and/or when the subject feels that his or her PTSD symptoms are likely to appear.

Typically, the traumatic event is persistently re-experienced in one or more of the following ways: recurrent and intrusive distressing recollections of the event, including images, thoughts, or perceptions, recurrent distressing dreams of the event, acting or feeling as if the traumatic event were recurring (includes a sense of reliving the experience, illusions, hallucinations, and dissociative flashback episodes, including those that occur on awakening or when intoxicated), intense psychological distress at exposure to internal or external cues that symbolize or resemble an aspect of the traumatic event, physiological reactivity on exposure to internal or external cues that symbolize or resemble an aspect of the traumatic event. An individual suffering from PTSD also has persistent avoidance of stimuli associated with the trauma and numbing of general responsiveness (not present before the trauma), as indicated by 3 or more of the following: efforts to avoid thoughts, feelings, or conversations associated with the trauma, efforts to avoid activities, places, or people that arouse recollections of the trauma, inability to recall an important aspect of the trauma, significantly diminished interest or participation in significant activities, feeling of detachment or estrangement from others, restricted range of affect (e.g., unable to have loving feelings), sense of a foreshortened future (e.g., does not expect to have a career, marriage, children, or a normal life span), persistent symptoms of increased arousal (not present before the trauma), as indicated by 2 or more of the following: difficulty falling or staying asleep, irritability or outbursts of anger, difficulty concentrating, hypervigilance, exaggerated startle response. The disturbance, which has lasted for at least a month, causes clinically significant distress or impairment in social, occupational, or other important areas of functioning.

In certain embodiments, the present compound or composition prevents, reduces, eliminates or delays one or more of the symptoms including, but not limited to, re-experiencing of the traumatic experience in the form of intrusive memories, nightmares, flashbacks; emotional and physical reactions triggered by reminders of the trauma; distancing from others; decreased interest in activities and other people; numbing of feelings; avoidance of trauma reminders; hyperarousal symptoms, including disrupted sleep, irritability, hypervigilance, decreased concentration; increased startle reflex; and combinations thereof.

Whatever the source of the problem, some people with PTSD repeatedly relive the trauma in the form of nightmares and disturbing recollections during the day. They may also experience other sleep problems, feel detached or numb, or be easily startled. They may lose interest in things they used to enjoy and have trouble feeling affectionate. They may feel irritable, more aggressive than before, or even violent. Things that remind them of the trauma may be very distressing, which could lead them to avoid certain places or situations that bring back those memories.

The disorder may be accompanied by depression, substance abuse, or one or more other anxiety disorders. In severe cases, the person may have trouble working or socializing.

Major Depressive Disorder

Major depressive disorder refers to a class of syndromes characterized by negative affect and repeated episodes of depression without any history of independent episodes of mood elevation and over-activity that fulfill the criteria of mania. Multiple subtypes of major depressive disorders are recognized, including these with atypical characteristics, psychotic components, etc. The age of onset and the severity, duration and frequency of the episodes of depression are all highly variable. The disorder may begin at any age. The symptoms of major depressive disorder typically develop over days to weeks. Prodromal symptoms include generalized anxiety, panic attacks, phobias or depressive symptoms and may occur during several months preceding the episode. Individual episodes also last between 3 and 12 months but recur less frequently. Most patients are asymptomatic between episodes, but a minority of patients may develop a persistent depression, mainly in old age. Individual episodes of any severity are often precipitated by stressful life events. Common symptoms of a depressive episode include reduced concentration and attention; reduced self-esteem and self-confidence; ideas of guilt and unworthiness, ideas or acts of self-harm or suicide; disturbed sleep; and diminished appetite. In certain embodiments, a major depressive episode follows a psychosocial stressor, e.g., death of a loved one, marital separation, childbirth or the end of an important relationship.

The lowered mood varies little from day to day and is often unresponsive to circumstances, yet may show a characteristic diurnal variation as the day goes on. As with manic episodes, the clinical presentation shows marked individual variations, and atypical presentations are particularly common in adolescence. In some cases, anxiety, distress, and motor agitation may be more prominent at times that the depression, and the mood change may also be masked by added features such as irritability, excessive consumption of alcohol, histrionic behavior, and exacerbation of pre-existing phobic or obsessional symptoms, or by hypochondria.

Psychiatric Evaluations

In certain embodiments, the effects or efficacy of treatment with the present agent/composition are evaluated by the subject and/or a medical professional, e.g., the subject's physician. In certain embodiments, the evaluation is conducted within about 10 minutes, within about 15 minutes, within about 20 minutes, within about 25 minutes, within about 0.5 hours, within about 1 hour, within about 2 hours, within about 2.5 hours, within about 3 hours, within about 3.5 hours, within about 4 hours, within about 4.5 hours, within about 5 hours, within about 5.5 hours, within about 6 hours, within about 6.5 hours, within about 7 hours, within about 7.5 hours, within about 8 hours, within about 8.5 hours, within about 9 hours, within about 9.5 hours, within about 10 hours, within about 10.5 hours, within about 11 hours, within about 11.5 hours, within about 12 hours, within about 18 hours, within about 1 day, within about 2 days, within about 3 days, within about 4 days, within about 5 days, within about 6 days, within about 1 week, within about 2 weeks, within about 3 weeks, within about 4 weeks, within about 1 month, within about 2 months, within about 3 months, within about 4 months, within about 5 months, within about 6 months, within about 1 year, within about 2 years, or longer, following a stressor and/or administration of the present agent/composition.

Psychiatric evaluations of a patient being treated with the present method can be conducted to determine whether the method is effective. In certain embodiments, the psychiatric evaluation may be carried out before treatment, at the time of treatment, during treatment, and/or after treatment. When the psychiatric evaluation is carried out both before treatment and after (and/or during) treatment with the present method, the results of the evaluation before treatment can provide a baseline for comparison to the results of the evaluation during and/or after treatment. In certain embodiments, psychiatric evaluation is conducted only after treatment.

Psychophysiological stress tests can be performed to measure the amount of stress-induced anxiety present in the various systems of the body (i.e. muscular, cardiovascular, digestive, respiratory and neurological systems). These stress tests are routinely used in the art. Test results are compared to both local and national norms, to determine if the individual is exhibiting an excessive amount of physiological anxiety and whether or not they are able to recover from a standardized stressful stimuli in an appropriate length of time.

Psychiatric testing can be used to monitor a subject to determine the emotional and/or social etiology of the stress disorder. These tests are known in the art and include health-related assessments, mental health assessments, personality tests, and personality type assessment.

In certain embodiments, clinician-administered evaluation and/or self-report instruments are used, with the aim of measuring baseline symptomatology as well as drug actions on (1) the overall severity of the disorder, (2) the core symptoms, and (3) depressed mood.

Non-limiting examples of psychiatric evaluation tools and questionnaires include the following measures.

The Diagnostic and Statistical Manual of Mental Disorders (DSM-5) includes the revised diagnostic criteria for PTSD. See, American Psychiatric Association: Diagnostic and Statistical Manual of Mental Disorders, Fifth Edition. Arlington, Va., American Psychiatric Association, 2013. See also ptsd.va.gov/professional/PTSD-verview/dsm5_criteria_ptsd.asp.

The Structured Clinical Interview for DSM-IV Axis I Disorders, Patient Edition (SCID-P) is a semi-structured interview that provides probe questions as well as follow-up questions to be asked by the clinician to assist in diagnosis. First et al., Structured Clinical Interview for DSM-IV TR Axis I Disorders, Research Version, Patient Edition (SCID-I/P). New York: New York State Psychiatric Institute, Biometrics Research; 2001. It includes an overview to obtain information about demographics, work, chief complaint, history of present illness, past history, treatment history, and current functioning. The main body of SCID-P includes 9 modules that are designed to diagnose 51 mental illnesses in all.

The SCID-P for DSM-5 is the SCID—Patient version, and is the next edition of the SCID modified to incorporate the new DSM-5 criteria.

The Clinician-Administered PTSD Scale (CAPS) is a structured clinical interview designed to assess the essential features of PTSD as defined by the DSM-IV. Weathers et al., Clinician-administered PTSD scale: a review of the first ten years of research. Depress Anxiety. 2001; 13(3):132-156. The CAPS can be used to provide categorical ratings of diagnostic status as well as a quantitative index of symptom severity. Both frequency and intensity scores are derived for each individual symptom. The CAPS total score is based on an individual's response to the 17 items that assess the frequency and intensity of current PTSD symptoms. Subscales of the CAPS are utilized to assess specific symptom clusters. The total score can range from 0 to 136.

The Clinician-Administered PTSD Scale for DSM-5 (CAPS-5) is a 30-item structured interview that can be used to make current (past month) diagnosis of PTSD, make lifetime diagnosis of PTSD, and to assess PTSD symptoms over the past week. CAPS-5 is a 30-item questionnaire, corresponding to the DSM-5 diagnosis for PTSD. The language of the CAPS-5 reflects both changes to existing symptoms and the addition of new symptoms in DSM-5.

Weathers, F. W., et al (2013). The Clinician-Administered PTSD Scale for DSM-5 (CAPS-5).

The Treatment Outcome PTSD Scale (TOP-8) is a brief interviewer-administered scale designed specifically for the assessment of commonly occurring signs and symptoms of PTSD that are subject to change in response to treatment (Davidson, J. R., & Colket, J. T. (1997). The eight-item treatment-outcome post-traumatic stress disorder scale: A brief measure to assess treatment outcome in post-traumatic stress disorder. International Clinical Psychopharmacology, 12(1), 41-45). The TOP-8 is comprised of eight items, each measured on a scale of 0-4, with defined anchors given for each item. The items are representative of the three core features of PTSD with a maximum possible score of 32.

The Hamilton Psychiatric Rating Scale for Anxiety (HAM-A) is a widely used observational rating measure of anxiety severity. The scale consists of 14 items. Each item is rated on a scale of 0 to 4. This scale is administered to assess the severity of anxiety and its improvement during the course of treatment. The HAM-A total score is the sum of the 14 items and the score ranges from 0 to 56. Hamilton M. The Assessment of Anxiety-States by Rating. Br J Med Psychol. 1959; 32(1):50-55.

The Montgomery-Asberg Depression Rating Scale (MADRS) is a 10-item instrument used for the evaluation of depressive symptoms in adults and for the assessment of any changes to those symptoms. Montgomery S. A., et al., A new depression scale designed to be sensitive to change. Br J Psychiatry. 1979 April; 134:382-389. Each of the 10 items is rated on a scale of 0 to 6, with differing descriptors for each item. These individual item scores are added together to form a total score, which can range between 0 and 60 points.

The Young Mania Rating Scale, item 1 (YMRS-1) used to assess mood elevation on the infusion days. Young R C, et al. Rating-Scale for Mania—Reliability, Validity and Sensitivity. Br J Psychiatry. 1978; 133(NOV):429-435.

The Brief Psychiatric Rating Scale (BPRS) is used to assess acute behavioral changes during the infusions. Overall J E et al., The Brief Psychiatric Rating-Scale. Psychol. Rep. 1962; 10(3):799-812 Four key BPRS items for the positive (+) symptoms of psychosis are used: conceptual disorganization, hallucinatory behavior, suspiciousness, and unusual thought content. Three items representing the negative (−) symptoms of psychosis will also be used: blunted affect, emotional withdrawal, and motor retardation.

The Clinician-Administered Dissociative States Scale (CADSS) is used to measure dissociative effects during the infusions. Bremner J D, et al., Measurement of Dissociative States with the Clinician-Administered Dissociative States Scale (CADSS). J Trauma Stress. 1998; 11(1):125-136 The scale includes 19 questions and 8 observer ratings scored from 0 (not at all) to 4 (extremely). The CADSS measures impairment in body perception, environmental perception, time perception, memory impairment, and feelings of unreality.

The Patient Rating Inventory of Side Effects (PRISE) is a patient self-report used to qualify side effects by identifying and evaluating the tolerability of each symptom. Levine J, Schooler N R. SAFTEE: A technique for the systematic assessment of side effects in clinical trials. Psychopharmacol Bull. 1986; 22(2):343-381.

The Clinical Global Impression (CGI) scale assesses treatment response in psychiatric patients. The administration time is 2 minutes. This scale consists of three items: Severity of Illness (item 1); Global Improvement (item 2); and Efficacy Index (item 3). Item 1 is rated on a seven-point scale (1=normal, 7=among the most extremely ill patients) as is item 2 (1=very much improved, 7=very much worse). Each includes an additional response of "not assessed." Item 3 is rated on a four-point scale (from "none" to "outweighs therapeutic effect").

The Impact of Events Scale (IES) is one of the most widely used self-report measures of stress reactions to traumatic events. Horowitz et al., Impact of Event Scale: a measure of subjective stress. Psychosom Med. 1979 May; 41(3):209-218. See also, Weiss et al., The Impact of Event Scale—Revised In: Wilson J, Keane T M, eds. Assessing psychological trauma and PTSD. New York: Guilford; 1996: 399-411. It measures both intrusion and avoidance. Sundin et al., Impact of Event Scale: psychometric properties. Br J Psychiatry. 2002 March; 180:205-209. Joseph S. Psychometric evaluation of Horowitz's Impact of Event Scale: a review. J Trauma Stress. 2000 January; 13(1):101-113. The total score can range from 0 to 75.

The Posttraumatic Stress Disorder Checklist (PCL-5) is a 17-item self-report measure reflecting DSM-5 symptoms of PTSD. The PCL-5 measures symptoms in response to stressful situations (Weathers, F., et al. (1993). The PTSD checklist (PCL): Reliability, validity, and diagnostic utility. Annual Convention of the International Society for Traumatic Stress Studies, San Antonio, Tex.).

The Quick Inventory of Depressive Symptomatology, Self Report (QIDS-SR) is a 16-item self-rated instrument designed to assess the severity of depressive symptoms present in the past seven days. Rush A J, Trivedi M H, Ibrahim H M et al. The 16-Item quick inventory of depressive symptomatology (QIDS), clinician rating (QIDS-C), and self-report (QIDS-SR): a psychometric evaluation in patients with chronic major depression. Biol. Psychiatry. 2003; 54(5):573-583. The 16 items cover the nine symptom domains of major depression, and are rated on a scale of 0-3. Total score ranges from 0 to 27, with ranges of 0-5 (normal), 6-10 (mild), 11-15 (moderate), 16-20 (moderate to severe), and 21+(severe).

The Childhood Trauma Questionnaire (CTQ) is a 28-item self-report instrument that assesses childhood trauma in the following areas: physical, sexual and emotional abuse and physical and emotional neglect. Bernstein D P, Stein J A, Newcomb M D et al. Development and validation of a brief screening version of the Childhood Trauma Questionnaire. Child Abuse Negl. 2003 February; 27(2):169-190. Each item is rated on a scale of 1 (never true) to 5 (very often true). The κ subscales are then totaled, with scores ranging from 5-25 for each traumatic category.

Visual Analogue Scales (VAS) are used to assess subjective state changes. Bond A, Lader M. The use of analogue scales in rating subjective feelings. Br J Med Psychol. 1974; 47(3):211-218. They are 100-mm horizontal lines marked proportionately to the perceived intensity of the subjective experience (0=not at all, to 10=extremely) for the following states: anxious, depressed, drowsy, high, hungry, and nauseous.

The Sheehan Disability Scale (SDS) is a self-report disability measure. It has demonstrated sensitivity to impairment and changes as a result of treatment across a wide range of psychiatric disorders. The SDS asks only about current levels of impairment, providing no indication of whether the person has done better or worse in the past, thus making it a reasonable short-term outcome measure that is un-confounded by historical impressions. The dependent variable is the total score, which is based on the sum of three 10-point items (work, social life, and family life), with higher scores reflecting greater disability. Sheehan D. The Anxiety Disease. New York, N.Y.: Scribner; 1983.

The Wechsler Abbreviated Scale of Intelligence 2-Subtest (WAS1-2) is a reliable brief measure of IQ for 6 to 89 year-olds that includes Vocabulary (an estimate of verbal fluid abilities) and Matrix Reasoning (an estimate of non-verbal fluid abilities). Wechsler D. Wechsler Abbreviated Scale of Intelligence San Antonio, Tex.: Psychological Corporation; 1999. It is extensively used in clinical, educational, and research settings. Average reliability coefficient is 0.96 and test-retest reliability is 0.88.

The Hopkins Verbal Learning Test (HVLT) is a repeatable test of memory acquisition and delayed recall of words. Subjects are presented with the same 12-item list for 3 learning trials and asked each time to repeat the items on each list. Delayed recall and recognition conditions are administered later. Dependent variables used in this study include total learning over the 3 trials (for the acquisition variable) and total delayed recall score (for the recall component). Brandt J, Benedict R. Hopkins Verbal Learning Test, Revised. Odessa, Fla.: Psychological Assessment Resources; 1997.

The Profile of Mood States-Bipolar (POMS-Bi) scale measures moods and feelings primarily in clinical rather than nonclinical settings. It can help to determine an individual's psychiatric status for therapy, or be used to compare mood profiles associated with various personality disorders. It is also a useful instrument in identifying the effects of drug treatments.

The Post-Traumatic Cognitions Inventory (PTCI) is a 33-item scale, which is rated on a Likert-type scale ranging from 1 (totally disagree) to 7 (totally agree). Scale scores are formed for the three subscales, which show a high degree of intercorrelation (rs=0.57-0.75).

The New Cognitions scale is a 6-item pilot scale, which is rated on a Likert-type scale ranging from 1 (not at all) to 4 (a lot). The scale is based on the Post Traumatic Growth Inventory (PTGI) from which items have been directly selected (new items were added to the scale as well), and on the Brief-COPE (see Carver, C. S. (1997) "You want to measure coping but your protocol's too long: Consider the brief COPE." International Journal of Behavioral Medicine 4; 92-100).

The Medical Outcomes Study (MOS) Social Support Survey is a 19-item self-report measure designed to assess levels of functional social support. The MOS-SS has two subscales (emotional and instrumental social support) to identify potential social support deficits (Sherbourne, C. D. & Stewart, A. L. (1991). "The MOS Social Support Survey." Soc Sci Med 32(6): 705-714).

The Purpose in Life test-Short Form (PIL-SF) is a brief, 4-item form of the 20-item Purpose in Life test. This scale asks respondents to report to what extent they have achieved their goals in life, and to what extent they perceive their life to be meaningful or purposeful. (Schulenberg et al 2010; Psychotherapy (Chic). 2008 December; 45(4):447-63).

Posttraumatic Growth Inventory (PTGI)-Short Version is a 10-item shortened version of the PTGI self-report questionnaire (ref). It asks respondents to rate the extent to which they have changed as the result of experiencing a highly stressful life event. Items span positive changes in five domains: relating to others, new possibilities, personal strength, spiritual change, and appreciation of life (Cann, A., et al. (2010). A short form of the Posttraumatic Growth Inventory. Anxiety, Stress & Coping, 23, 127-137).

The Quality of Life Enjoyment and Satisfaction Questionnaire (Q-LES-Q) is a self-report scale measuring the degree of enjoyment and satisfaction experienced by subjects in various areas of daily functioning. The summary scores are reliable and valid measures of these dimensions in a group of depressed subjects (Endicott J, et al. Quality of Life Enjoyment and Satisfaction Questionnaire: A New Measure. Psychopharmacology Bulletin; 1993; 29:321-326).

In certain embodiments, self-evaluation of the subject being treated is conducted.

Pharmaceutical Compositions

While it is possible that the present a compound, as well as salts, solvates and physiological functional derivatives thereof, may be administered as the raw chemical, it is possible to present the active ingredient as a pharmaceutical composition. Accordingly, the invention further provides a pharmaceutical composition, which comprises the present compound and/or salts, solvates and physiological functional derivatives thereof, and one or more pharmaceutically acceptable carriers, diluents, or excipients. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical composition including admixing the present compound, or salts, solvates and physiological functional derivatives thereof, with one or more pharmaceutically acceptable carriers, diluents or excipients.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing compound 20, and pharmaceutically acceptable excipients.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

As used herein, the phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopeias for use in animals, and more particularly in humans.

Pharmaceutical compositions of the present invention may be presented in unit dose forms containing a predetermined amount of active ingredient per unit dose. Such a unit may contain, for example, 5 µg to 1 g, preferably 1 mg to 700 mg, more preferably 5 mg to 100 mg of the present compound, depending on the condition being treated, the route of administration and the age, weight and condition of the patient. Such unit doses may therefore be administered more than once a day. Preferred unit dosage compositions are those containing a daily dose or sub-dose (for administration more than once a day), as herein above recited, or an appropriate fraction thereof, of an active ingredient. Furthermore, such pharmaceutical compositions may be prepared by any of the methods well known in the pharmacy art.

Pharmaceutical compositions of the present invention may be adapted for administration by any appropriate route, for example by the oral (including buccal or sublingual), inhaled, nasal, ocular, or parenteral (including intravenous and intramuscular) route. The present composition may be injected. Such compositions may be prepared by any method known in the art of pharmacy, for example by bringing into association the active ingredient with the carrier(s) or excipient(s).

In a further embodiment, the present invention provides a pharmaceutical composition adapted for administration by the oral route, the treatment of stress-induced affective disorder.

Pharmaceutical compositions of the present invention which are adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

It should be understood that, in addition to the ingredients particularly mentioned above, the compositions may include other agents conventional in the art having regard to the type of formulation in question, for example those suitable for oral administration may include flavoring agents.

A therapeutically effective amount of a compound of the present invention will depend upon a number of factors including, for example, the age and weight of the subject, the precise condition requiring treatment and its severity, the nature of the formulation, and the route of administration, and will ultimately be at the discretion of the attendant physician or veterinarian.

Kits

Also provided are kits for use in the present methods of prophylactically treating a stress-induced affective disorder.

The kits can include a compound or composition provided herein, and instructions providing information to a health care provider regarding usage in accordance with the present methods. The kit may optionally contain a second agent or composition. Instructions may be provided in printed form or in the form of an electronic medium such as a floppy disc, CD, or DVD, or in the form of a website address where such instructions may be obtained. A unit dose of a compound or composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition. In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like.

The kits described herein contain one or more containers, which contain compounds, signaling entities, biomolecules and/or particles as described. The kits also contain instructions for mixing, diluting, and/or administrating the compounds. The kits also include other containers with one or more solvents, surfactants, preservative and/or diluents (e.g., saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the compound and the mode of use or administration. Suitable solvents for drug compositions are well known and are available in the literature. The solvent will depend on the compound and the mode of use or administration.

The kits comprise a carrier being compartmentalized to receive in close confinement one or more container such as vials, tubes, and the like, each of the container comprising one of the separate elements to be used in the method. For example, one of the container may comprise a positive control in an assay. Additionally, the kit may include containers for other components, for example, buffers useful in the assay.

This invention will be better understood from the Examples, which follow. However, one skilled in the art will readily appreciate that the specific methods and results discussed are merely illustrative of the invention as described more fully in the claims that follow thereafter.

Example 1 Ovarian-Derived Hormones Causally Contribute to the Prophylactic Efficacy of (R,S)-Ketamine and (2R,6R)-Hydroxynorketamine in Female Mice Females are more likely than males to develop major depressive disorder (MDD) after exposure to stress. We previously reported that the administration of (R,S)-ketamine before stress can prevent depressive-like behavior in male mice but have yet to assess efficacy in female mice or for other compounds. The goal of this study was to test the prophylactic potential of ketamine and its metabolites in females. We administered (R,S)-ketamine or its metabolites (2R,6R)-hydroxynorketamine ((2R,6R)-HNK) and (2S,6S)-HNK at various doses 1 week before one of a number of stressors, including contextual fear conditioning (CFC), learned helplessness (LH), and chronic immobilization stress (CIS), in female 129S6/SvEv mice. Prophylactic efficacy was validated using the forced swim test (FST). To examine the interaction between ovarian hormones and stress resilience, female mice also underwent ovariectomy surgery (OVX) and a hormone replacement protocol prior to drug administration. (R,S)-ketamine and (2R,6R)-HNK, but not (2S,6S)-HNK, significantly reduced stress-induced depressive-like behavior in females. (R,S)-ketamine was prophylactically effective at a lower dose (10 mg/kg) in females than in males (30 mg/kg). Moreover, ovarian-derived hormones were necessary and sufficient for prophylaxis. Our results suggest that prophylactics against stress-induced depressive-like behavior can be developed in a sex-specific manner and that ovarian hormones mediate prophylactic efficacy. To our knowledge, this is the first demonstration of the prophylactic efficacy of (2R,6R)-HNK and of pharmacologically enhanced stress resilience in females.

Here, we investigated whether prophylactics could be developed for use in female mice and whether ketamine metabolites could have the same prophylactic efficacy as their precursor. Female 129S6/SvEv mice were administered a single injection of saline, (R,S)-ketamine, (2R,6R)-HNK, or (2S,6S)-HNK 1 week before one of many stressors including CFC, LH, or CIS. None of the prophylactic compounds tested attenuated learned fear in females. However, prophylactic (R,S)-ketamine and (2R,6R)-HNK, but not (2S,6S)-HNK, significantly decreased stress-induced depressive-like behavior. Ovarian hormones were both necessary and sufficient for the prophylactic efficacy of both drugs. These data show that prophylactics against depressive-like behavior can be developed for use in females and emphasize the need for sex-specific approaches to the prevention and treatment of psychiatric disorders in future studies.

Methods and Materials

Mice

Female 129S6/SvEvTac mice were purchased from Taconic (Hudson, N.Y.) at 7 weeks of age. Mice were housed 5 per cage in a 12-h (06:00-18:00) light-dark colony room at 22° C. Food and water were provided ad libitum. Behavioral testing was performed during the light phase. All experiments were approved by the Institutional Animal Care and Use Committee (IACUC) at the New York Psychiatric Institute (NYSPI).

Drugs

A single injection of saline (0.9% NaCl), (R,S)-ketamine (Ketaset III, Ketamine HCl injection, Fort Dodge Animal Health, Fort Dodge, Iowa), (2R,6R)-HNK (Organic Chemistry Collaborative Center (OCCC) at Columbia University), or (2S,6S)-HNK (OCCC) was administered once during the course of each experiment at approximately 8 weeks of age. (R,S)-ketamine, (2R,6R)-HNK, and (2S,6S)-HNK were prepared in physiological saline and all injections were administered intraperitoneally (i.p.) in volumes of 0.1 cc per 10 mg body weight.

Ovariectomy (OVX)

Surgery was performed as previously described (26). Briefly, mice were anesthetized with 1.5% isoflurane in an $O_2/N_2O$ (30%/70%) mixture and placed on a T/Pump heating pad (Stryker, Kalamazoo, Mich.). A dorsal 3×3 cm area was shaved and disinfected with Betadine and alcohol before making a 2-cm midline incision. Ovarian and surrounding adipose tissue were bilaterally cut and cauterized. The fascia was closed with Coated VICRYL© Sutures (Johnson & Johnson, New Brunswick, N.J.), and the skin was closed with 7 mm wound clips (Braintree Scientific, Braintree, Mass.). The closed incision was treated with a 5% topical lidocaine gel (ESBA Laboratories, Jupiter, Fla.). Mice were then administered subcutaneous Carprofen (5 mg/kg) and allowed to recover 10 days before behavioral testing.

Hormone Replacement

Silastic estrogen capsules were prepared and implanted as previously described (27). Two cm lengths of silastic tubing (Dow Corning, Midland, Mich.) were cut and filled with a 2 mg/ml solution of 17β-estradiol (Sigma Aldrich, St. Louis, Mo.) dissolved in sesame oil (Sigma Aldrich, St. Louis, Mo.). As controls, vehicle implants were filled with sesame oil alone. Implants were sealed with silicone sealant (Dap Products, Baltimore, Md.) and subcutaneously implanted. A 2×2 cm area along the dorsal aspect of the neck was shaved and disinfected with Betadine and alcohol before making a 2 mm incision in the skin. A small subcutaneous pocket was gently created, and the implant was placed vertically along the body. The incision was then closed with sutures (Johnson & Johnson, New Brunswick, N.J.) and treated with 5% topical lidocaine gel. Mice were administered subcutaneous Carprofen (5 mg/kg) and allowed to recover for 10 days before behavioral testing.

Statistical Analysis

All data were analyzed using StatView 5.0 (SAS Institute, Cary, N.C.) or Prism 7.0 (Graphpad Software, La Jolla, Calif.). Alpha was set to 0.05 for all analyses. Generally, the effect of Drug or Group was analyzed using an analysis of variance (ANOVA), using repeated measures where appropriate. Post-hoc Fisher's Least Significant Difference (LSD) and Dunnett tests, to correct for multiple comparisons, were used where appropriate. All statistical tests and p values are listed in Tables 1-1 to 1-10. Experimental n are listed in Table 2. A summary of all behavioral tests is listed in Table 3.

All behavioral tests were performed as follows.

Contextual Fear Conditioning (CFC)

A 3-shock CFC paradigm was administered as previously described (52-53). All sessions were scored for freezing using FreezeFrame4.

Chronic Immobilization Stress (CIS)

The CIS procedure induces a depressive-like phenotype in test subjects and has both predictive and face validity (54). Here, we used an adapted protocol from Ramirez et al. (55).

Learned Helplessness (LH)

In the LH protocol, mice are exposed to unpredictable and uncontrollable stress (shocks) and develop coping deficits to deal with inescapable shocks. The LH paradigm was administered as previously described (56).

Forced Swim Test (FST)

A FST paradigm was administered as previously described (56).

Tail Immersion (TI) Test

The TI test was administered as previously described (57). Compared to other nociceptive tests, TI provides reliable results across and within subjects (57). Prior to testing, mice were habituated to a restraint apparatus for 5 days, which consisted of a Falcon tube through which was drilled 10 air holes of 2 mm in diameter (Fisher Scientific, Pittsburgh, Pa.). During the test, 50 mL of water was heated to 52° C. Mice were immobilized in the tube with their tail hanging freely before dipping the last two-thirds of the tail into the hot water. Tail withdrawal latency was measured in seconds using a stopwatch. Mice were tested in 3 consecutive trials and the average across all trials was used for analysis.

Elevated Plus Maze (EPM)

The EPM was administered as previously described (58), with the exception that videos were scored using ANY-maze behavioral tracking software (Stoelting Co., Wood Dale, Ill.).

Open Field (OF)

The OF assay was administered as previously described (59).

Results (R,S)-Ketamine and (2R,6R)-HNK, but not (2S,6S)-HNK, are Prophylactic Against Stress-Induced Depressive-Like Behavior in Female Mice Female 129S6/SvEv mice were administered a single injection of saline, (R,S)-ketamine (2.5 mg/kg, 10 mg/kg, or 30 mg/kg), or (2R,6R)-HNK (0.025 mg/kg, 0.075 mg/kg, 0.1 mg/kg, 0.3 mg/kg, 2.5 mg/kg, 10 mg/kg, 30 mg/kg) (FIG. 1A). After one week, mice were subjected to 3-shock CFC. Five days later, mice were placed back in the aversive CFC context and then administered 2 consecutive days of the FST.

Figure 6F:
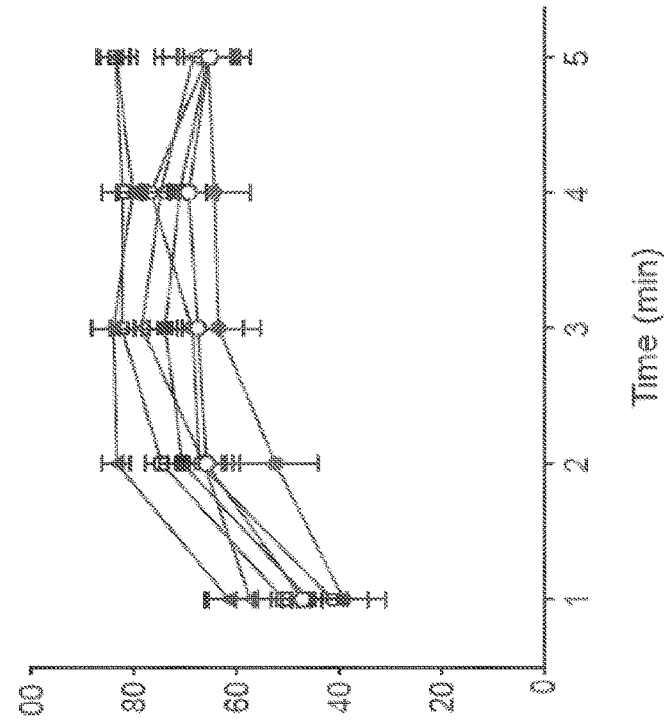
Figure 6E:
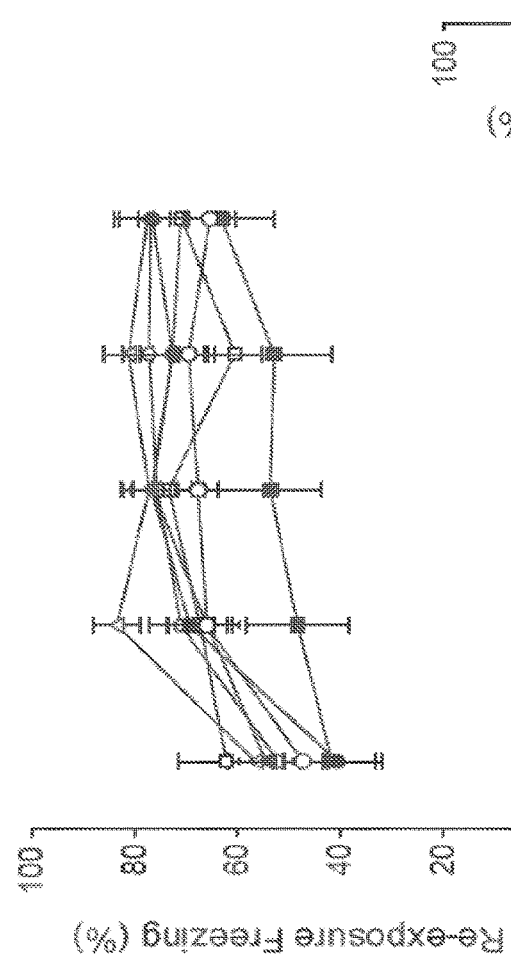

We have recently shown that a single injection of (R,S)-ketamine given 1 week prior to CFC training can attenuate learned fear during contextual re-exposure in male mice (21). Here, prophylactic administration of (R,S)-ketamine did not alter fear encoding or fear retrieval in females (FIGS. 6A-6C). During re-exposure, freezing behavior was comparable across all groups (FIGS. 1B-1D, FIGS. 6D-6F). These data indicate that prophylactic (R,S)-ketamine and its metabolites do not attenuate learned fear in female mice as previously reported in male mice.

The FST is a behavioral assay that is broadly considered to have predictive validity when quantifying antidepressant efficacy (27). On FST Day 2, prophylactic (R,S)-ketamine (10 mg/kg) and (2R,6R)-HNK (0.025 mg/kg) significantly reduced immobility time when compared to saline. However, immobility time in all other experimental groups was not altered (FIGS. 1E-1G). These data indicate that female mice require a lower concentration of (R,S)-ketamine to elicit ketamine's protective effects and that (2R,6R)-HNK, but not its enantiomer (2S,6S)-HNK, is prophylactic against depressive-like behavior induced by CFC stress.

Mice were then assayed in the open field (OF) and tail immobilization (TI) test to determine if prophylactic ketamine resulted in anxiolytic or nociceptive effects, respectively, in female mice. There were no significant changes in total distance traveled in the OF, time spend in the OF center, or in tail withdrawal latency across all groups (FIGS. 1H-1J). Therefore, the decreased immobility time in the FST is most likely not confounded by nonspecific effects on locomotion or nociception.

Figure 2A:
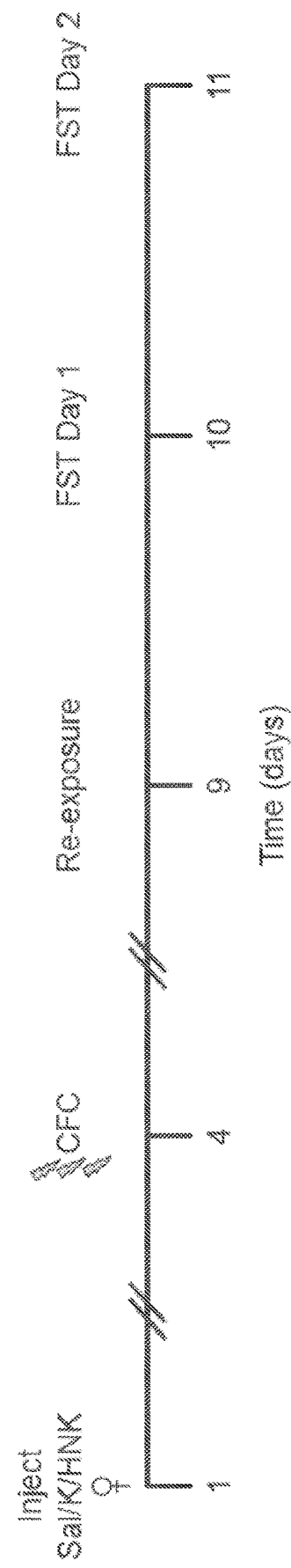
FIGS. 2A-2F. (2R,6R)-HNK, but not (R, S)-ketamine, acts prophylactically to prevent stress-induced depressive-like behavior when administered 3 days, but not 24 hours, before stress. (A) Experimental design. (B), (C) On FST Day 2, (2R,6R)-HNK (0.025 mg/kg), but not (R,S)-ketamine significantly reduced immobility compared to control saline groups. Average immobility time was averaged over the last 4 minutes of the test. (D) Experimental design. (E), (F) (2R,6R)-HNK (0.025 mg/kg) did not alter immobility in the FST when compared to saline. Average immobility time was averaged over the last 4 minutes of the test. (n=5-10 mice per group). Error bars represent ±SEM.  $p<0.01$. * $p<0.0001$. Sal, Saline; K, ketamine; HNK, hydroxynorketamine; CFC, contextual fear conditioning; FST, forced swim test; sec, seconds; min, minutes.

(2R,6R)-HNK, but not (R,S)-Ketamine, is Prophylactic Over a Shorter Time Interval in Female Mice Next, we sought to determine if either compound could act prophylactically when given over a smaller time interval before stress (FIG. 2A). We previously reported that (R,S)-ketamine attenuates learned fear when administered 1 week, but not 1 day or 1 month before stress in male mice (19). Here, saline, (R,S)-ketamine (2.5 mg/kg, 10 mg/kg, and 30 mg/kg), or (2R,6R)-HNK (0.025 mg/kg) was administered 3 days, instead of 1 week, before CFC in female mice.

Figure 2C:
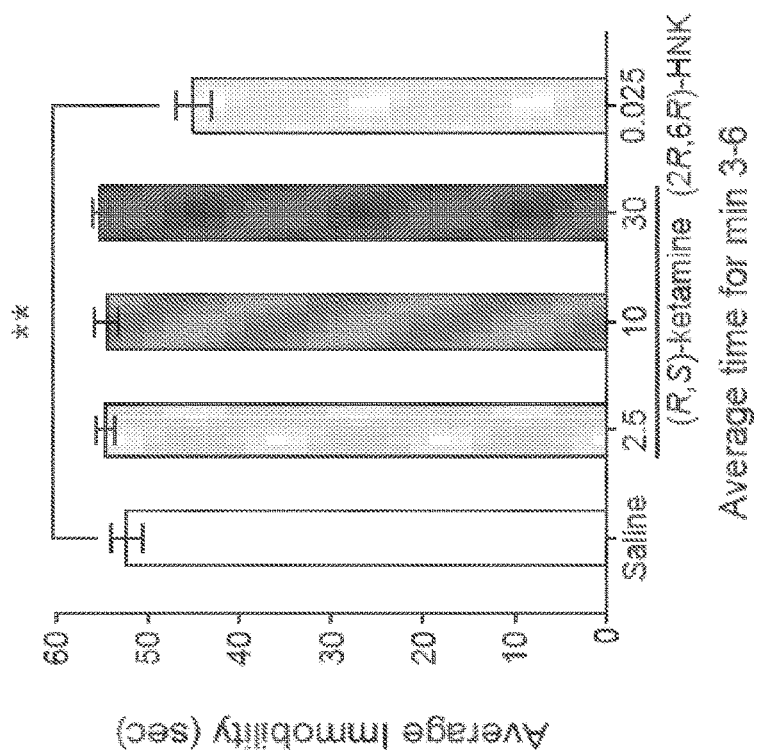
Figure 2B:
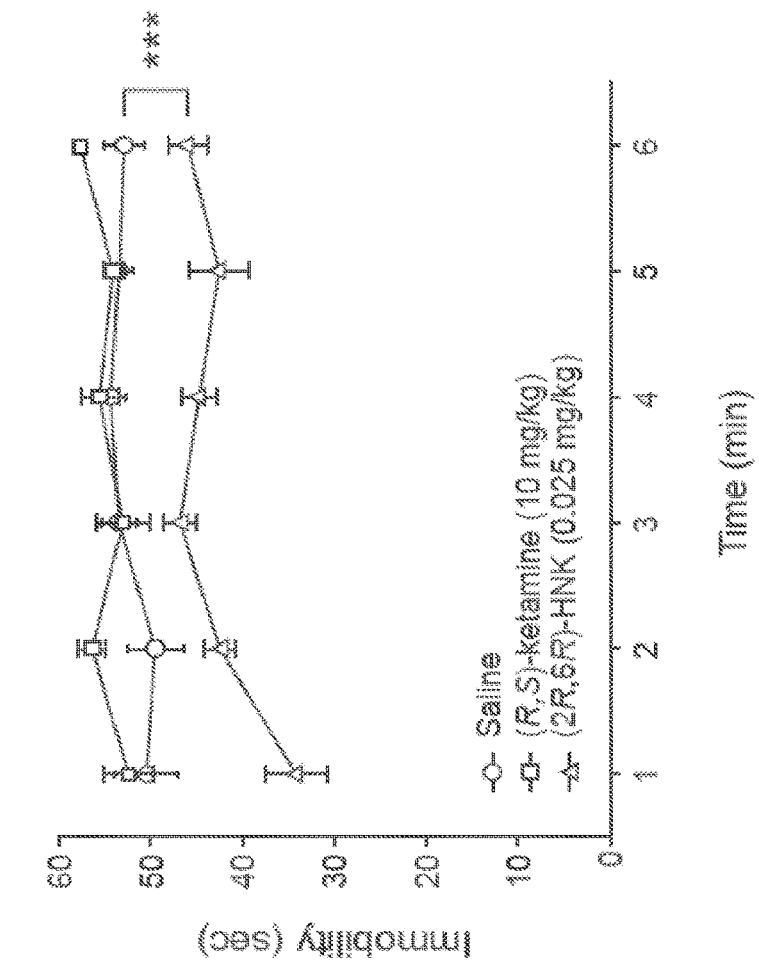
Figure 7C:
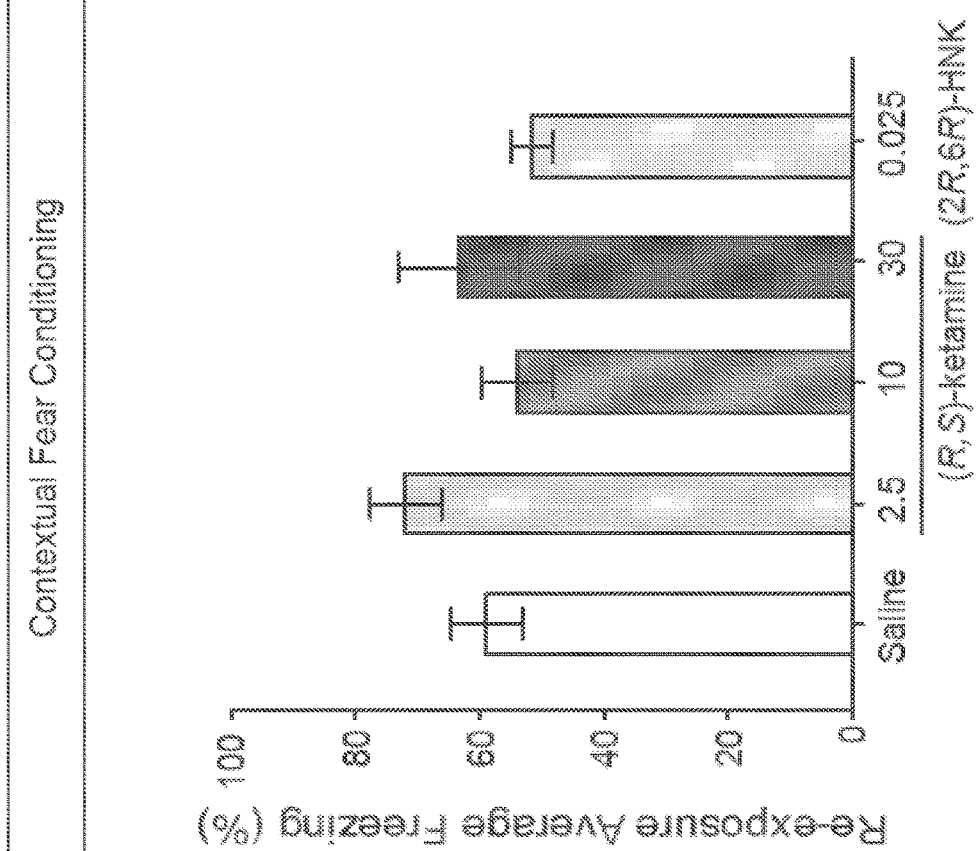

During CFC training, (R,S)-ketamine (2.5 mg/kg, 10 mg/kg), but no other drug groups, significantly increased freezing compared to saline (FIG. 7A). During context re-exposure, all groups froze at comparable levels (FIGS. 7B-7C). These data suggest that (R,S)-ketamine and (2R,6R)-HNK do not affect freezing during re-exposure when given 3 days before a stressor. On FST Day 2, only (2R,6R)-HNK mice displayed decreased immobility, indicating that (2R,6R)-HNK, but not (R,S)-ketamine, administered 3 days before CFC can prevent stress-induced depressive-like behavior in female mice (FIGS. 2B-2C).

Figure 2D:
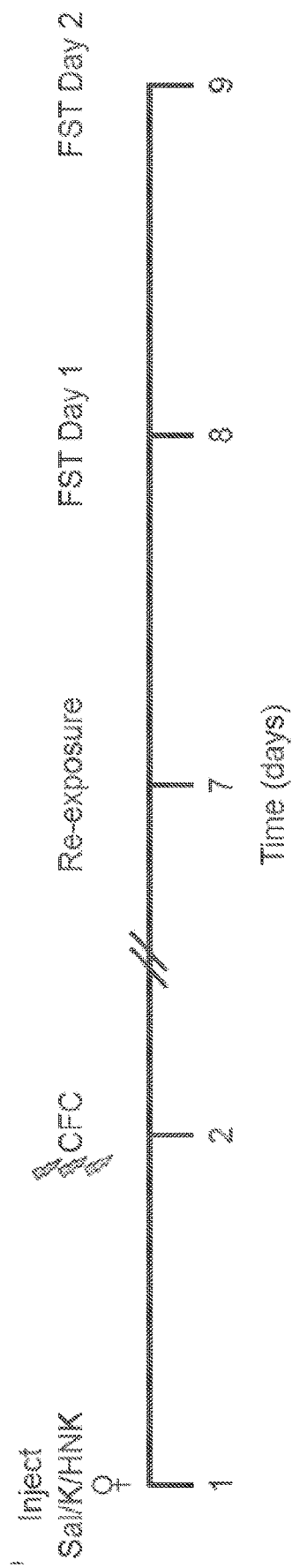
Figure 2F:
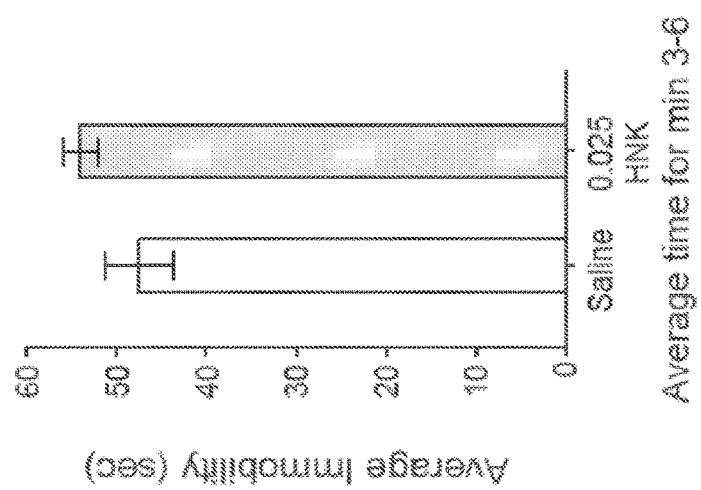
Figure 2E:
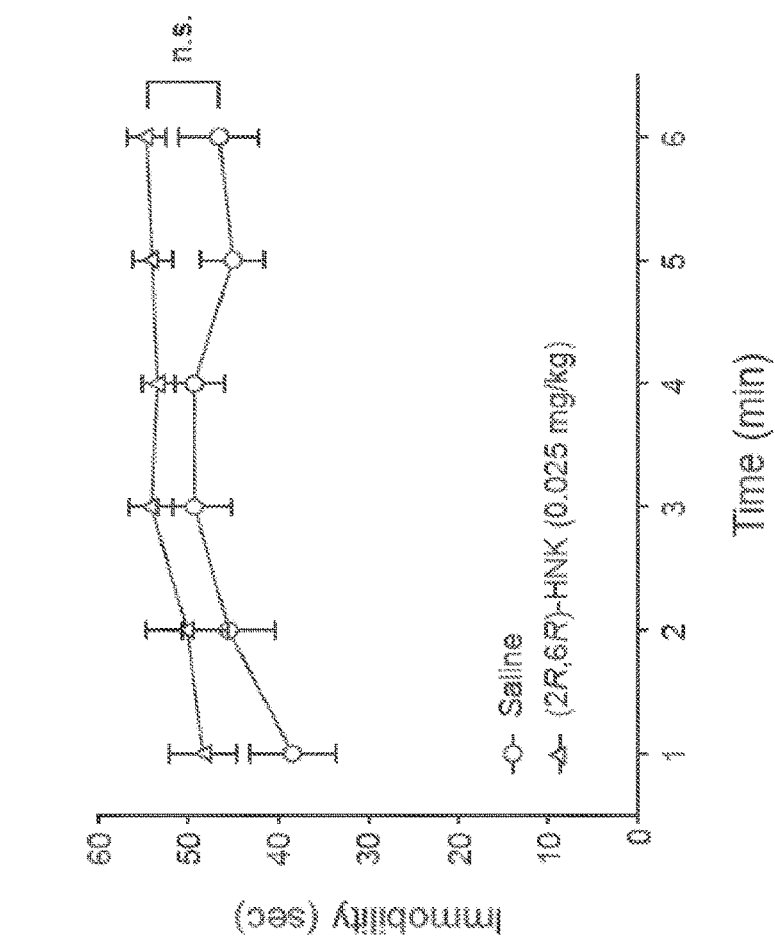
Figure 7E:
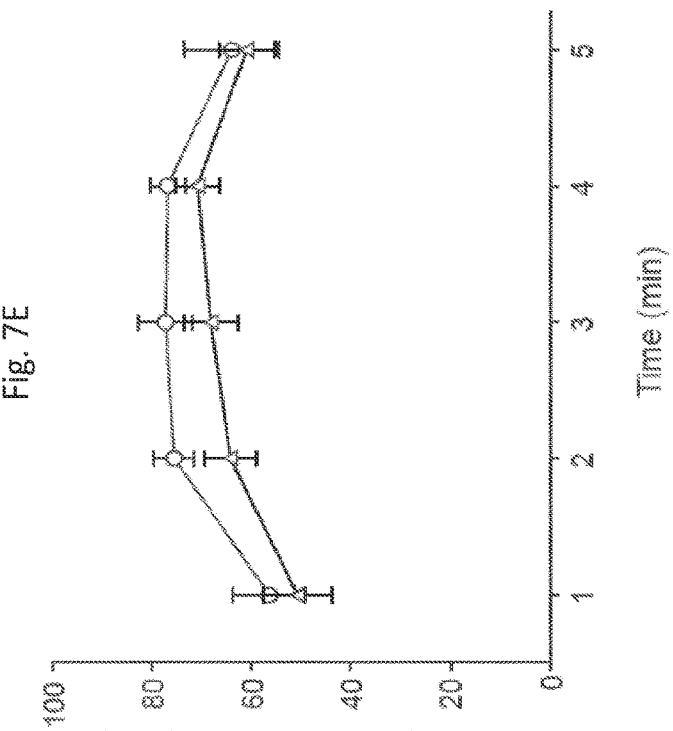
Figure 7D:
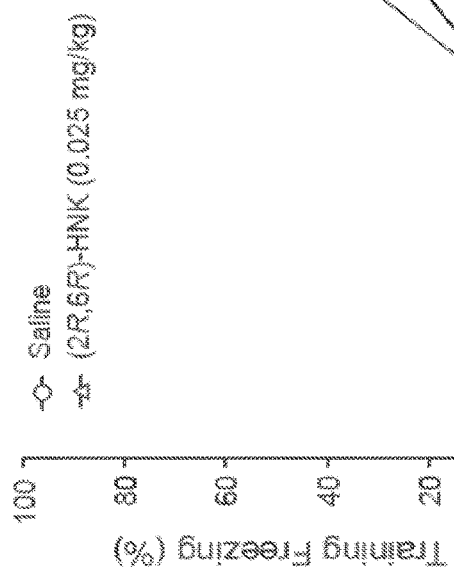
Figure 7F:
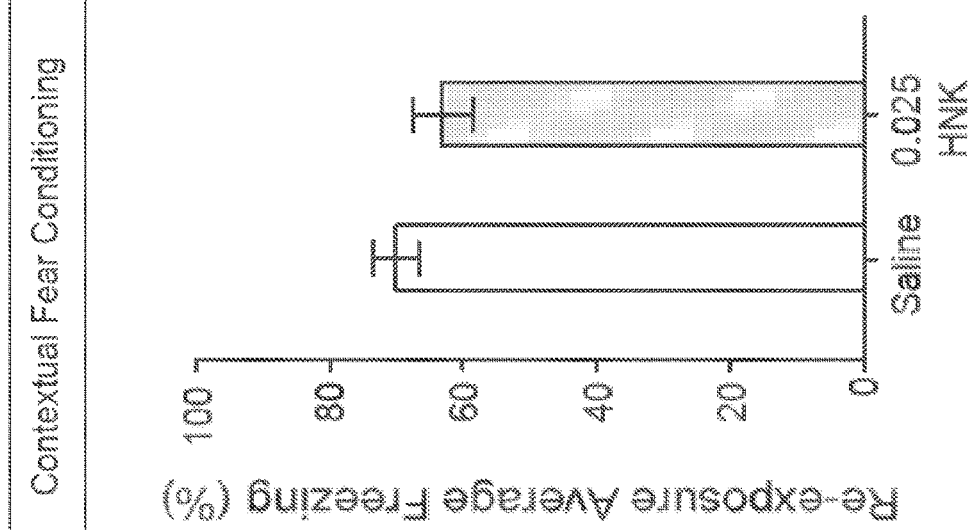

To determine if the onset of efficacy could be even shorter, we then administered (2R,6R)-HNK 24 hours before exposing mice to CFC (FIG. 2D). During training and re-exposure, both groups showed comparable levels of freezing (FIGS. 7D-7F). On Day 2 of the FST, both groups had comparable levels of immobility time (FIGS. 2F-2E). These results demonstrate that (2R,6R)-HNK is not prophylactically effective when administered 24 h before a stressor, providing further evidence that prophylactic ketamine and (2R,6R)-HNK are only efficacious within a specific time window.

(R,S)-Ketamine and (2R,6R)-HNK are Prophylactic Against CIS in Female Mice

Figure 3A:
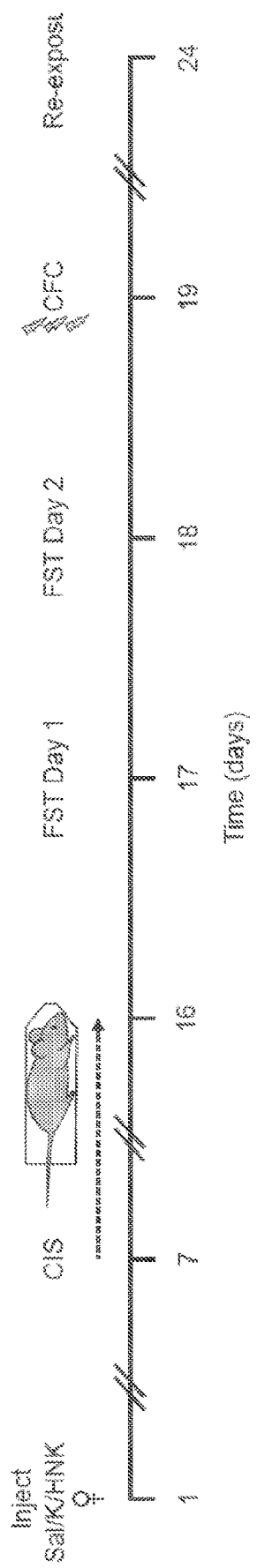

As previously tested in male mice (18), we validated our findings in a model of chronic stress. Mice were administered saline, (R,S)-ketamine (10 mg/kg), or (2R,6R)-HNK (0.025 mg/kg) (FIG. 3A). Drug dosages were chosen based on results from FIG. 1 and used for the remainder of the project unless otherwise specified. One week later, a 10-day CIS protocol was administered. Subsequently, mice were tested in the FST.

Figure 3C:
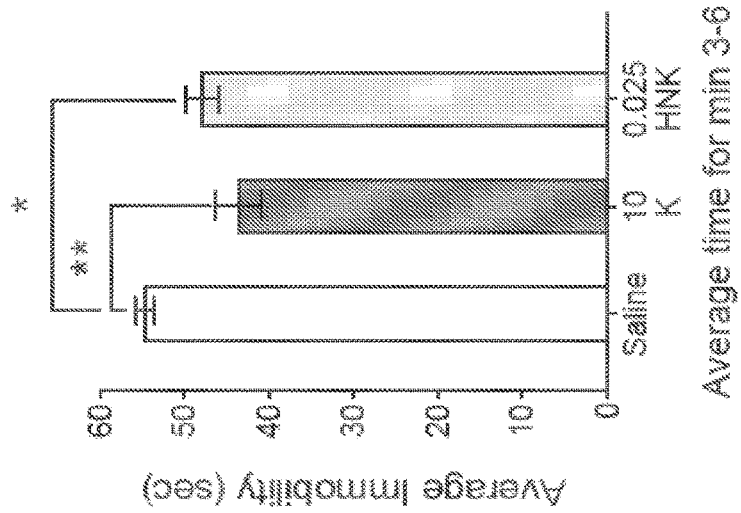
Figure 3B:
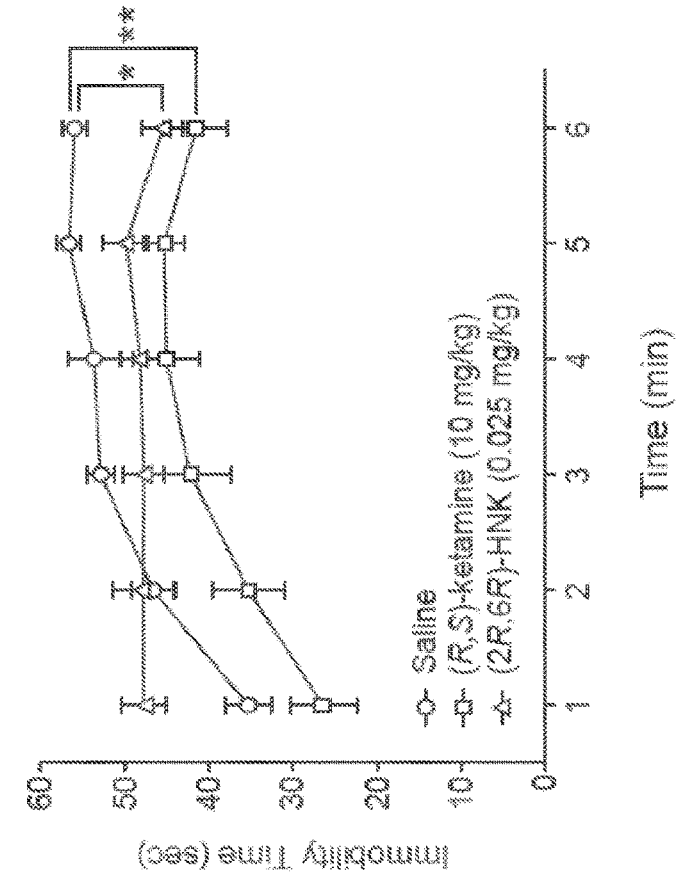

On FST Day 2, both prophylactic drugs significantly lowered immobility when compared to saline, indicating that both (R,S)-ketamine and (2R,6R)-HNK are prophylactic against stress-induced depressive-like behavior in a chronic stress model (FIGS. 3B-3C). These data indicate that prophylactic (R,S)-ketamine and (2R,6R)-HNK are sufficient to protect against the onset of depressive-like behavior following a chronic stress model. In both CFC training and re-exposure sessions, freezing behavior was comparable across all groups, indicating that prophylactic ketamine and (2R,6R)-HNK can protect against depressive-like behavior induced by stress but do not affect fear behavior (FIGS. 3D-3F).

Figure 4A:
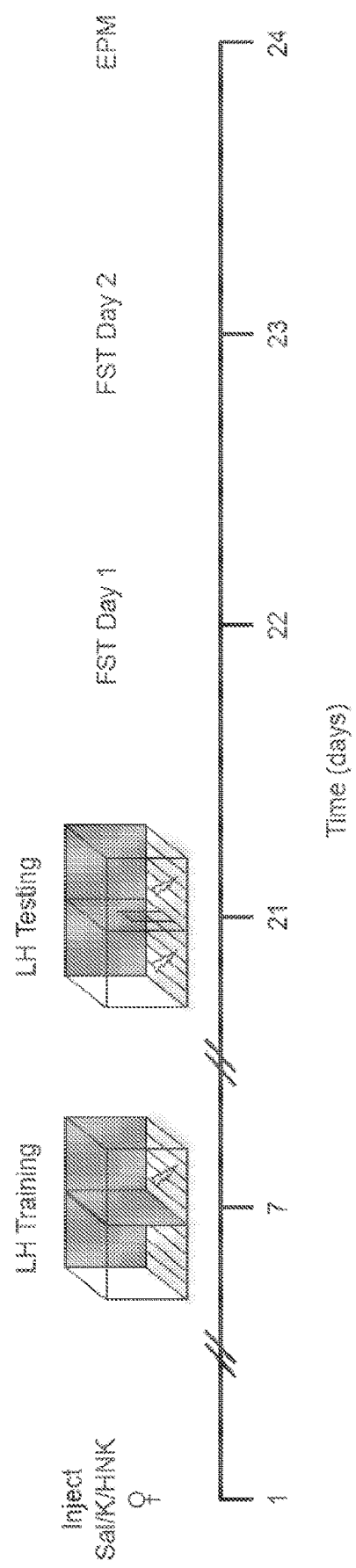

(R,S)-Ketamine and (2R,6R)-HNK Prevent LH-Induced Depressive-Like Behavior in Female Mice We have previously shown that prophylactic (R,S)-ketamine attenuates helpless behavior in male mice (18). To validate these findings in females, female mice were administered saline, (R,S)-ketamine, or (2R,6R)-HNK one week prior to LH training (FIG. 4A). Two weeks later, mice were tested for escape latency and for depressive- and anxiety-like behaviors in the FST and elevated plus maze (EPM). CFC was again administered following these behavioral assays.

Figures 4E, 4F:
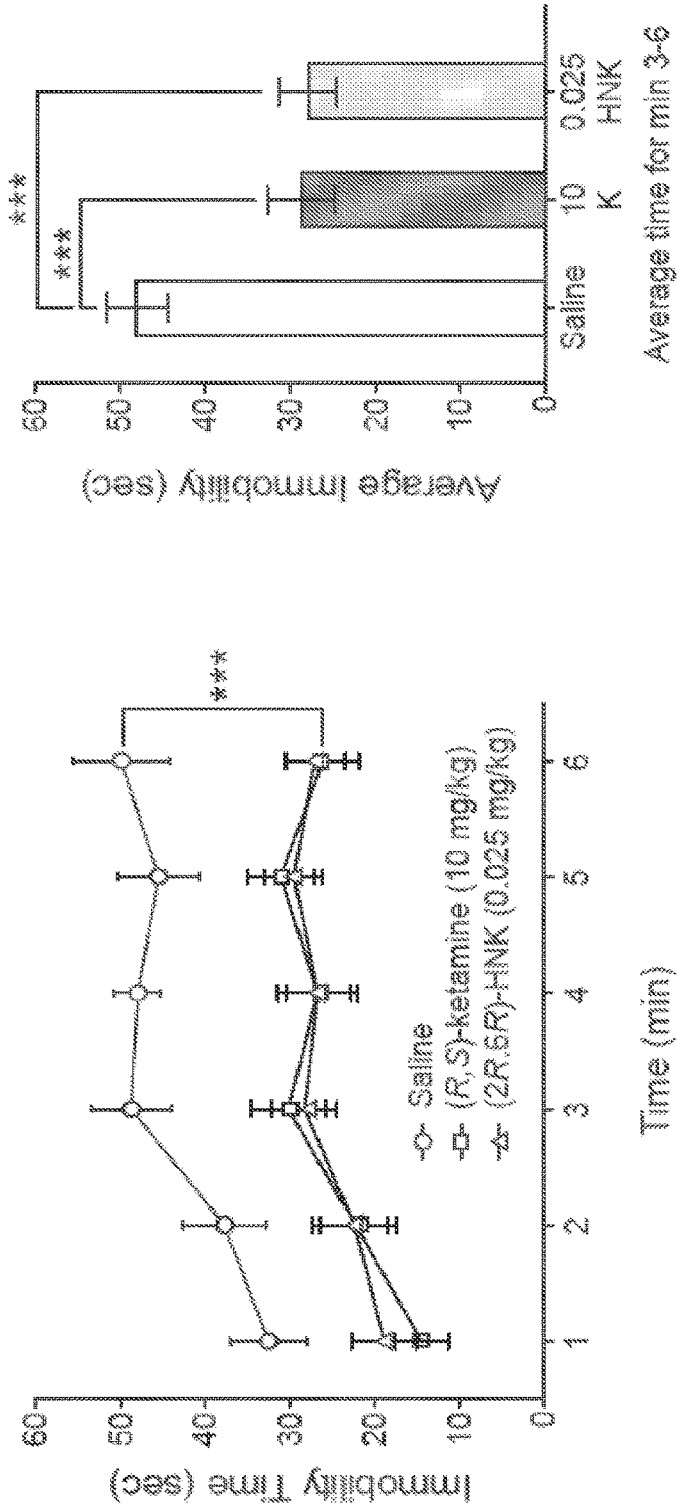
Figure 8D:
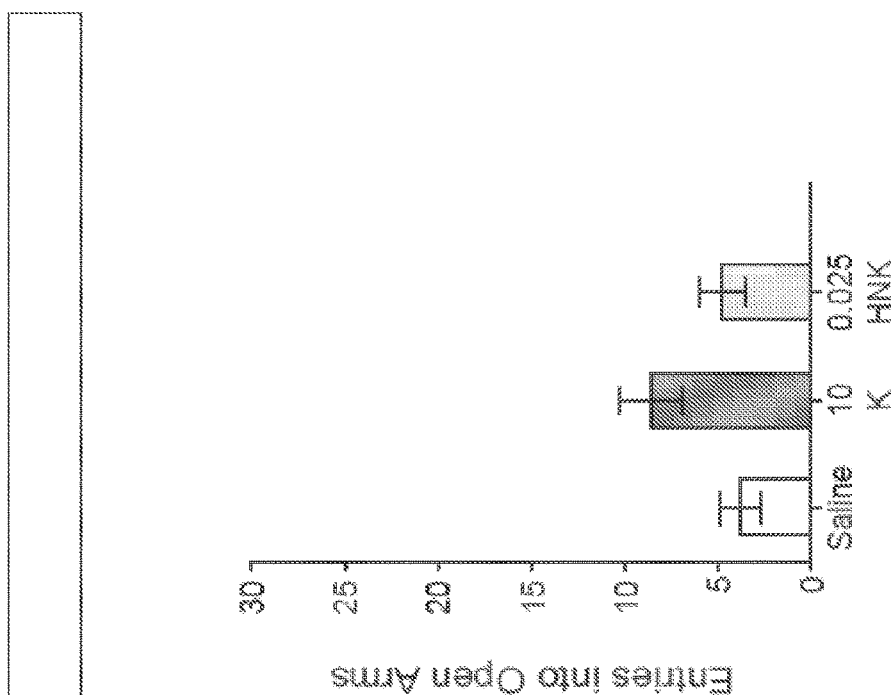
Figure 8C:
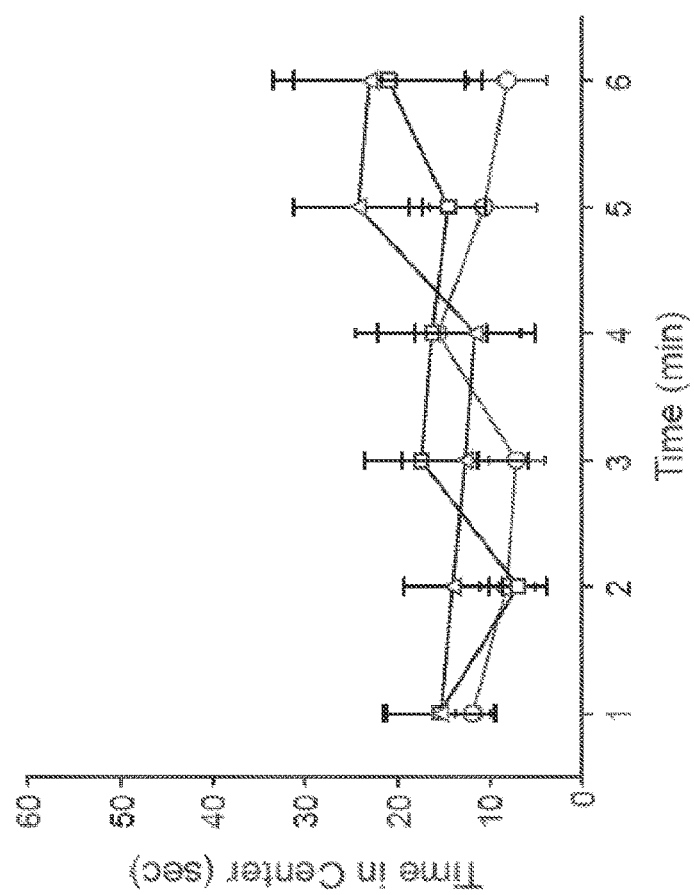
Figure 8H:
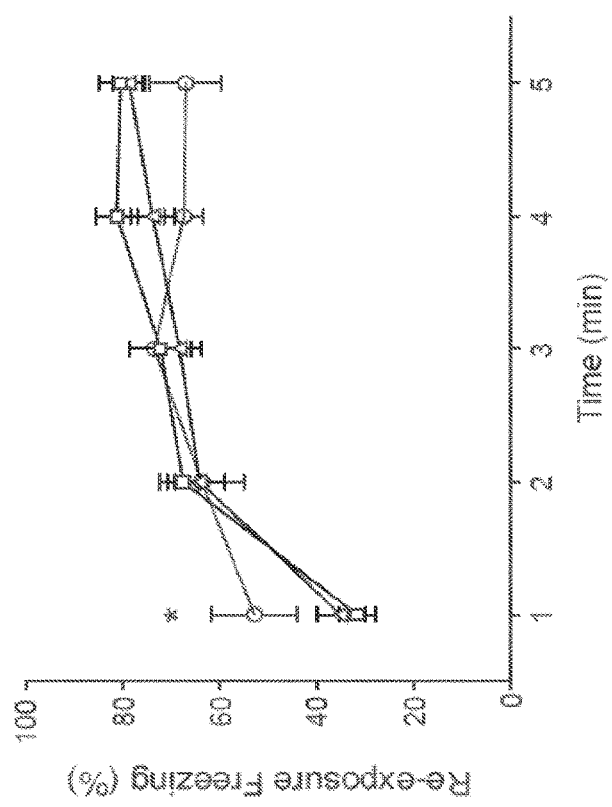
Figure 8G:
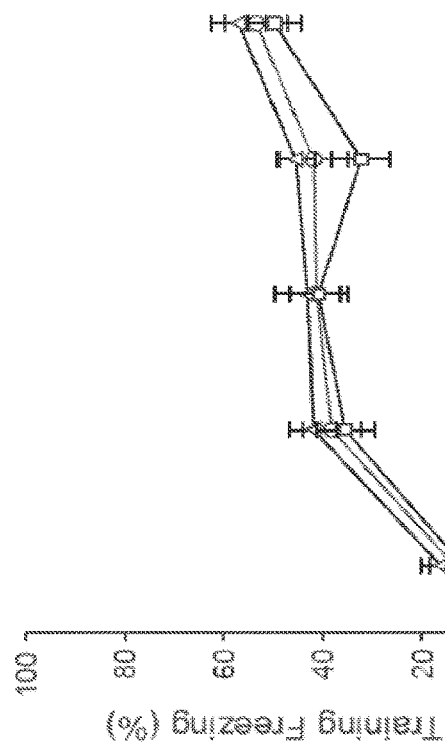
Figure 8I:
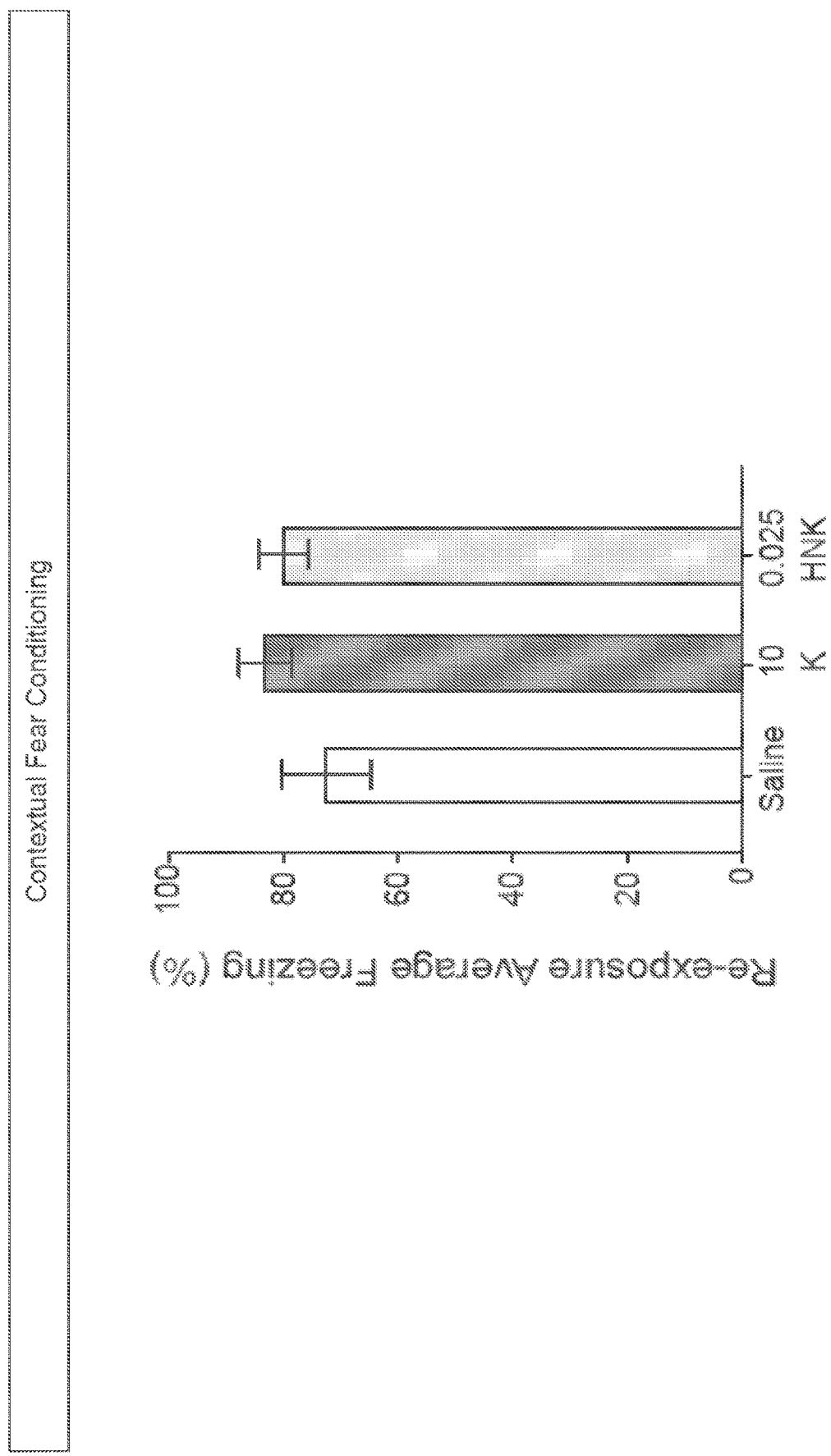

There was no significant effect of drug on session length or escape latency (FIGS. 4B-4D). However, in the FST, (R,S)-ketamine and (2R,6R)-HNK significantly decreased immobility time compared to saline (FIGS. 4E-4F). In contrast to male mice, these data show that (R,S)-ketamine and (2R,6R)-HNK can prevent the onset of LH-induced depressive-like behavior induced by a severe stressor but do not alter LH behavior in females (18). During the EPM, mice administered (R,S)-ketamine, but not (2R,6R)-HNK, spent significantly more time in the open arms and less time in the closed arms compared to saline, demonstrating that ketamine may be anxiolytic in females exposed to LH stress (FIGS. 3G-3I, FIGS. 8A-8F). As with CIS, neither (R,S)-ketamine nor (2R,6R)-HNK affected fear behavior (FIGS. 8G-8I).

Figure 9A:
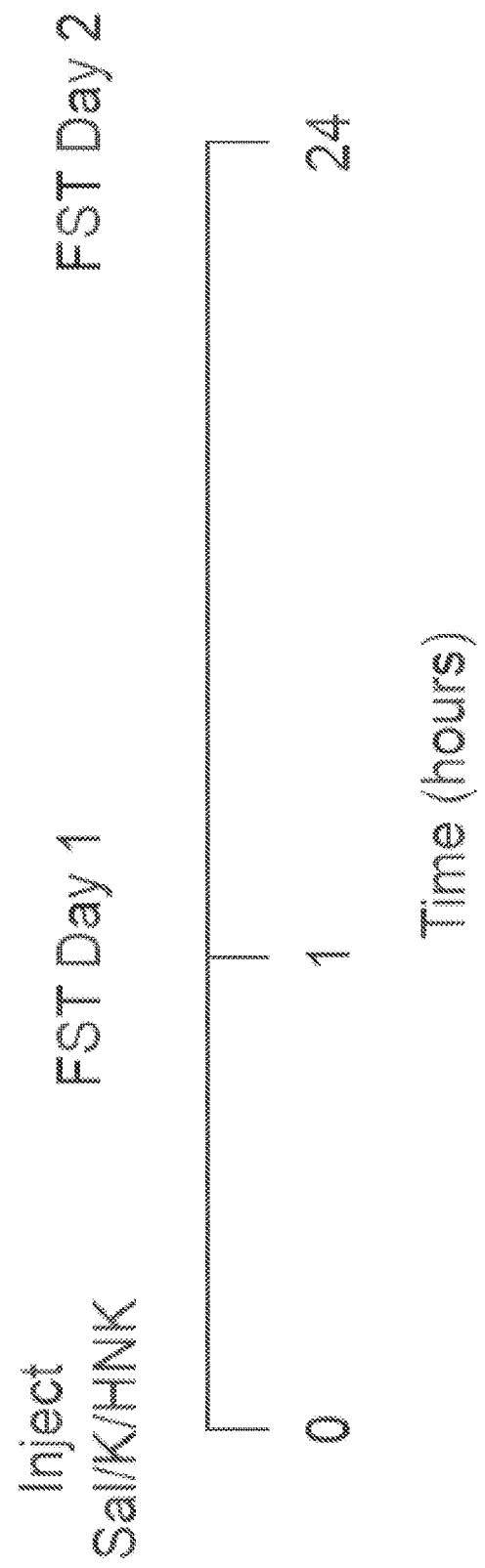
Figure 9C:
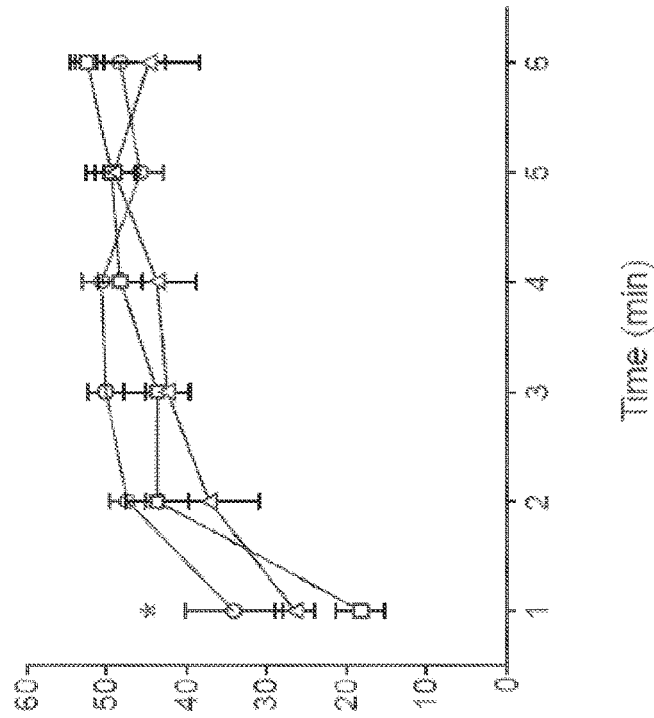
Figure 9B:
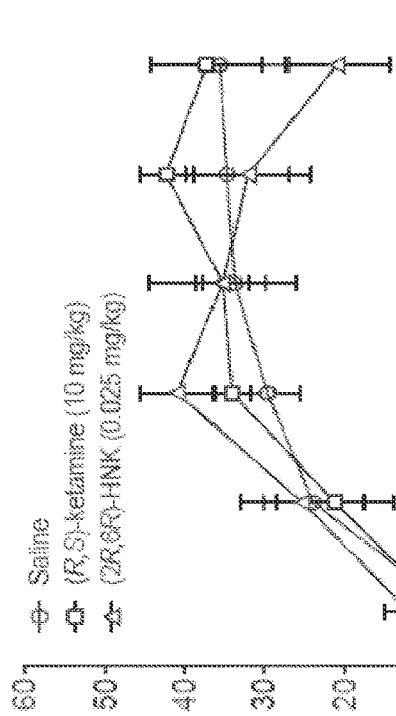
Figure 9D:
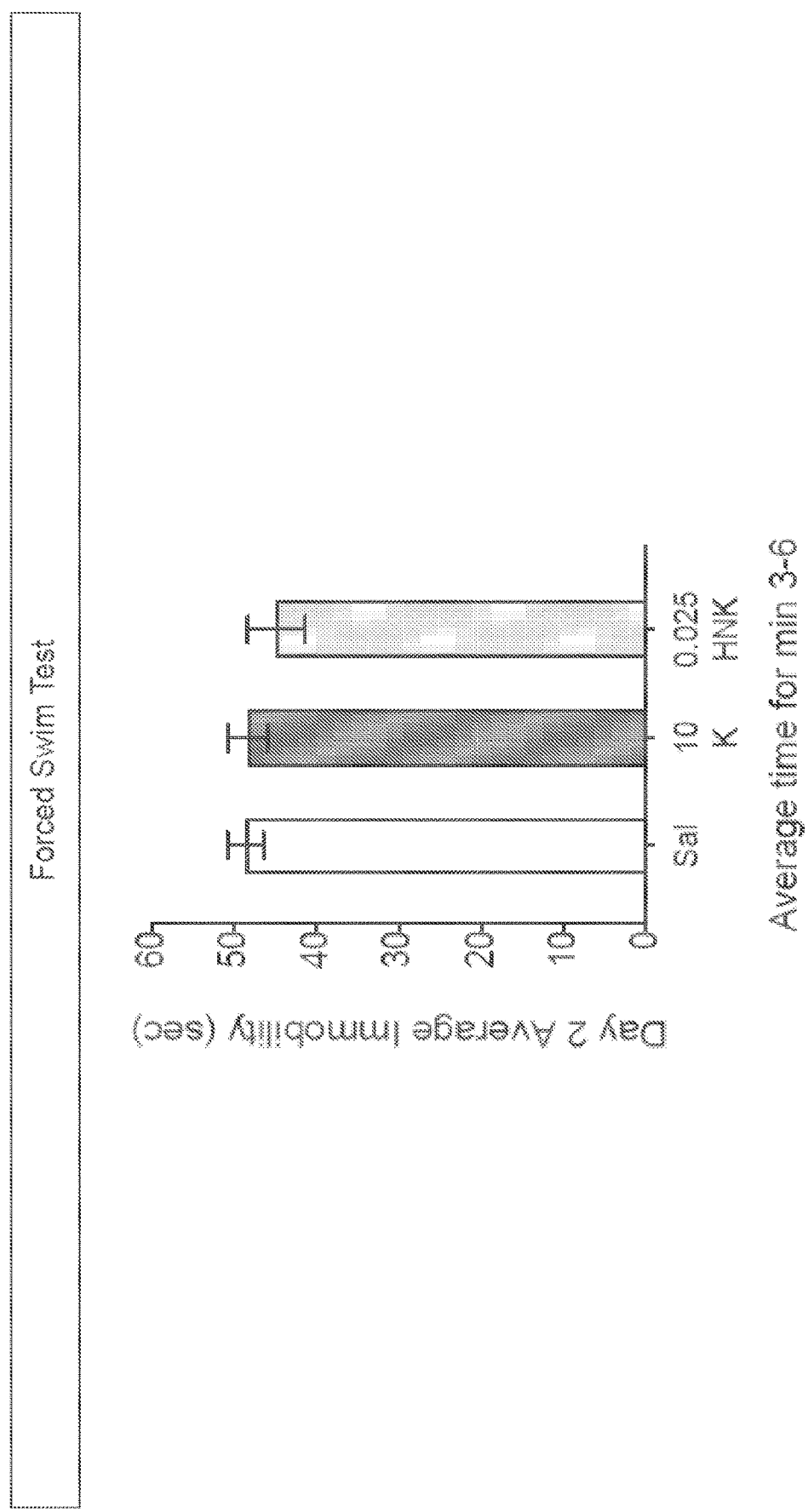

Antidepressant Administration of (R,S)-Ketamine or (2R,6R)-HNK is not Effective in Female Mice Previous results have demonstrated that (R,S)-ketamine and (2R,6R)-HNK are rapid-acting antidepressants and are effective in both males and females (16,17, 24). We therefore investigated if prophylactically effective doses of (R,S)-ketamine and (2R,6R)-HNK were efficacious as antidepressants in females. Mice were administered a single injection of saline, (R,S)-ketamine, and (2R,6R)-HNK one hour prior to administration of the FST. Twenty-four hours later, mice were then administered a second session of the FST (FIG. 9A). During the first FST test, immobility was comparable across all drug groups (FIG. 9B). Similarly, in day 2 of the FST, there were no significant differences in immobility between control saline and experimental drug groups with the exception of the first minute, during which mice administered (R,S)-ketamine (10 mg/kg) were significantly less immobile compared to saline mice (FIGS. 9C-9D). These results demonstrate that the aforementioned doses of (R,S)-ketamine and (2R,6R)-HNK that are prophylactic are ineffective as antidepressants in 129S6/SvEv female mice.

Figure 9E:
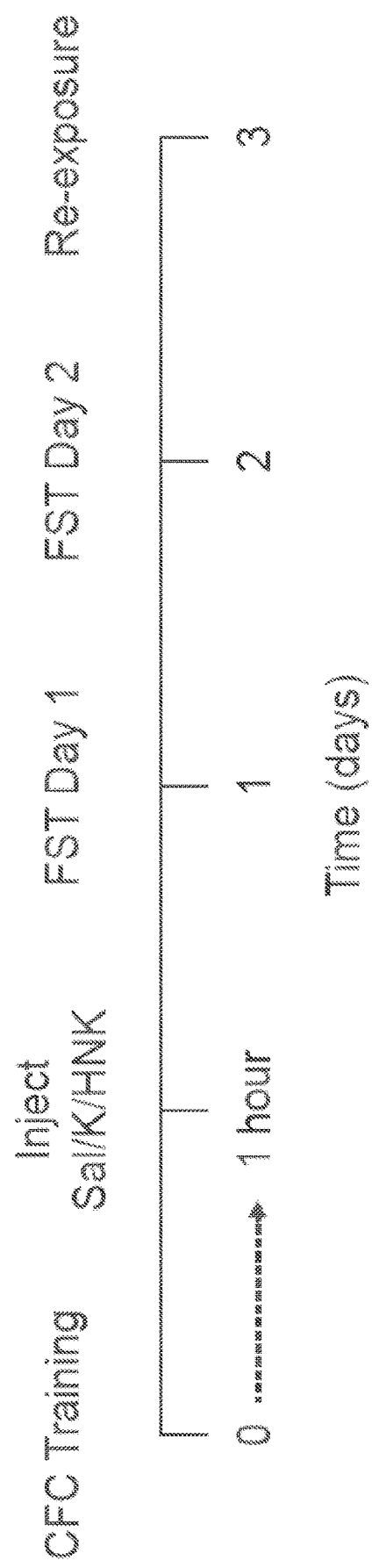
Figure 9H:
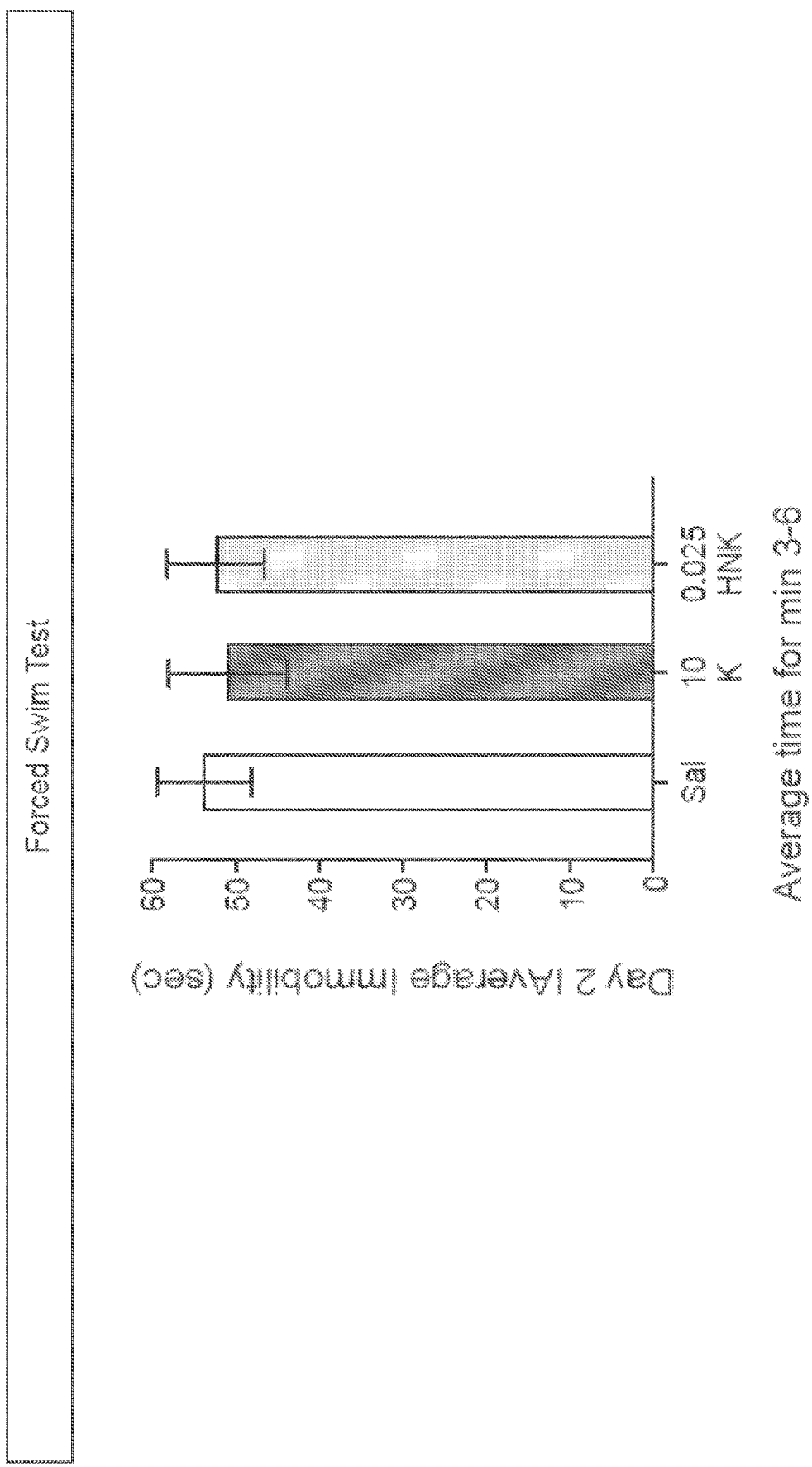
Figure 9J:
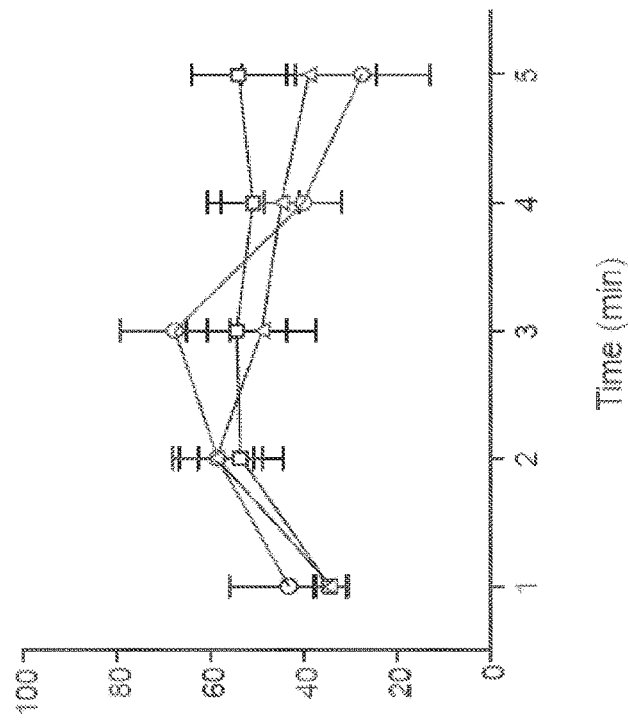
Figure 9I:
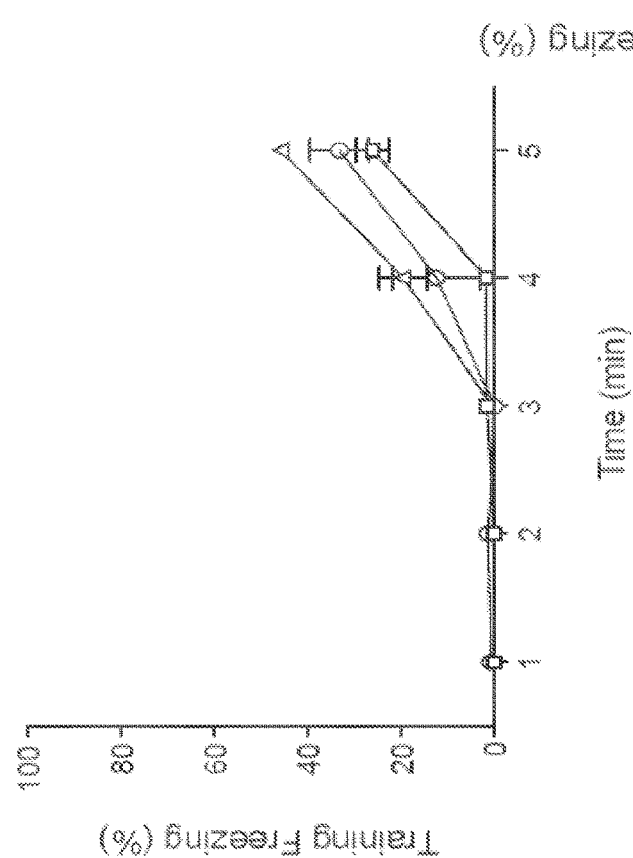
Figure 9K:
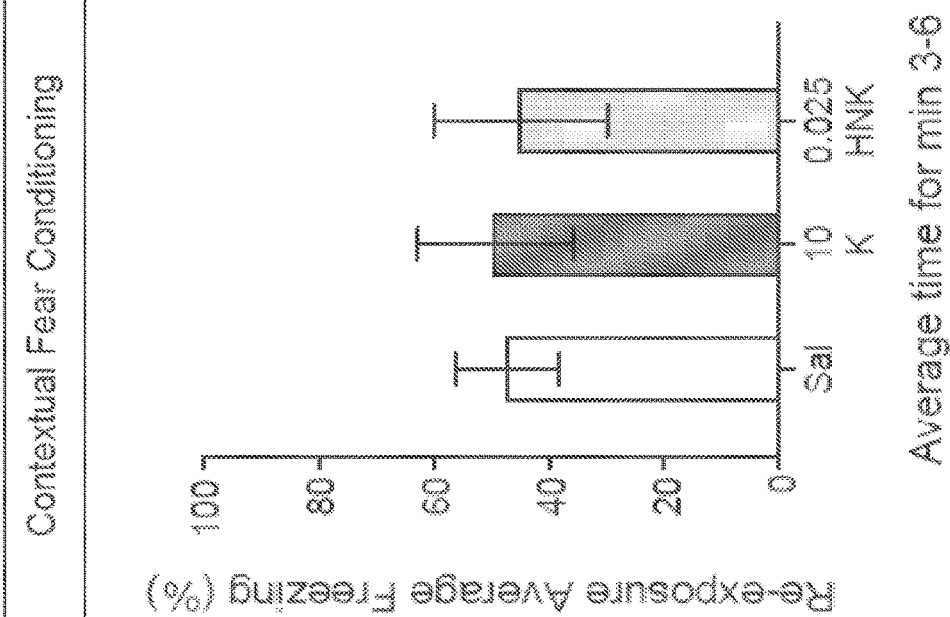

We then sought to determine if (R,S)-ketamine or (2R,6R)-HNK could be antidepressant when administered after a stressor. Mice were administered a 3-shock CFC stressor 1 hour prior to administration of saline, (R,S)-ketamine, or (2R,6R)-HNK. Mice were then administered two subsequent days of the FST followed by re-exposure on the last day (FIG. 9E). (R,S)-ketamine and (2R,6R)-HNK, administered after stress exposure, did not reduce immobility levels in the FST when compared to saline (FIGS. 9F-9H). Additionally, we once again observed that neither compound affected fear behavior during CFC training or re-exposure (FIGS. 9I-9K).

Figure 5A:
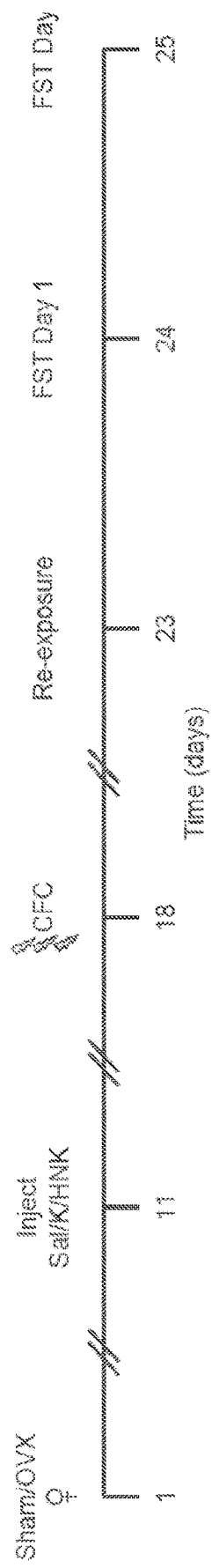

Ovarian Hormones are Necessary for the Prophylactic Efficacy of (R,S)-Ketamine and (2R,6R)-HNK We hypothesized that the increased sensitivity to prophylactic (R,S)-ketamine exhibited by female mice was dependent on ovarian-derived hormones. To test the necessity of these hormones in facilitating ketamine's effects, female mice were ovariectomized at 6 weeks of age and allowed to recover for 10 days (FIG. 5A). Mice were given a single injection of saline, (R,S)-ketamine, or (2R,6R)-HNK one week prior to administration of the CFC behavioral paradigm outlined in FIG. 1A.

Figure 10C:
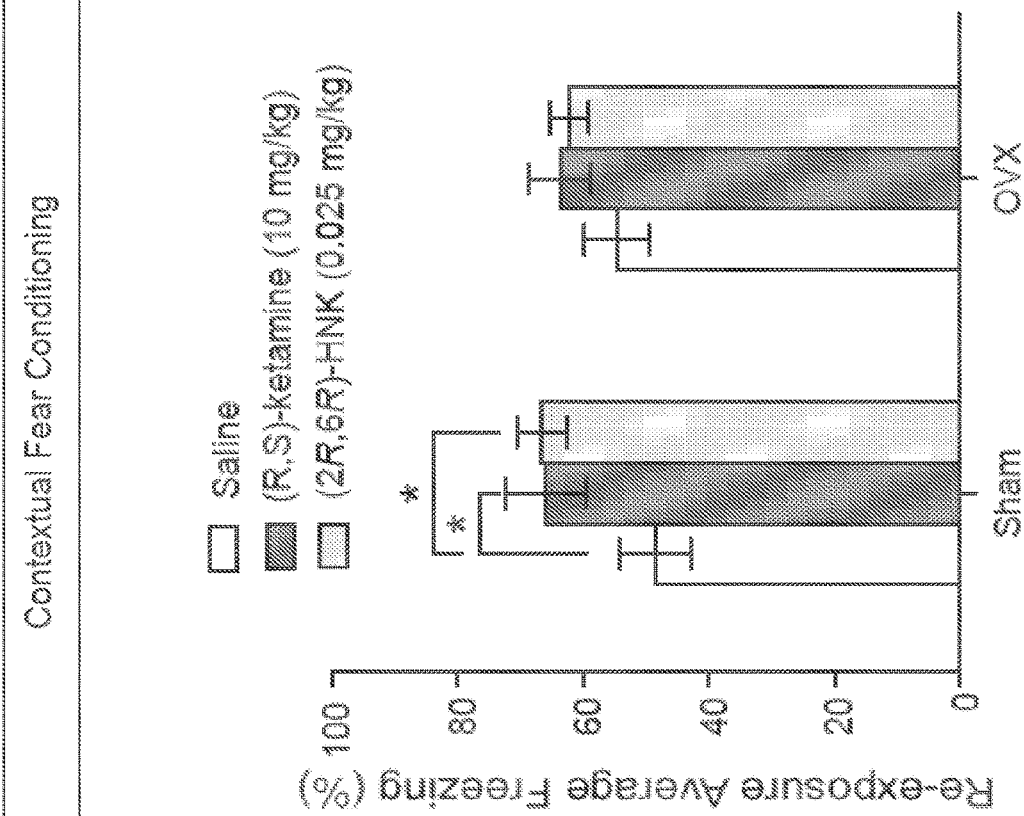

Following OVX, neither (R,S)-ketamine nor (2R,6R)-HNK significantly altered freezing during CFC Training compared to saline controls (FIG. 10A). During re-exposure, freezing in the sham+(R,S)-ketamine and sham+(2R,6R)-HNK groups was altered when compared to the sham+saline group, but freezing in ovariectomized mice was comparable across drug groups (FIGS. 10B-10C). On FST Day 2, in mice administered sham surgery, both (R,S)-ketamine and (2R,6R)-HNK administration decreased immobility time when compared with saline administration. However, in the OVX group, mice displayed comparable immobility across all drug groups at levels similar to sham+saline mice (FIGS. 5B-5C). Therefore, we concluded that ovarian-derived hormones were necessary for the prophylactic effects of (R,S)-ketamine and (2R,6R)-HNK.

Figure 5D:
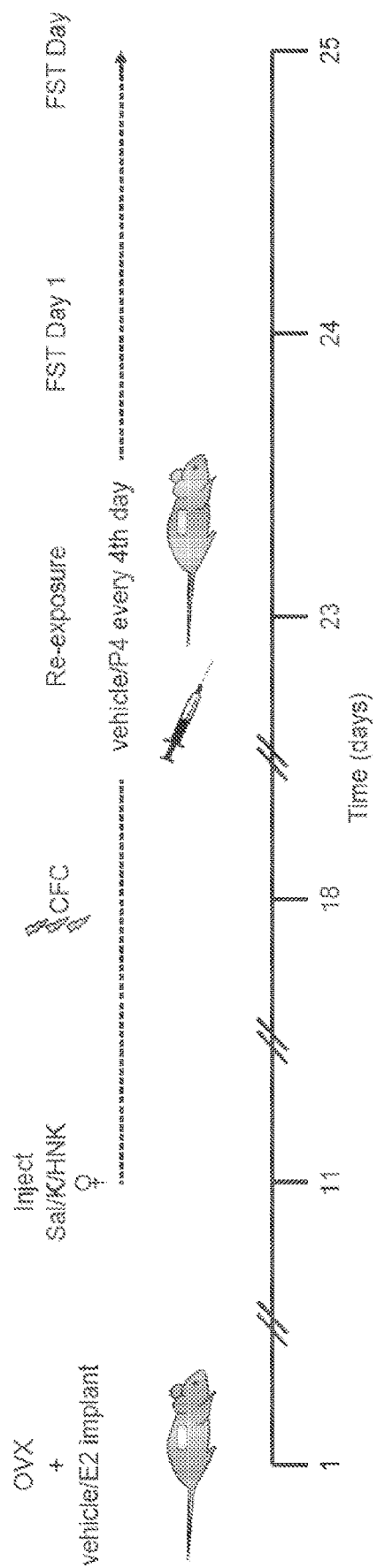

Ovarian-Derived Hormones are Sufficient to Restore the Prophylactic Efficacy of (R,S)-Ketamine and (2R,6R)-HNK Subsequently, we aimed to investigate whether exogenous application of ovarian hormones following ovariectomy surgery could restore the prophylactic effects of (R,S)-ketamine and (2R,6R)-HNK. Female mice were ovariectomized and implanted with subcutaneous estrogen or vehicle capsules (FIG. 5D). After 10 days of recovery, mice were administered a single injection of saline, (R,S)-ketamine, or (2R,6R)-HNK. One week later, we administered the same behavioral paradigm described in FIG. 1A. Beginning with saline, ketamine, or (2R,6R)-HNK administration and continuing throughout the remainder of the behavioral protocol, mice were given vehicle or progesterone (P4) injections (0.5 mg dissolved in 0.3 ml sesame oil) every fourth day. This hormone replacement protocol has previously been used to mimic the estrous cycle in female mice (28).

Figure 10F:
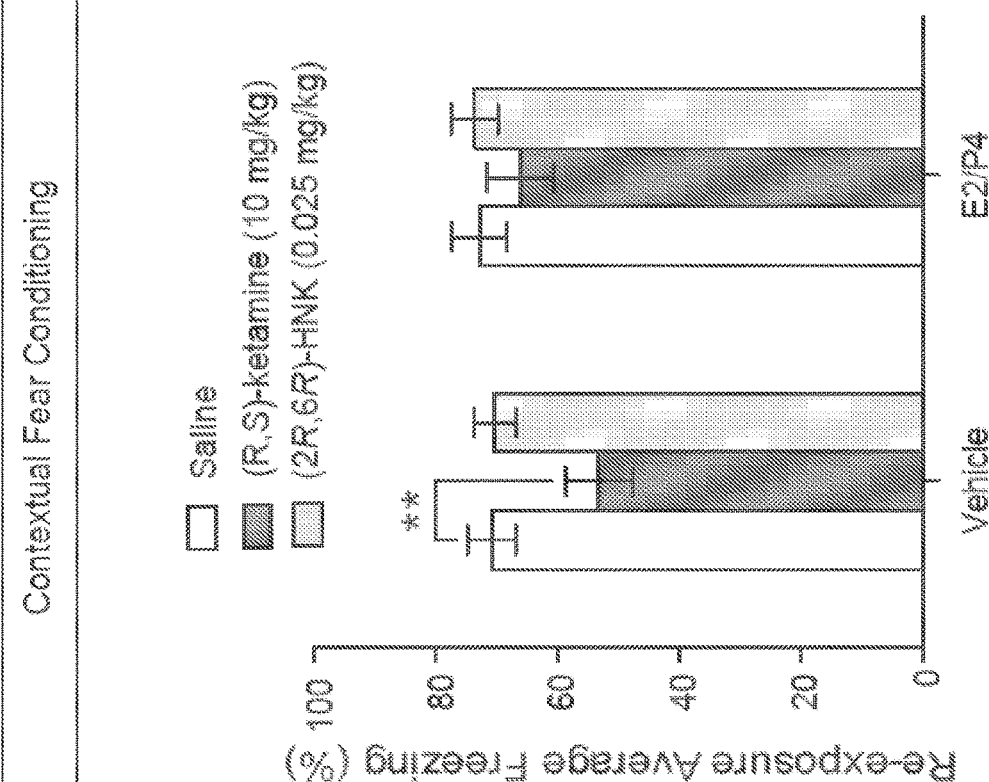

In the CFC Training session, E2/P4+(R,S)-ketamine and E2/P4+(2R,6R)-HNK mice froze significantly more when compared to vehicle+(R,S)-ketamine and vehicle+(2R,6R)-HNK groups, respectively. (FIG. 10D). During re-exposure, in the vehicle condition, mice administered (R,S)-ketamine, but not (2R,6R)-HNK, displayed altered freezing when compared to the saline group. Freezing was comparable across drug groups in the E2/P4 condition (FIGS. 10E-10F).

In the FST, cyclic replacement of ovarian hormones restored the prophylactic effects of both (R,S)-ketamine and (2R,6R)-HNK (FIGS. 5E-5F). Ovariectomized vehicle control mice displayed comparable immobility behavior across all drug groups. However, in the hormone replacement group, mice administered (R,S)-ketamine and (2R,6R)-HNK were significantly less immobile compared to control saline mice, indicating that replacing E2 and P4 after OVX surgery restored the prophylactic actions of ketamine and its metabolite. These data demonstrate that ovarian-derived hormones are sufficient for the prophylactic effects of (R,S)-ketamine and (2R,6R)-HNK in females.

Discussion

This series of experiments yielded two main findings: 1) (R,S)-ketamine and its metabolite (2R,6R)-HNK are prophylactic against stress-induced depressive-like behavior, but do not alter learned fear, in females, and 2) prophylactic efficacy in female mice is modulated by ovarian hormones. Both (R,S)-ketamine and (2R,6R)-HNK prevented the onset of depressive-like behavior in a wide range of stress models when administered one week before stress exposure, suggesting that both compounds have a defined window of efficacy. Moreover, the estrous cycle was both necessary and sufficient for the protective properties of (R,S)-ketamine and (2R,6R)-HNK. These data suggest that prophylactic compounds act on neural circuits mediated by gonadal hormones to enhance stress resilience in female mice. To our knowledge, this study is the first to demonstrate the efficacy of prophylactics in female mice and to show that (2R,6R)-HNK exhibits the same protective properties as its ketamine precursor.

Historically, females have not been used to study pharmacological therapies for psychiatric disorders. However, numerous studies have shown that male and female subjects respond differently to ketamine and that doses effective in males may produce adverse outcomes in females (16-17,29). Although specific reasons for this difference are unknown, sex differences in pharmacokinetics or pharmacodynamics could play an important role. For example, sex differences in the absorption, distribution in body fat, plasma binding levels, or clearance by hepatic enzymes of ketamine may lead to higher free drug concentrations in females than in males (30-32). Alternatively, sex differences in the availability and binding efficiency of certain receptors, such as N-methyl-D-aspartic acid receptors (NMDARs) or α-amino-3-hydroxy-5-methyl-4-isoxazolepropionic acid receptors (AMPARs), may lead to greater transduction of ketamine's effects in females than in males, making them more susceptible to anxiogenic and depressogenic outcomes (30,33-34). Together, these data demonstrate the utility of specifically separating experimental cohorts by sex or studying sex as an experimental variable.

Another factor that may influence ketamine dosing and efficacy in females is the estrous cycle. Because our pharmacological and behavioral manipulations occurred over a long period of time, we did not track the estrous cycle in our study in order to minimize handling stress. However, previous studies have demonstrated that ovarian hormones can significantly impact neuronal morphology, rodent behavior, and ketamine efficacy (35-37). A study from Shansky et al. showed that estrogen administration in ovariectomized females can increase spine density in unstressed animals and augment dendritic length after exposure to stress (35). A separate study found that estrous cycle stage during administration can affect ketamine's antidepressant efficacy, perhaps by modulating the phosphorylation of certain receptors, including the GluA1 subunit of the AMPAR, or by modifying the expression of neurotrophic proteins (36). Recently, Saland and colleagues demonstrated that disrupting the estrous cycle prevented a hedonic response to ketamine in female rats, but that restoring the estrous cycle using E2/P4 replacement reinstated this hedonic response (37). In line with this literature, our results support the hypothesis that ovarian hormones induce changes at the neuronal level to causally mediate ketamine's effects, whether antidepressant or prophylactic, and thus impact behavior in females. Therefore, studying the interaction of ovarian-derived hormones and ketamine administration may facilitate the discovery of underlying mechanisms by which ketamine promotes stress resilience in the brain.

In addition to differences in drug dosage, we observed dissimilarities in prophylactic ketamine's effect on fear behavior between sexes. Similar to our results, a recent study reported that prophylactic ketamine administered to female rats before inescapable shock stress prevented reductions in social exploration but did not report changes in learned helplessness behavior (18,38). Indeed, across species, a number of studies have demonstrated divergent symptoms of mood disorders between sexes. While women diagnosed with MDD are more likely to experience a comorbid anxiety disorder and greater suicidal ideation, men are at greater risk of comorbid substance abuse (39). Moreover, in rodent models of depression, females do not acquire a learned helplessness phenotype, do not express anhedonia as strongly as males, and are more susceptible to swimming stress (40-41). Thus, males and females likely process stress using separate neural strategies that result in distinct behavioral responses. Consequently, many paradigms developed to model pathological behavior in male animals may be inappropriate for use in female animals.

Additionally, we did not find that (R,S)-ketamine and (2R,6R)-HNK were antidepressant in female mice. However, we do not believe these results contradict previous findings (24-25,42). Instead, differences in mouse strain and drug dosing likely contributed to the discrepancies that we have demonstrated. Although we utilized 129S6/SvEvTac mice, ours and other previous studies have shown efficacy in BALB/cJ or C57BL/6J mice (24-25,42). Moreover, while antidepressant (2R,6R)-HNK is typically administered at 10 mg/kg doses, here, we administered this drug at 0.025 mg/kg. Thus, (R,S)-ketamine and (2R,6R)-HNK could still be efficacious as antidepressants in females of different mouse strains or when administered at different doses.

In our study, we chose to investigate stereospecific ketamine compounds and metabolites because, as racemic ketamine has a high abuse potential and induces psychotropic side effects, developing effective alternatives to (R,S)-ketamine could reduce negative outcomes in the clinic (43). Recently, (S)-ketamine has been shown to rapidly attenuate depressive symptoms in MDD patients and is currently being developed to treat TRD (44-45). However, studies in rodent models have demonstrated that (R)-ketamine may be more potent and longer-lasting than (S)-ketamine with a reduced chance of psychomimetic and neurotoxic side effects (46-48). Moreover, the stereospecific metabolite (2R, 6R)-HNK, but not (2S,6S)-HNK, has also been shown to possess potent and long-lasting antidepressant properties (24). This demonstrated enantioselectivity may indicate potential mechanisms by which ketamine acts as a rapid-acting antidepressant or as a stress-enhancing prophylactic. As (S)-ketamine is a four-fold stronger antagonist of the NMDAR, it is likely that ketamine exerts its antidepressant effects through additional or alternative mechanisms (43). While several studies have proposed that ketamine attenuates depressive-like symptoms by activating AMPARs, there is debate whether this action is dose-specific and whether it directly mediates ketamine's antidepressant actions (24,43, 49).

However, while the in vivo actions of ketamine-based antidepressants are debated, the mechanisms of prophylactic ketamine also remain unclear. In male mice, our lab has shown that prophylactic ketamine acts on the transcription factor ΔFosB to alter neural ensembles in the ventral hippocampus and can influence the balance of excitatory and inhibitory neurotransmitters in the brain after exposure to stress (50-51). Although further study is necessary to determine if these mechanisms also apply to females, these data will be crucial for the development of next-generation stress-enhancing prophylactic agents.

In summary, these experiments demonstrate that (R,S)-ketamine and (2R,6R)-HNK are effective prophylactics against a variety of stressors in females and are causally mediated by ovarian-derived hormones. Ultimately, this study offers insight into the prevention of depressive-like behavior in a particularly susceptible population. Moreover, examining the mechanisms by which prophylactic compounds enhance stress resilience will serve to elucidate the underlying neuropathology and sex differences driving MDD and therefore contribute to advancements in targeted therapies for mood-based disorders.

Our findings include the following. (2R,6R)-hydroxynorketamine (HNK) is prophylactic in male and female mice at sex-specific doses of 0.075 mg/kg and 0.025 mg/kg, respectively. (R,S)-ketamine is prophylactic in female mice at a dose of 10 mg/kg, while the dose is 30 mg/kg as previously shown in male mice. (2R,6R)-HNK acts faster in females to induce stress resilience in a shorter 3-day time interval between injection and stressor. (R,S)-ketamine and (2R,6R)-HNK protect against stress-induced depressive-like behavior in females in a variety of acute and chronic stressors. (R,S)-ketamine may reduce anxiety-like behavior in females following learned helplessness (LH) stress contrary to their male counterparts. The prophylactic efficacy of (R,S)-ketamine and (2R,6R)-HNK is dependent at least in part on ovarian-derived hormones. We have found that a single sub-anesthetic injection of (R,S)-ketamine, administered at 10 mg kg-1, or (2R,6R)-hydroxynorketamine (HNK), administered at 0.025 mg kg-1, protects against the onset of depression in females. Moreover, we have also discovered that (2R,6R)-HNK can also act as a prophylactic in males at a sex-specific dose of 0.075 mg kg-1. Mice given the drug one week before a stressor show significantly decreased depressive-like behavior as measured by immobility in the forced swim test. (2R,6R)-HNK was prophylactically effective within a smaller time interval than (R,S)-ketamine (i.e. 3 days), and we validated both prophylactic compounds using various stress models.

Tables 1-1 to 1-10. Statistical analysis summaries.
Table 2. List of experimental mice per group.
Table 3. Summary of behavioral results for each experiment.

REFERENCES

1. WHO. Depression Fact Sheet. *World Health Organization*. 2017.
2. National Research Council & Institute of Medicine Committee on Depression, Parenting Practices, and the Healthy Development of Children. *Depression in Parents, Parenting, and Children: Opportunities to Improve Identification, Treatment, and Prevention*. National Academies Press: Washington D.C., 2009.
3. Flory J D, Yehuda R. Comorbidity between post-traumatic stress disorder and major depressive disorder: alternative explanations and treatment considerations. *Dialogues Clin Neurosci*. 2015; 17(2):141-50.
4. Kessler R C, Berglund P, Demler O, Jin R, Merikangas K R, Walters E E. Lifetime prevalence and age-of-onset distributions of DSM-IV disorders in the National Comorbidity Survey Replication. *Arch Gen Psychiatry*. 2005; 62(6):593-602.
5. Piccinelli M, Wilkinson G. Gender differences in depression: critical review. *Br J Psychiatry*. 2000; 177(6):486-92.
6. Davidson R J, Pizzagalli D, Nitschke J B, Putnam K. Depression: perspectives from affective neuroscience. *Ann Rev Psychology*. 2002; 53:545-74.
7. Kornstein S G. Gender differences in depression: implications for treatment. *J Clin Psychiatry*. 1997; 15:12-8.
8. Al-Harbi K S. Treatment-resistant depression: therapeutic trends, challenges, and future directions. *Patient Prefer Adherence*. 2012; 6:369-88.
9. Kornstein S G, Schatzberg A F, Thase M E, Yonkers K A, McCullough J P, Keitner G I, et al. Gender differences in treatment response to sertraline versus imipramine in chronic depression. *Am J Psychiatry*. 2000; 157(9):1445-52.
10. Serafini G, Howland R H, Rovedi F, Girardi P, Amore M. The Role of Ketamine in Treatment-Resistant Depression: A Systematic Review. *Curr Neuropharmacol*. 2014; 12(5):444-61.
11. Autry A E, Adachi M, Nosyreva E, Na E S, Los M F, Cheng P F, et al. NMDA receptor blockade at rest triggers rapid behavioural antidepressant responses. *Nature*. 2011; 475(7354):91-5.
12. Zarate C A, Jr., Singh J B, Carlson P J, Brutsche N E, Ameli R, Luckenbaugh D A, et al. A randomized trial of an N-methyl-D-aspartate antagonist in treatment-resistant major depression. *Arch Gen Psychiatry*. 2006; 63(8):856-64.
13. Al Shirawi M I, Kennedy S H, Ho K T, Byrne R, Downar J. Oral Ketamine in Treatment-Resistant Depression: A Clinical Effectiveness Case Series. *J Clin Psychopharmacol*. 2017; 37(4):464-7.
14. Browne C A, Lucki I. Antidepressant effects of ketamine: mechanisms underlying fast-acting novel antidepressants. *Front Pharmacol*. 2013; 4.
15. Zarate C A, Jr., Brutsche N E, Ibrahim L, Franco-Chaves J, Diazgranados N, Cravchik A, et al. Replication of ketamine's antidepressant efficacy in bipolar depression: a randomized controlled add-on trial. *Biol Psychiatry*. 2012; 71(11):939-46.
16. Franceschelli A, Sens J, Herchick S, Thelen C, Pitychoutis P M. Sex differences in the rapid and the sustained antidepressant-like effects of ketamine in stress-naive and "depressed" mice exposed to chronic mild stress. *Neuroscience*. 2015; 290:49-60.
17. Carrier N, Kabbaj M. Sex differences in the antidepressant-like effects of ketamine. *Neuropharmacology*. 2013; 70:27-34.
18. Brachman R A, McGowan J C, Perusini J N, Lim S C, Pham T H, Faye C, et al. Ketamine as a Prophylactic Against Stress-Induced Depressive-like Behavior. *Biol Psychiatry*. 2016; 79(9):776-86.
19. McGowan J C, LaGamma C T, Lim S C, Tsitsiklis M, Neria Y, Brachman R A, et al. Prophylactic Ketamine Attenuates Learned Fear. *Neuropsychopharmacology*. 2017; 42(8):1577-89.

20. Amat J, Dolzani S D, Tilden S, Christianson J P, Kubala K H, Bartholomay K, et al. Previous Ketamine Produces an Enduring Blockade of Neurochemical and Behavioral Effects of Uncontrollable Stress. *J Neuro.* 2016; 36(1): 153-61.
21. Soumier A, Carter R M, Schoenfeld T J, Cameron H A. New Hippocampal Neurons Mature Rapidly in Response to Ketamine But Are Not Required for Its Acute Antidepressant Effects on Neophagia in Rats. *eNeuro.* 2016; 3(2).
22. Zarate C A, Jr., Brutsche N, Laje G, Luckenbaugh D A, Venkata S L, Ramamoorthy A, et al. Relationship of ketamine's plasma metabolites with response, diagnosis, and side effects in major depression. *Biol Psychiatry.* 2012; 72(4):331-8.
23. Mion G, Villevieille T. Ketamine Pharmacology: An Update (Pharmacodynamics and Molecular Aspects, Recent Findings). *CNS Neurosci Ther.* 2013; 19(6):370-80.
24. Zanos P, Moaddel R, Morris P J, Georgiou P, Fischell J, Elmer G I, et al. NMDAR inhibition-independent antidepressant actions of ketamine metabolites. *Nature.* 2016; 533(7604):481-6.
25. Yamaguchi J-i, Toki H, Qu Y, Yang C, Koike H, Hashimoto K et al. (2R,6R)-Hydroxynorketamine is not essential for the antidepressant actions of (R)-ketamine in mice. *Neuropsychopharmacology.* 2018.
26. Strom J O, Theodorsson A, Ingberg E, Isaksson I-M, Theodorsson E. Ovariectomy and 17beta-estradiol Replacement in Rats and Mice: A Visual Demonstration. *JoVE.* 2012 (64):e4013.
27. Porsolt R D, Le Pichon M, Jalfre M. Depression: a new animal model sensitive to antidepressant treatments. *Nature* 1977; 266(5604): 730-732.
28. Rissman E F, Early A H, Taylor J A, Korach K S, Lubahn D B. Estrogen receptors are essential for female sexual receptivity. *Endocrinology.* 1997; 138(1):507-10.
29. Thelen C, Sens J, Mauch J, Pandit R, Pitychoutis P M. Repeated ketamine treatment induces sex-specific behavioral and neurochemical effects in mice. *Behav Brain Res.* 2016; 312:305-12.
30. Soldin O P, Mattison D R. Sex differences in pharmacokinetics and pharmacodynamics. *Clin Pharmacokinet* 2009; 48(3): 143-157.
31. Waxman D J, Holloway M G. Sex differences in the expression of hepatic drug metabolizing enzymes. *Mol Pharmacol* 2009; 76(2): 215-228.
32. Schwartz J B. The influence of sex on pharmacokinetics. *Clin Pharmacokinet* 2003; 42(2): 107-121.
33. Honack D, Loscher W. Sex differences in NMDA receptor mediated responses in rats. *Brain Res* 1993; 620(1): 167-170.
34. Palomero-Gallagher N, Bidmon H J, Zilles K. AMPA, kainate, and NMDA receptor densities in the hippocampus of untreated male rats and females in estrus and diestrus. *J Comp Neurol* 2003; 459(4): 468-474.
35. Shansky R M, Hamo C, Hof P R, Lou W, McEwen B S, Morrison J H. Estrogen promotes stress sensitivity in a prefrontal cortex-amygdala pathway. *Cerebral cortex* (New York, N.Y.: 1991) 2010; 20(11): 2560-2567.
36. Dossat A M, Wright K N, Strong C E, Kabbaj M. Behavioral and biochemical sensitivity to low doses of ketamine: Influence of estrous cycle in C57B L/6 mice. *Neuropharmacology* 2018; 130: 30-41.
37. Saland S K, Schoepfer K J, Kabbaj M. Hedonic sensitivity to low-dose ketamine is modulated by gonadal hormones in a sex-dependent manner. *Sci Rep.* 2016; 6.
38. Dolzani S D, Baratta M V, Moss J M, Leslie N L, Tilden S G, Sorensen A T, et al. Inhibition of a Descending Prefrontal Circuit Prevents Ketamine-Induced Stress Resilience in Females. *eNeuro.* 2018; 5(1).
39. Altemus M, Sarvaiya N, Epperson C N. Sex differences in anxiety and depression clinical perspectives. *Front Neuroendocrinol* 2014; 35(3): 320-330.
40. Dalla C, Edgecomb C, Whetstone A S, Shors T J. Females do not Express Learned Helplessness like Males do. *Neuropsychopharmacology.* 2007; 33(7):1559-69.
41. Kokras N, Dalla C. Sex differences in animal models of psychiatric disorders. *Br J Pharmacol* 2014; 171(20): 4595-4619.
42. Pham T H, Defaix C, Xu X, Deng S X, Fabresse N, Alvarez J C et al. Common Neurotransmission Recruited in (R,S)-Ketamine and (2R,6R)-Hydroxynorketamine-Induced Sustained Antidepressant-like Effects. *Biol Psychiatry* 2018; 84(1): e3-e6.
43. Aleksandrova L R, Phillips A G, Wang Y T. Antidepressant effects of ketamine and the roles of AMPA glutamate receptors and other mechanisms beyond NMDA receptor antagonism. *J Psychiatry Neurosci* 2017; 42(4): 222-229.
44. Singh J B, Fedgchin M, Daly E, Xi L, Melman C, De Bruecker G et al. Intravenous Esketamine in Adult Treatment-Resistant Depression: A Double-Blind, Double-Randomization, Placebo-Controlled Study. *Biol Psychiatry* 2016; 80(6): 424-431.
45. Daly E J, Singh J B, Fedgchin M, Cooper K, Lim P, Shelton R C et al. Efficacy and Safety of Intranasal Esketamine Adjunctive to Oral Antidepressant Therapy in Treatment-Resistant Depression: A Randomized Clinical Trial. *JAMA* 2018; 75(2): 139-148.
46. Zhang J C, Li S X, Hashimoto K. R (−)-ketamine shows greater potency and longer lasting antidepressant effects than S (+)-ketamine. *Pharmacol Biochem Behav.* 2014; 116:137-41.
47. Yang C, Shirayama Y, Zhang J C, Ren Q, Yao W, Ma M et al. R-ketamine: a rapid-onset and sustained antidepressant without psychotomimetic side effects. *Transl Psychiatry* 2015; 5: e632.
48. Fukumoto K, Toki H, Tijima M, Hashihayata T, Yamaguchi Ji, Hashimoto K et al. Antidepressant Potential of (R)-Ketamine in Rodent Models: Comparison with (S)-Ketamine. *J Pharmacol Exp Ther* 2017; 361(1): 9-16.
49. Suzuki K, Nosyreva E, Hunt K W, Kavalali E T, Monteggia L M. Effects of a ketamine metabolite on synaptic NMDAR function. *Nature* 2017; 546(7659): E1-e3.
50. Mastrodonato A, Martinez R, Pavlova I P, LaGamma C T, Brachman R A, Robison A J et al. Ventral CA3 Activation Mediates Prophylactic Ketamine Efficacy Against Stress-Induced Depressive-like Behavior. *Biol Psychiatry.*
51. McGowan J C, Hill C, Mastrodonato A, LaGamma C T, Kitayev A, Brachman R A et al. Prophylactic ketamine alters nucleotide and neurotransmitter metabolism in brain and plasma following stress. *Neuropsychopharmacology* 2018; 43(9): 1813-1821.
52. Drew M R, Denny C A, Hen R. Arrest of adult hippocampal neurogenesis in mice impairs single- but not multiple-trial contextual fear conditioning. *Behav Neurosci.* 2010; 124(4):446-54.
53. Denny C A, Kheirbek M A, Alba E L, Tanaka K F, Brachman R A, Laughman K B, et al. Hippocampal Memory Traces Are Differentially Modulated by Experience, *Time, and Adult Neurogenesis. Neuron.* 2014; 83(1): 189-201.

54. Joo Y, Choi K M, Lee Y H, Kim G, Lee D H, Roh G S, et al. Chronic immobilization stress induces anxiety- and depression-like behaviors and decreases transthyretin in the mouse cortex. *Neurosci Lett.* 2009; 461(2):121-5.
55. Ramirez S, Liu X, MacDonald C J, Moffa A, Zhou J, Redondo R L et al. Activating positive memory engrams suppresses depression-like behaviour. *Nature* 2015; 522 (7556): 335-339.
56. Brachman R A, McGowan J C, Perusini J N, Lim S C, Pham T H, Faye C et al. Ketamine as a Prophylactic Against Stress-Induced Depressive-like Behavior. *Biological psychiatry* 2016; 79(9): 776-786.
57. Elhabazi K, Ayachi S, Ilien B, Simonin F. Assessment of Morphine-induced Hyperalgesia and Analgesic Tolerance in Mice Using Thermal and Mechanical Nociceptive Modalities. *JoVE* 2014; (89): e51264.
58. Saxe M D, Battaglia F, Wang J W, Malleret G, David D J, Monckton J E et at. Ablation of hippocampal neurogenesis impairs contextual fear conditioning and synaptic plasticity in the dentate gyrus. *Proc Natl Acad Sci* 2006; 103(46): 17501-17506.
59. David D J, Samuels B A, Rainer Q, Wang J-W, Marsteller D, Mendez I et al. Neurogenesis-Dependent and -Independent Effects of Fluoxetine in an Animal Model of Anxiety/Depression. Neuron 2009; 62(4): 479-493.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, and publications are cited throughout this application, the disclosures of which, particularly, including all disclosed chemical structures, are incorporated herein by reference. Citation of the above publications or documents is not intended as an admission that any of the foregoing is pertinent prior art, nor does it constitute any admission as to the contents or date of these publications or documents. All references cited herein are incorporated by reference to the same extent as if each individual publication, patent application, or patent, was specifically and individually indicated to be incorporated by reference.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

TABLE 1-1

| | | | Statistical analysis - Cohort: 1 week prophylactic drug | | | | | |
|---|---|---|---|---|---|---|---|---|
| Behavioral Paradigm | Measurement | Statistical Test | Comparison | F | ° of freedom | p | * | FIG. |
| Contextual Fear Conditioning Re-exposure | Freezing (Average) | ANOVA Dunnett test | Drug | 2.360 | 15,161 | 0.0043 | ** | 1B |
| | | | Sal vs. K (2.5) | — | — | 0.7546 | — | 1B |
| | | | Sal vs. K (10) | — | — | 0.8986 | — | |
| | | | Sal vs. K (30) | — | — | 0.8647 | — | |
| | | | Sal vs. (2R,6R)-HNK (0.025) | — | — | 0.4341 | — | 1C |
| | | | Sal vs. (2R,6R)-HNK (0.075) | — | — | 0.9955 | — | |
| | | | Sal vs. (2R,6R)-HNK (0.1) | — | — | 0.9257 | — | |
| | | | Sal vs. (2R,6R)-HNK (0.3) | — | — | 0.9993 | — | |
| | | | Sal vs. (2R,6R)-HNK (2.5) | — | — | 0.6274 | — | |
| | | | Sal vs. (2R,6R)-HNK (10) | — | — | 0.9991 | — | |
| | | | Sal vs. (2S,6S)-HNK (0.025) | — | — | 0.9898 | — | 1D |
| | | | Sal vs. (2S,6S)-HNK (0.075) | — | — | 0.4829 | — | |
| | | | Sal vs. (2S,6S)-HNK (0.1) | — | — | 0.9999 | — | |
| | | | Sal vs. (2S,6S)-HNK (0.3) | — | — | 0.1973 | — | |
| | | | Sal vs. (2S,6S)-HNK (2.5) | — | — | 0.9996 | — | |
| | | | Sal vs. (2S,6S)-HNK (10) | — | — | 0.9896 | — | |
| Forced Swim Test Day 2 | Immobility Time (min 1-6) | RMANOVA | Drug | 3.355 | 15,805 | <0.0001 | *** | |
| | | | Time | 32.974 | 5,805 | <0.0001 | *** | |
| | | | Drug × Time | 2.550 | 75,805 | <0.0001 | *** | |
| | | Dunnett test | Sal vs. K (2.5) | — | — | 0.8314 | — | |
| | | | Sal vs. K (10) | — | — | 0.0006 | ** | |
| | | | Sal vs. K (30) | — | — | 0.1741 | — | |
| | | | Sal vs. (2R,6R)-HNK (0.025) | — | — | 0.0001 | *** | |
| | | | Sal vs. (2R,6R)-HNK (0.075) | — | — | 0.5537 | — | |
| | | | Sal vs. (2R,6R)-HNK (0.1) | — | — | 0.9871 | — | |
| | | | Sal vs. (2R,6R)-HNK (0.3) | — | — | 0.9996 | — | |
| | | | Sal vs. (2R,6R)-HNK (2.5) | — | — | 0.6589 | — | |
| | | | Sal vs. (2R,6R)-HNK (10) | — | — | 0.9950 | — | |
| | | | Sal vs. (2S,6S)-HNK (0.025) | — | — | 0.9996 | — | |
| | | | Sal vs. (2S,6S)-HNK (0.075) | — | — | 0.0025 | ** | |
| | | | Sal vs. (2S,6S)-HNK (0.1) | — | — | 0.2191 | — | |
| | | | Sal vs. (2S,6S)-HNK (0.3) | — | — | 0.9993 | — | |
| | | | Sal vs. (2S,6S)-HNK (2.5) | — | — | 0.5400 | — | |
| | | | Sal vs. (2S,6S)-HNK (10) | — | — | >0.9999 | — | |
| | Immobility Time (min 1) | ANOVA Dunnett test | Drug | 4.322 | 15,161 | <0.0001 | *** | |
| | | | Sal vs. K (2.5) | — | — | 0.5849 | — | |
| | | | Sal vs. K (10) | — | — | 0.0825 | — | |
| | | | Sal vs. K (30) | — | — | 0.9167 | — | |
| | | | Sal vs. (2R,6R)-HNK (0.025) | — | — | 0.0833 | — | |
| | | | Sal vs. (2R,6R)-HNK (0.075) | — | — | 0.4238 | — | |
| | | | Sal vs. (2R,6R)-HNK (0.1) | — | — | 0.9995 | — | |
| | | | Sal vs. (2R,6R)-HNK (0.3) | — | — | 0.9998 | — | |

TABLE 1-1-continued

Statistical analysis - Cohort: 1 week prophylactic drug

| Behavioral Paradigm | Measurement | Statistical Test | Comparison | F | ° of freedom | p | * | FIG. |
|---|---|---|---|---|---|---|---|---|
| | | | Sal vs. (2R,6R)-HNK (2.5) | — | — | 0.4807 | — | |
| | | | Sal vs. (2R,6R)-HNK (10) | — | — | 0.9997 | — | |
| | | | Sal vs. (2S,6S)-HNK (0.025) | — | — | 0.9954 | — | |
| | | | Sal vs. (2S,6S)-HNK (0.075) | — | — | 0.9993 | — | |
| | | | Sal vs. (2S,6S)-HNK (0.1) | — | — | 0.0291 | * | |
| | | | Sal vs. (2S,6S)-HNK (0.3) | — | — | 0.2627 | — | |
| | | | Sal vs. (2S,6S)-HNK (2.5) | — | — | 0.9998 | — | |
| | | | Sal vs. (2S,6S)-HNK (10) | — | — | 0.6616 | — | |
| | Immobility Time (min 2) | ANOVA Dunnett test | Drug | 2.941 | 15,161 | 0.0004 | ** | |
| | | | Sal vs. K (2.5) | — | — | 0.9770 | — | |
| | | | Sal vs. K (10) | — | — | 0.0675 | — | |
| | | | Sal vs. K (30) | — | — | 0.7390 | — | |
| | | | Sal vs. (2R,6R)-HNK (0.025) | — | — | 0.5867 | — | |
| | | | Sal vs. (2R,6R)-HNK (0.075) | — | — | 0.9312 | — | |
| | | | Sal vs. (2R,6R)-HNK (0.1) | — | — | 0.2508 | — | |
| | | | Sal vs. (2R,6R)-HNK (0.3) | — | — | 0.9999 | — | |
| | | | Sal vs. (2R,6R)-HNK (2.5) | — | — | 0.9193 | — | |
| | | | Sal vs. (2R,6R)-HNK (10) | — | — | 0.9993 | — | |
| | | | Sal vs. (2S,6S)-HNK (0.025) | — | — | 0.9993 | — | |
| | | | Sal vs. (2S,6S)-HNK (0.075) | — | — | 0.9998 | — | |
| | | | Sal vs. (2S,6S)-HNK (0.1) | — | — | 0.4741 | — | |
| | | | Sal vs. (2S,6S)-HNK (0.3) | — | — | 0.7509 | — | |
| | | | Sal vs. (2S,6S)-HNK (2.5) | — | — | >0.9999 | — | |
| | | | Sal vs. (2S,6S)-HNK (10) | — | — | 0.9991 | — | |
| | Immobility Time (min 3) | ANOVA | Drug | 1.316 | 15,161 | 0.1981 | — | |
| | Immobility Time (min 4) | ANOVA Dunnett test | Drug | 2.323 | 15,161 | 0.0050 | ** | |
| | | | Sal vs. K (2.5) | — | — | 0.9997 | — | |
| | | | Sal vs. K (10) | — | — | 0.0144 | * | |
| | | | Sal vs. K (30) | — | — | 0.4082 | — | |
| | | | Sal vs. (2R,6R)-HNK (0.025) | — | — | 0.0383 | * | |
| | | | Sal vs. (2R,6R)-HNK (0.075) | — | — | 0.9993 | — | |
| | | | Sal vs. (2R,6R)-HNK (0.1) | — | — | 0.9994 | — | |
| | | | Sal vs. (2R,6R)-HNK (0.3) | — | — | 0.9883 | — | |
| | | | Sal vs. (2R,6R)-HNK (2.5) | — | — | 0.9991 | — | |
| | | | Sal vs. (2R,6R)-HNK (10) | — | — | 0.9955 | — | |
| | | | Sal vs. (2S,6S)-HNK (0.025) | — | — | 0.9518 | — | |
| | | | Sal vs. (2S,6S)-HNK (0.075) | — | — | 0.3169 | — | |
| | | | Sal vs. (2S,6S)-HNK (0.1) | — | — | 0.9995 | — | |
| | | | Sal vs. (2S,6S)-HNK (0.3) | — | — | 0.9997 | — | |
| | | | Sal vs. (2S,6S)-HNK (2.5) | — | — | 0.8764 | — | |
| | | | Sal vs. (2S,6S)-HNK (10) | — | — | 0.9999 | — | |
| | Immobility Time (min 5) | ANOVA Dunnett test | Drug | 3.333 | 15,161 | <0.0001 | *** | |
| | | | Sal vs. K (2.5) | — | — | 0.9999 | — | |
| | | | Sal vs. K (10) | — | — | 0.0149 | * | |
| | | | Sal vs. K (30) | — | — | 0.3770 | — | |
| | | | Sal vs. (2R,6R)-HNK (0.025) | — | — | 0.0346 | * | |
| | | | Sal vs. (2R,6R)-HNK (0.075) | — | — | >0.9999 | — | |
| | | | Sal vs. (2R,6R)-HNK (0.1) | — | — | 0.8037 | — | |
| | | | Sal vs. (2R,6R)-HNK (0.3) | — | — | 0.9991 | — | |
| | | | Sal vs. (2R,6R)-HNK (2.5) | — | — | >0.9999 | — | |
| | | | Sal vs. (2R,6R)-HNK (10) | — | — | 0.9991 | — | |
| | | | Sal vs. (2S,6S)-HNK (0.025) | — | — | 0.9885 | — | |
| | | | Sal vs. (2S,6S)-HNK (0.075) | — | — | <0.0001 | *** | |
| | | | Sal vs. (2S,6S)-HNK (0.1) | — | — | 0.9990 | — | |
| | | | Sal vs. (2S,6S)-HNK (0.3) | — | — | 0.9882 | — | |
| | | | Sal vs. (2S,6S)-HNK (2.5) | — | — | 0.6601 | — | |
| | | | Sal vs. (2S,6S)-HNK (10) | — | — | 0.9877 | — | |
| | Immobility Time (min 6) | ANOVA Dunnett test | Drug | 3.140 | 15,161 | 0.0002 | ** | |
| | | | Sal vs. K (2.5) | — | — | 0.9686 | — | |
| | | | Sal vs. K (10) | — | — | 0.3306 | — | |
| | | | Sal vs. K (30) | — | — | 0.8643 | — | |
| | | | Sal vs. (2R,6R)-HNK (0.025) | — | — | 0.2356 | — | |
| | | | Sal vs. (2R,6R)-HNK (0.075) | — | — | 0.9760 | — | |
| | | | Sal vs. (2R,6R)-HNK (0.1) | — | — | 0.8172 | — | |
| | | | Sal vs. (2R,6R)-HNK (0.3) | — | — | 0.9991 | — | |
| | | | Sal vs. (2R,6R)-HNK (2.5) | — | — | 0.9995 | — | |
| | | | Sal vs. (2R,6R)-HNK (10) | — | — | 0.9999 | — | |
| | | | Sal vs. (2S,6S)-HNK (0.025) | — | — | >0.9999 | — | |
| | | | Sal vs. (2S,6S)-HNK (0.075) | — | — | 0.0013 | ** | |
| | | | Sal vs. (2S,6S)-HNK (0.1) | — | — | 0.9952 | — | |
| | | | Sal vs. (2S,6S)-HNK (0.3) | — | — | 0.4546 | — | |
| | | | Sal vs. (2S,6S)-HNK (2.5) | — | — | 0.9992 | — | |
| | | | Sal vs. (2S,6S)-HNK (10) | — | — | 0.9994 | — | |

TABLE 1-1-continued

| Statistical analysis - Cohort: 1 week prophylactic drug | | | | | | | | |
|---|---|---|---|---|---|---|---|---|
| Behavioral Paradigm | Measurement | Statistical Test | Comparison | F | ° of freedom | p | * | FIG. |
| | Immobility Time Average (min 3-6) | ANOVA | Drug | 3.584 | 15,161 | 0.0001 | *** | 1E |
| | | Dunnett test | Sal vs. K (2.5) | — | — | 0.9990 | — | 1E |
| | | | Sal vs. K (10) | — | — | 0.0062 | ** | |
| | | | Sal vs. K (30) | — | — | 0.5537 | — | |
| | | | Sal vs. (2R,6R)-HNK (0.025) | — | — | 0.0229 | * | 1F |
| | | | Sal vs. (2R,6R)-HNK (0.075) | — | — | 0.8615 | — | |
| | | | Sal vs. (2R,6R)-HNK (0.1) | — | — | 0.9994 | — | |
| | | | Sal vs. (2R,6R)-HNK (0.3) | — | — | 0.9994 | — | |
| | | | Sal vs. (2R,6R)-HNK (2.5) | — | — | 0.9507 | — | |
| | | | Sal vs. (2R,6R)-HNK (10) | — | — | 0.9997 | — | |
| | | | Sal vs. (2S,6S)-HNK (0.025) | — | — | 0.9999 | — | 1G |
| | | | Sal vs. (2S,6S)-HNK (0.075) | — | — | 0.9990 | — | |
| | | | Sal vs. (2S,6S)-HNK (0.1) | — | — | 0.9623 | — | |
| | | | Sal vs. (2S,6S)-HNK (0.3) | — | — | 0.9999 | — | |
| | | | Sal vs. (2S,6S)-HNK (2.5) | — | — | 0.9957 | — | |
| | | | Sal vs. (2S,6S)-HNK (10) | — | — | 0.9999 | — | |
| Open Field | Distance Travelled (min 1-10) | RMANOVA | Drug | 0.530 | 2,108 | 0.6017 | — | 1H |
| | | | Distance | 21.192 | 9,108 | <0.0001 | *** | |
| | | | Drug × Distance | 1.746 | 18,108 | 0.0419 | * | |
| | Distance Travelled (min 1) | ANOVA | Drug | 0.281 | 2,12 | 0.7600 | — | |
| | Distance Travelled (min 2) | ANOVA | Drug | 1.909 | 2,12 | 0.1906 | — | |
| | Distance Travelled (min 3) | ANOVA | Drug | 3.594 | 2,12 | 0.0598 | — | |
| | Distance Travelled (min 4) | ANOVA | Drug | 0.842 | 2,12 | 0.4550 | — | |
| | Distance Travelled (min 5) | ANOVA | Drug | 0.480 | 2,12 | 0.6299 | — | |
| | Distance Travelled (min 6) | ANOVA | Drug | 1.546 | 2,12 | 0.2526 | — | |
| | Distance Travelled (min 7) | ANOVA | Drug | 0.794 | 2,12 | 0.4745 | — | |
| | Distance Travelled (min 8) | ANOVA | Drug | 0.781 | 2,12 | 0.4799 | — | |
| | Distance Travelled (min 9) | ANOVA | Drug | 1.575 | 2,12 | 0.2469 | — | |
| | Distance Travelled (min 10) | ANOVA | Drug | 2.646 | 2,12 | 0.1117 | — | |
| | Distance Travelled Average (min 1-10) | ANOVA | Drug | 0.530 | 2,12 | 0.6017 | — | |
| | Time in Center/ (Time in Center + Time in Periphery) | ANOVA | Drug | 0.295 | 2,12 | 0.7500 | — | 1I |
| Tail Immersion Test | Withdrawal Latency | ANOVA | Drug | 2.689 | 2,12 | 0.1084 | — | 1J |

TABLE 1-2

Statistical analysis

| Cohort/Behavioral Paradigm | Measurement | Statistical Test | Comparison | F | ° of freedom | p | * | FIG. |
|---|---|---|---|---|---|---|---|---|
| 3 day prophylactic drug/Forced Swim Test Day 2 | Immobility Time (min 1-6) | RMANOVA | Drug | 14.215 | 4,125 | <0.0001 | *** | 2B |
| | | | Time | 3.300 | 5,125 | 0.0078 | ** | |
| | | | Drug × Time | 1.512 | 20,125 | 0.0883 | — | |
| | | Fisher's PLSD | Sal vs. K (2.5) | — | — | 0.1441 | — | |
| | | | Sal vs. K (10) | — | — | 0.1807 | — | |
| | | | Sal vs. K (30) | — | — | 0.0750 | — | |
| | | | Sal vs. (2R,6R)-HNK (0.025) | — | — | <0.0001 | *** | |
| | Immobility Time Average (min 3-6) | ANOVA | Drug | 7.868 | 4,25 | 0.0003 | *** | 2C |
| | | Fisher's PLSD | Sal vs. K (2.5) | — | — | 0.3992 | — | |
| | | | Sal vs. K (10) | — | — | 0.4394 | — | |
| | | | Sal vs. K (30) | — | — | 0.3050 | — | |
| | | | Sal vs. (2R,6R)-HNK (0.025) | — | — | 0.0046 | ** | |
| 24 hour prophylactic drug/Forced Swim Test Day 2 | Immobility Time (min 1-6) | RMANOVA | Drug | 2.102 | 1,85 | 0.1653 | — | 2E |
| | | | Time | 6.780 | 5,85 | <0.0001 | *** | |
| | | | Drug × Time | 1.123 | 5,85 | 0.3544 | — | |
| | Immobility Time Average (min 3-6) | t-test | Sal vs. (2R,6R)-HNK (0.025) | — | — | 0.1367 | — | 2F |

TABLE 1-3

Statistical analysis - Cohort: 1 week prophylactic drug, chronic immobilization stress

| Behavioral Paradigm | Measurement | Statistical Test | Comparison | F | ° of freedom | p | * | FIG. |
|---|---|---|---|---|---|---|---|---|
| Forced Swim Test Day 1 | Immobility Time (min 1-6) | RMANOVA | Drug | 64.951 | 2,130 | <0.0001 | *** | |
| | | | Time | 12.521 | 5,130 | <0.0001 | *** | |
| | | | Drug × Time | 2.932 | 10,130 | 0.0024 | ** | |
| | Immobility Time (min 1) | ANOVA | Drug | 42.952 | 2,26 | <0.0001 | *** | |
| | | Fisher's PLSD | Sal vs. K (10) | — | — | 0.1619 | — | |
| | | | Sal vs. (2R,6R)-HNK (0.025) | — | — | <0.0001 | *** | |
| | Immobility Time (min 2) | ANOVA | Drug | 16.868 | 2,26 | <0.0001 | *** | |
| | | Fisher's PLSD | Sal vs. K (10) | — | — | 0.4051 | — | |
| | | | Sal vs. (2R,6R)-HNK (0.025) | — | — | <0.0001 | *** | |
| | Immobility Time (min 3) | ANOVA | Drug | 28.216 | 2,26 | <0.0001 | *** | |
| | | Fisher's PLSD | Sal vs. K (10) | — | — | 0.5575 | — | |
| | | | Sal vs. (2R,6R)-HNK (0.025) | — | — | <0.0001 | *** | |
| | Immobility Time (min 4) | ANOVA | Drug | 37.689 | 2,26 | <0.0001 | *** | |
| | | Fisher's PLSD | Sal vs. K (10) | — | — | 0.4015 | — | |
| | | | Sal vs. (2R,6R)-HNK (0.025) | — | — | <0.0001 | *** | |
| | Immobility Time (min 5) | ANOVA | Drug | 77.031 | 2,26 | <0.0001 | *** | |
| | | Fisher's PLSD | Sal vs. K (10) | — | — | 0.4985 | — | |
| | | | Sal vs. (2R,6R)-HNK (0.025) | — | — | <0.0001 | *** | |
| | Immobility Time (min 6) | ANOVA | Drug | 45.781 | 2,26 | <0.0001 | *** | |
| | | Fisher's PLSD | Sal vs. K (10) | — | — | 0.0022 | ** | |
| | | | Sal vs. (2R,6R)-HNK (0.025) | — | — | <0.0001 | *** | |
| | Immobility Time Average (min 1-6) | ANOVA | Drug | 79.304 | 2,26 | <0.0001 | *** | |
| | | Fisher's PLSD | Sal vs. K (10) | — | — | 0.1873 | — | |
| | | | Sal vs. (2R,6R)-HNK (0.025) | — | — | <0.0001 | *** | |
| Forced Swim Test Day 2 | Immobility Time (min 1-6) | RMANOVA | Drug | 8.249 | 2,130 | 0.0017 | ** | 3B |
| | | | Time | 13.472 | 5,130 | <0.0001 | *** | |
| | | | Drug × Time | 3.528 | 10,130 | 0.0004 | ** | |
| | Immobility Time (min 1) | ANOVA | Drug | 11.980 | 2,26 | 0.0002 | ** | |
| | | Fisher's PLSD | Sal vs. K (10) | — | — | 0.0533 | — | |
| | | | Sal vs. (2R,6R)-HNK (0.025) | — | — | 0.0073 | ** | |
| | Immobility Time (min 2) | ANOVA | Drug | 3.732 | 2,26 | 0.0376 | * | |
| | | Fisher's PLSD | Sal vs. K (10) | — | — | 0.0325 | * | |
| | | | Sal vs. (2R,6R)-HNK (0.025) | — | — | 0.8092 | — | |
| | Immobility Time (min 3) | ANOVA | Drug | 2.831 | 2,26 | 0.0772 | — | |
| | Immobility Time (min 4) | ANOVA | Drug | 1.966 | 2,26 | 0.1603 | — | |
| | Immobility Time (min 5) | ANOVA | Drug | 6.865 | 2,26 | 0.0040 | ** | |
| | | Fisher's PLSD | Sal vs. K (10) | — | — | 0.0011 | ** | |
| | | | Sal vs. (2R,6R)-HNK (0.025) | — | — | 0.0328 | * | |
| | Immobility Time (min 6) | ANOVA | Drug | 8.412 | 2,26 | 0.0015 | ** | |
| | | Fisher's PLSD | Sal vs. K (10) | — | — | 0.0006 | ** | |
| | | | Sal vs. (2R,6R)-HNK (0.025) | — | — | 0.0069 | ** | |

TABLE 1-3-continued

Statistical analysis - Cohort: 1 week prophylactic drug, chronic immobilization stress

| Behavioral Paradigm | Measurement | Statistical Test | Comparison | F | ° of freedom | p | * | FIG. |
|---|---|---|---|---|---|---|---|---|
| | Immobility Time Average (min 3-6) | ANOVA Fisher's PLSD | Drug | 8.115 | 2,26 | 0.0018 | ** | 3C |
| | | | Sal vs. K (10) | — | — | 0.0005 | ** | |
| | | | Sal vs. (2R,6R)-HNK (0.025) | — | — | 0.0177 | * | |
| Contextual Fear Conditioning Training | Freezing (min 1-5) | RMANOVA | Drug | 1.065 | 2,104 | 0.3592 | — | 3D |
| | | | Time | 55.948 | 4,104 | <0.0001 | *** | |
| | | | Drug × Time | 0.529 | 8,104 | 0.8323 | — | |
| Contextual Fear Conditioning Re-exposure | Freezing (min 1-5) | RMANOVA | Drug | 0.913 | 2,104 | 0.4140 | — | 3E |
| | | | Time | 15.611 | 4,104 | <0.0001 | *** | |
| | | | Drug × Time | 1.048 | 8,104 | 0.4056 | — | |
| | Freezing Average (min 1-5) | ANOVA | Drug | 0.913 | 2,26 | 0.4140 | — | 3F |

TABLE 1-4

Statistical analysis - Cohort: 1 week prophylactic drug, learned helplessness stress

| Behavioral Paradigm | Measurement | Statistical Test | Comparison | F | ° of freedom | p | * | FIG. |
|---|---|---|---|---|---|---|---|---|
| Learned Helplessness | Session Length | ANOVA | Drug | 1.021 | 2,35 | 0.3707 | — | 4B |
| | Escape Latency (trials 11-30) | RMANOVA | Drug | 1.120 | 2,665 | 0.3377 | — | 4C |
| | | | Trial | 3.970 | 19,665 | <0.0001 | *** | |
| | | | Drug × Trial | 0.872 | 38,665 | 0.6914 | — | |
| | Escape Latency Average (trials 11-30) | ANOVA | Drug | 0.657 | 2,53 | 0.5248 | — | 4D |
| Forced Swim Test Day 2 | Immobility Time (min 1-6) | RMANOVA | Drug | 16.452 | 2,130 | <0.0001 | *** | 4E |
| | | | Time | 14.876 | 5,130 | <0.0001 | *** | |
| | | | Drug × Time | 0.701 | 10,130 | 0.7218 | — | |
| | Immobility Time Average (min 3-6) | ANOVA Fisher's PLSD | Drug | 15.061 | 2,26 | <0.0001 | *** | 4F |
| | | | Sal vs. K (10) | — | — | <0.0001 | *** | |
| | | | Sal vs. (2R,6R)-HNK (0.025) | — | — | <0.0001 | *** | |
| Elevated Plus Maze | Time in Open Arms Average (min 1-6) | ANOVA Fisher's PLSD | Drug | 5.438 | 2,12 | 0.0208 | * | 4G |
| | | | Sal vs. K (10) | — | — | 0.0147 | * | |
| | | | Sal vs. (2R,6R)-HNK (0.025) | — | — | 0.9855 | — | |
| | Time in Closed Arms Average (min 1-6) | ANOVA Fisher's PLSD | Drug | 3.777 | 2,12 | 0.0534 | — | 4H |
| | | | Sal vs. K (10) | — | — | 0.0186 | * | |
| | | | Sal vs. (2R,6R)-HNK (0.025) | — | — | 0.3285 | — | |
| | Time in Center Average (min 1-6) | ANOVA | Drug | 0.826 | 2,12 | 0.4612 | — | 4I |

TABLE 1-5

Statistical analysis

| Cohort/ Behavioral Paradigm | Measurement | Statistical Test | Comparison | F | ° of freedom | p | * | FIG. |
|---|---|---|---|---|---|---|---|---|
| Ovariectomized, 1 week prophylactic drug/Forced Swim Test Day 2 | Immobility Time (min 1-6) | RMANOVA | Surgery | 0.806 | 1,385 | 0.3721 | — | 5B |
| | | | Drug | 4.979 | 2,385 | 0.0093 | ** | |
| | | | Time | 30.320 | 5,385 | <0.0001 | *** | |
| | | | Surgery × Time | 1.867 | 5,385 | 0.0992 | — | |
| | | | Drug × Time | 1.614 | 10,385 | 0.1003 | — | |
| | | | Surgery × Drug × Time | 1.498 | 10,385 | 0.1376 | — | |
| | Immobility Time Average (min 3-6) | ANOVA | Surgery | 1.486 | 1,77 | 0.2265 | — | 5C |
| | | | Drug | 2.692 | 2,77 | 0.0741 | — | |
| | | | Surgery × Drug | 3.183 | 2,77 | 0.0470 | * | |
| | | Fisher's PLSD | Sham Sal vs. Sham K (10) | — | — | 0.0405 | * | |
| | | | Sham Sal vs. Sham (2R,6R)-HNK (0.025) | — | — | 0.0099 | ** | |
| | | | OVX Sal vs. OVX K (10) | — | — | 0.7305 | — | |
| | | | OVX Sal vs. OVX (2R,6R)-HNK (0.025) | — | — | 0.9445 | — | |
| | | | Sham Sal vs. OVX Sal | — | — | 0.1111 | — | |
| | | | Sham K (10) vs. OVX K (10) | — | — | 0.2375 | — | |
| | | | Sham (2R,6R)-HNK (0.025) vs. OVX (2R,6R)-HNK (0.025 | — | — | 0.0476 | * | |

TABLE 1-5-continued

Statistical analysis

| Cohort/ Behavioral Paradigm | Measurement | Statistical Test | Comparison | F | ° of freedom | p | * | FIG. |
|---|---|---|---|---|---|---|---|---|
| Ovariectomized, E2/P4 replacement, 1 week prophylactic drug/Forced Swim Test Day 2 | Immobility Time (min 1-6) | RMANOVA | Hormone | 18.403 | 1,300 | <0.0001 | *** | 5E |
| | | | Drug | 3.725 | 2,300 | 0.0299 | * | |
| | | | Time | 40.571 | 5,300 | <0.0001 | *** | |
| | | | Hormone × Time | 0.680 | 5,300 | 0.6391 | — | |
| | | | Drug × Time | 0.741 | 10,300 | 0.6853 | — | |
| | | | Hormone × Drug × Time | 0.862 | 10,300 | 0.5692 | — | |
| | Immobility Time Average (min 3-6) | ANOVA | Hormone | 20.215 | 1,60 | <0.0001 | *** | 5F |
| | | | Drug | 3.766 | 2,60 | 0.0288 | * | |
| | | | Hormone × Drug | 3.961 | 2,60 | 0.0242 | * | |
| | | Fisher's PLSD | Vehicle Sal vs. Vehicle K (10) | — | — | 0.9193 | — | |
| | | | Vehicle Sal vs. Vehicle (2R,6R)-HNK (0.025) | — | — | 0.6287 | — | |
| | | | E2/P4 Sal vs. E2/P4 K (10) | — | — | 0.0196 | * | |
| | | | E2/P4 Sal vs. E2/P4 (2R,6R)-HNK (0.025) | — | — | 0.0316 | * | |
| | | | Vehicle Sal vs. E2/P4 Sal | — | — | 0.5626 | — | |
| | | | Vehicle K (10) vs. E2/P4 K (10) | — | — | 0.0089 | ** | |
| | | | Vehicle (2R,6R)-HNK (0.025) vs. E2/P4 (2R,6R)-HNK (0.025) | — | — | 0.0013 | ** | |

TABLE 1-6

Statistical analysis - Cohort: 1 week prophylactic drug

| Behavioral Paradigm | Measurement | Statistical Test | Comparison | F | ° of freedom | p | * | FIG. |
|---|---|---|---|---|---|---|---|---|
| Contextual Fear Conditioning Training | Freezing (min 1-5) | RMANOVA | Drug | 3.479 | 15,644 | <0.0001 | *** | 6A, 6B, 6C |
| | | | Time | 381.842 | 4,644 | <0.0001 | *** | |
| | | | Drug × Time | 2.185 | 60,644 | <0.0001 | *** | |
| | | Dunnett test | Sal vs. K (2.5) | — | — | 0.5398 | — | |
| | | | Sal vs. K (10) | — | — | >0.9999 | — | |
| | | | Sal vs. K (30) | — | — | 0.9998 | — | |
| | | | Sal vs. (2R,6R)-HNK (0.025) | — | — | 0.7272 | — | |
| | | | Sal vs. (2R,6R)-HNK (0.075) | — | — | 0.9917 | — | |
| | | | Sal vs. (2R,6R)-HNK (0.1) | — | — | 0.6657 | — | |
| | | | Sal vs. (2R,6R)-HNK (0.3) | — | — | 0.9992 | — | |
| | | | Sal vs. (2R,6R)-HNK (2.5) | — | — | 0.9993 | — | |
| | | | Sal vs. (2R,6R)-HNK (10) | — | — | 0.1798 | — | |
| | | | Sal vs. (2S,6S)-HNK (0.025) | — | — | 0.9955 | — | |
| | | | Sal vs. (2S,6S)-HNK (0.075) | — | — | 0.9996 | — | |
| | | | Sal vs. (2S,6S)-HNK (0.1) | — | — | 0.2466 | — | |
| | | | Sal vs. (2S,6S)-HNK (0.3) | — | — | 0.0085 | ** | |
| | | | Sal vs. (2S,6S)-HNK (2.5) | — | — | 0.6733 | — | |
| | | | Sal vs. (2S,6S)-HNK (10) | — | — | 0.5049 | — | |
| | Freezing (min 1) | ANOVA | Drug | — | — | 0.4302 | — | |
| | Freezing (min 2) | ANOVA | Drug | — | — | 0.3866 | — | |
| | Freezing (min 3) | ANOVA | Drug | — | — | 0.1117 | — | |
| | Freezing (min 4) | ANOVA | Drug | 2.105 | 15,161 | 0.0120 | * | |
| | | Dunnett test | Sal vs. K (2.5) | — | — | 0.9957 | — | |
| | | | Sal vs. K (10) | — | — | 0.9996 | — | |
| | | | Sal vs. K (30) | — | — | >0.9999 | — | |
| | | | Sal vs. (2R,6R)-HNK (0.025) | — | — | 0.9640 | — | |
| | | | Sal vs. (2R,6R)-HNK (0.075) | — | — | 0.9911 | — | |
| | | | Sal vs. (2R,6R)-HNK (0.1) | — | — | >0.9999 | — | |
| | | | Sal vs. (2R,6R)-HNK (0.3) | — | — | 0.9477 | — | |
| | | | Sal vs. (2R,6R)-HNK (2.5) | — | — | 0.9991 | — | |
| | | | Sal vs. (2R,6R)-HNK (10) | — | — | 0.4387 | — | |
| | | | Sal vs. (2S,6S)-HNK (0.025) | — | — | 0.7894 | — | |
| | | | Sal vs. (2S,6S)-HNK (0.075) | — | — | 0.9991 | — | |
| | | | Sal vs. (2S,6S)-HNK (0.1) | — | — | 0.3064 | — | |
| | | | Sal vs. (2S,6S)-HNK (0.3) | — | — | 0.0675 | — | |
| | | | Sal vs. (2S,6S)-HNK (2.5) | — | — | 0.9438 | — | |
| | | | Sal vs. (2S,6S)-HNK (10) | — | — | 0.7737 | — | |
| | Freezing (min 5) | ANOVA | Drug | 2.809 | 15,161 | 0.0007 | ** | |
| | | Dunnett test | Sal vs. K (2.5) | — | — | 0.2720 | — | |
| | | | Sal vs. K (10) | — | — | 0.9996 | — | |
| | | | Sal vs. K (30) | — | — | 0.9997 | — | |

TABLE 1-6-continued

Statistical analysis - Cohort: 1 week prophylactic drug

| Behavioral Paradigm | Measurement | Statistical Test | Comparison | F | ° of freedom | p | * | FIG. |
|---|---|---|---|---|---|---|---|---|
| | | | Sal vs. (2R,6R)-HNK (0.025) | — | — | 0.9668 | — | |
| | | | Sal vs. (2R,6R)-HNK (0.075) | — | — | 0.9993 | — | |
| | | | Sal vs. (2R,6R)-HNK (0.1) | — | — | 0.2588 | — | |
| | | | Sal vs. (2R,6R)-HNK (0.3) | — | — | >0.9999 | — | |
| | | | Sal vs. (2R,6R)-HNK (2.5) | — | — | 0.9997 | — | |
| | | | Sal vs. (2R,6R)-HNK (10) | — | — | 0.3423 | — | |
| | | | Sal vs. (2S,6S)-HNK (0.025) | — | — | >0.9999 | — | |
| | | | Sal vs. (2S,6S)-HNK (0.075) | — | — | >0.9999 | — | |
| | | | Sal vs. (2S,6S)-HNK (0.1) | — | — | 0.5117 | — | |
| | | | Sal vs. (2S,6S)-HNK (0.3) | — | — | 0.0731 | — | |
| | | | Sal vs. (2S,6S)-HNK (2.5) | — | — | 0.7492 | — | |
| | | | Sal vs. (2S,6S)-HNK (10) | — | — | 0.5845 | — | |
| Contextual Fear Conditioning Re-exposure | Freezing (min 1-5) | RMANOVA | Drug | 2.360 | 15,644 | 0.0043 | ** | 6D, 6E, 6F |
| | | | Time | 74.210 | 4,644 | <0.0001 | *** | |
| | | | Drug × Time | 1.428 | 60,644 | 0.0222 | * | |
| | | Dunnett test | Sal vs. K (2.5) | — | — | 0.7546 | — | |
| | | | Sal vs. K (10) | — | — | 0.8986 | — | |
| | | | Sal vs. K (30) | — | — | 0.8647 | — | |
| | | | Sal vs. (2R,6R)-HNK (0.025) | — | — | 0.4341 | — | |
| | | | Sal vs. (2R,6R)-HNK (0.075) | — | — | 0.9955 | — | |
| | | | Sal vs. (2R,6R)-HNK (0.1) | — | — | 0.9257 | — | |
| | | | Sal vs. (2R,6R)-HNK (0.3) | — | — | 0.9993 | — | |
| | | | Sal vs. (2R,6R)-HNK (2.5) | — | — | 0.6274 | — | |
| | | | Sal vs. (2R,6R)-HNK (10) | — | — | 0.9991 | — | |
| | | | Sal vs. (2S,6S)-HNK (0.025) | — | — | 0.9898 | — | |
| | | | Sal vs. (2S,6S)-HNK (0.075) | — | — | 0.4829 | — | |
| | | | Sal vs. (2S,6S)-HNK (0.1) | — | — | 0.9999 | — | |
| | | | Sal vs. (2S,6S)-HNK (0.3) | — | — | 0.1973 | — | |
| | | | Sal vs. (25,6S)-HNK (2.5) | — | — | 0.9996 | — | |
| | | | Sal vs. (2S,6S)-HNK (10) | — | — | 0.9896 | — | |
| | Freezing (min 1) | ANOVA | Drug | 1.335 | 15,161 | 0.1866 | — | |
| | Freezing (min 2) | ANOVA | Drug | 2.517 | 15,161 | 0.0023 | ** | |
| | | Dunnett test | Sal vs. K (2.5) | — | — | 0.9996 | — | |
| | | | Sal vs. K (10) | — | — | 0.9240 | — | |
| | | | Sal vs. K (30) | — | — | 0.6079 | — | |
| | | | Sal vs. (2R,6R)-HNK (0.025) | — | — | 0.1669 | — | |
| | | | Sal vs. (2R,6R)-HNK (0.075) | — | — | >0.9999 | — | |
| | | | Sal vs. (2R,6R)-HNK (0.1) | — | — | 0.9990 | — | |
| | | | Sal vs. (2R,6R)-HNK (0.3) | — | — | 0.9998 | — | |
| | | | Sal vs. (2R,6R)-HNK (2.5) | — | — | 0.2365 | — | |
| | | | Sal vs. (2R,6R)-HNK (10) | — | — | 0.9994 | — | |
| | | | Sal vs. (2S,6S)-HNK (0.025) | — | — | >0.9999 | — | |
| | | | Sal vs. (2S,6S)-HNK (0.075) | — | — | 0.9135 | — | |
| | | | Sal vs. (2S,6S)-HNK (0.1) | — | — | 0.9997 | — | |
| | | | Sal vs. (2S,6S)-HNK (0.3) | — | — | 0.2064 | — | |
| | | | Sal vs. (2S,6S)-HNK (2.5) | — | — | 0.9991 | — | |
| | | | Sal vs. (2S,6S)-HNK (10) | — | — | 0.5764 | — | |
| | Freezing (min 3) | ANOVA | Drug | 2.380 | 15,161 | 0.0040 | ** | |
| | | Dunnett test | Sal vs. K (2.5) | — | — | 0.6267 | — | |
| | | | Sal vs. K (10) | — | — | 0.9864 | — | |
| | | | Sal vs. K (30) | — | — | 0.8139 | — | |
| | | | Sal vs. (2R,6R)-HNK (0.025) | — | — | 0.8139 | — | |
| | | | Sal vs. (2R,6R)-HNK (0.075) | — | — | 0.9009 | — | |
| | | | Sal vs. (2R,6R)-HNK (0.1) | — | — | 0.9333 | — | |
| | | | Sal vs. (2R,6R)-HNK (0.3) | — | — | 0.9954 | — | |
| | | | Sal vs. (2R,6R)-HNK (2.5) | — | — | 0.4707 | — | |
| | | | Sal vs. (2R,6R)-HNK (10) | — | — | 0.9074 | — | |
| | | | Sal vs. (2S,6S)-HNK (0.025) | — | — | 0.7775 | — | |
| | | | Sal vs. (2S,6S)-HNK (0.075) | — | — | 0.3091 | — | |
| | | | Sal vs. (2S,6S)-HNK (0.1) | — | — | 0.9998 | — | |
| | | | Sal vs. (2S,6S)-HNK (0.3) | — | — | 0.2280 | — | |
| | | | Sal vs. (2S,6S)-HNK (2.5) | — | — | 0.9908 | — | |
| | | | Sal vs. (2S,6S)-HNK (10) | — | — | 0.9993 | — | |
| | Freezing (min 4) | ANOVA | Drug | 2.338 | 15,161 | 0.0047 | ** | |
| | | Dunnett test | Sal vs. K (2.5) | — | — | 0.1951 | — | |
| | | | Sal vs. K (10) | — | — | 0.6904 | — | |
| | | | Sal vs. K (30) | — | — | 0.9885 | — | |
| | | | Sal vs. (2R,6R)-HNK (0.025) | — | — | 0.6797 | — | |
| | | | Sal vs. (2R,6R)-HNK (0.075) | — | — | 0.9994 | — | |
| | | | Sal vs. (2R,6R)-HNK (0.1) | — | — | 0.9679 | — | |
| | | | Sal vs. (2R,6R)-HNK (0.3) | — | — | 0.9994 | — | |
| | | | Sal vs. (2R,6R)-HNK (2.5) | — | — | 0.3440 | — | |
| | | | Sal vs. (2R,6R)-HNK (10) | — | — | 0.9994 | — | |
| | | | Sal vs. (2S,6S)-HNK (0.025) | — | — | 0.9990 | — | |

TABLE 1-6-continued

Statistical analysis - Cohort: 1 week prophylactic drug

| Behavioral Paradigm | Measurement | Statistical Test | Comparison | F | ° of freedom | p | * | FIG. |
|---|---|---|---|---|---|---|---|---|
| | | | Sal vs. (2S,6S)-HNK (0.075) | — | — | 0.5808 | — | |
| | | | Sal vs. (2S,6S)-HNK (0.1) | — | — | 0.9889 | — | |
| | | | Sal vs. (2S,6S)-HNK (0.3) | — | — | 0.8082 | — | |
| | | | Sal vs. (2S,6S)-HNK (2.5) | — | — | 0.9997 | — | |
| | | | Sal vs. (2S,6S)-HNK (10) | — | — | 0.9991 | — | |
| | Freezing (min 5) | ANOVA Dunnett test | Drug | 1.962 | 15,161 | 0.0210 | * | |
| | | | Sal vs. K (2.5) | — | — | 0.4912 | — | |
| | | | Sal vs. K (10) | — | — | 0.6667 | — | |
| | | | Sal vs. K (30) | — | — | 0.9996 | — | |
| | | | Sal vs. (2R,6R)-HNK (0.025) | — | — | 0.7607 | — | |
| | | | Sal vs. (2R,6R)-HNK (0.075) | — | — | 0.9990 | — | |
| | | | Sal vs. (2R,6R)-HNK (0.1) | — | — | 0.8119 | — | |
| | | | Sal vs. (2R,6R)-HNK (0.3) | — | — | 0.9991 | — | |
| | | | Sal vs. (2R,6R)-HNK (2.5) | — | — | 0.9997 | — | |
| | | | Sal vs. (2R,6R)-HNK (10) | — | — | 0.9003 | — | |
| | | | Sal vs. (2S,6S)-HNK (0.025) | — | — | 0.9996 | — | |
| | | | Sal vs. (2S,6S)-HNK (0.075) | — | — | 0.2703 | — | |
| | | | Sal vs. (2S,6S)-HNK (0.1) | — | — | >0.9999 | — | |
| | | | Sal vs. (2S,6S)-HNK (0.3) | — | — | 0.3262 | — | |
| | | | Sal vs. (2S,6S)-HNK (2.5) | — | — | >0.9999 | — | |
| | | | Sal vs. (2S,6S)-HNK (10) | — | — | >0.9999 | — | |
| Forced Swim Test Day 1 | Immobility Time (min 1-6) | RMANOVA | Drug | 3.050 | 15,795 | 0.0002 | ** | |
| | | | Time | 163.494 | 5,795 | <0.0001 | *** | |
| | | | Drug × Time | 3.003 | 75,795 | <0.0001 | *** | |
| | | Dunnett test | Sal vs. K (2.5) | — | — | 0.1415 | — | |
| | | | Sal vs. K (10) | — | — | 0.2256 | — | |
| | | | Sal vs. K (30) | — | — | 0.3435 | — | |
| | | | Sal vs. (2R,6R)-HNK (0.025) | — | — | 0.0090 | ** | |
| | | | Sal vs. (2R,6R)-HNK (0.075) | — | — | 0.2188 | — | |
| | | | Sal vs. (2R,6R)-HNK (0.1) | — | — | 0.0673 | — | |
| | | | Sal vs. (2R,6R)-HNK (0.3) | — | — | >0.9999 | — | |
| | | | Sal vs. (2R,6R)-HNK (2.5) | — | — | 0.7127 | — | |
| | | | Sal vs. (2R,6R)-HNK (10) | — | — | 0.9943 | — | |
| | | | Sal vs. (2S,6S)-HNK (0.025) | — | — | 0.8484 | — | |
| | | | Sal vs. (2S,6S)-HNK (0.075) | — | — | 0.0650 | — | |
| | | | Sal vs. (2S,6S)-HNK (0.1) | — | — | 0.5664 | — | |
| | | | Sal vs. (2S,6S)-HNK (0.3) | — | — | 0.0361 | * | |
| | | | Sal vs. (2S,6S)-HNK (2.5) | — | — | 0.9878 | — | |
| | | | Sal vs. (2S,6S)-HNK (10) | — | — | >0.9999 | — | |
| | Immobility Time (min 1) | ANOVA Dunnett test | Drug | 5.265 | 15,159 | <0.0001 | *** | |
| | | | Sal vs. K (2.5) | — | — | 0.9806 | — | |
| | | | Sal vs. K (10) | — | — | 0.9957 | — | |
| | | | Sal vs. K (30) | — | — | 0.9955 | — | |
| | | | Sal vs. (2R,6R)-HNK (0.025) | — | — | 0.9996 | — | |
| | | | Sal vs. (2R,6R)-HNK (0.075) | — | — | 0.0017 | ** | |
| | | | Sal vs. (2R,6R)-HNK (0.1) | — | — | 0.9996 | — | |
| | | | Sal vs. (2R,6R)-HNK (0.3) | — | — | 0.0586 | — | |
| | | | Sal vs. (2R,6R)-HNK (2.5) | — | — | 0.0026 | ** | |
| | | | Sal vs. (2R,6R)-HNK (10) | — | — | 0.0528 | — | |
| | | | Sal vs. (2S,6S)-HNK (0.025) | — | — | 0.0031 | ** | |
| | | | Sal vs. (2S,6S)-HNK (0.075) | — | — | 0.0820 | — | |
| | | | Sal vs. (2S,6S)-HNK (0.1) | — | — | <0.0001 | *** | |
| | | | Sal vs. (2S,6S)-HNK (0.3) | — | — | 0.0277 | * | |
| | | | Sal vs. (2S,6S)-HNK (2.5) | — | — | 0.0147 | * | |
| | | | Sal vs. (2S,6S)-HNK (10) | — | — | 0.0064 | ** | |
| | Immobility Time (min 2) | ANOVA | Drug | 1.728 | 15,159 | 0.0503 | — | |
| | Immobility Time (min 3) | ANOVA Dunnett test | Drug | 3.182 | 15,159 | 0.0001 | *** | |
| | | | Sal vs. K (2.5) | — | — | 0.9989 | — | |
| | | | Sal vs. K (10) | — | — | 0.0470 | * | |
| | | | Sal vs. K (30) | — | — | 0.1617 | — | |
| | | | Sal vs. (2R,6R)-HNK (0.025) | — | — | 0.9637 | — | |
| | | | Sal vs. (2R,6R)-HNK (0.075) | — | — | 0.9250 | — | |
| | | | Sal vs. (2R,6R)-HNK (0.1) | — | — | 0.4888 | — | |
| | | | Sal vs. (2R,6R)-HNK (0.3) | — | — | >0.9999 | — | |
| | | | Sal vs. (2R,6R)-HNK (2.5) | — | — | 0.9998 | — | |
| | | | Sal vs. (2R,6R)-HNK (10) | — | — | 0.6584 | — | |
| | | | Sal vs. (2S,6S)-HNK (0.025) | — | — | 0.9997 | — | |
| | | | Sal vs. (2S,6S)-HNK (0.075) | — | — | 0.9489 | — | |
| | | | Sal vs. (2S,6S)-HNK (0.1) | — | — | 0.9993 | — | |
| | | | Sal vs. (2S,6S)-HNK (0.3) | — | — | 0.4573 | — | |
| | | | Sal vs. (2S,6S)-HNK (2.5) | — | — | 0.9995 | — | |
| | | | Sal vs. (2S,6S)-HNK (10) | — | — | 0.9307 | — | |

TABLE 1-6-continued

| | | | Statistical analysis - Cohort: 1 week prophylactic drug | | | | | |
|---|---|---|---|---|---|---|---|---|
| Behavioral Paradigm | Measurement | Statistical Test | Comparison | F | ° of freedom | p | * | FIG. |
| | Immobility Time (min 4) | ANOVA Dunnett test | Drug | 2.260 | 15,159 | 0.0065 | ** | — |
| | | | Sal vs. K (2.5) | — | — | 0.9991 | — | |
| | | | Sal vs. K (10) | — | — | 0.3636 | — | |
| | | | Sal vs. K (30) | — | — | 0.9555 | — | |
| | | | Sal vs. (2R,6R)-HNK (0.025) | — | — | 0.8106 | — | |
| | | | Sal vs. (2R,6R)-HNK (0.075) | — | — | 0.9750 | — | |
| | | | Sal vs. (2R,6R)-HNK (0.1) | — | — | 0.3257 | — | |
| | | | Sal vs. (2R,6R)-HNK (0.3) | — | — | 0.7424 | — | |
| | | | Sal vs. (2R,6R)-HNK (2.5) | — | — | 0.9999 | — | |
| | | | Sal vs. (2R,6R)-HNK (10) | — | — | 0.5947 | — | |
| | | | Sal vs. (2S,6S)-HNK (0.025) | — | — | >0.9999 | — | |
| | | | Sal vs. (2S,6S)-HNK (0.075) | — | — | 0.9482 | — | |
| | | | Sal vs. (2S,6S)-HNK (0.1) | — | — | 0.9993 | — | |
| | | | Sal vs. (2S,6S)-HNK (0.3) | — | — | 0.8163 | — | |
| | | | Sal vs. (2S,6S)-HNK (2.5) | — | — | 0.9958 | — | |
| | | | Sal vs. (2S,6S)-HNK (10) | — | — | 0.9497 | — | |
| | Immobility Time (min 5) | ANOVA Dunnett test | Drug | 2.612 | 15,159 | 0.0015 | ** | |
| | | | Sal vs. K (2.5) | — | — | 0.9999 | — | |
| | | | Sal vs. K (10) | — | — | 0.2596 | — | |
| | | | Sal vs. K (30) | — | — | 0.8239 | — | |
| | | | Sal vs. (2R,6R)-HNK (0.025) | — | — | 0.8892 | — | |
| | | | Sal vs. (2R,6R)-HNK (0.075) | — | — | 0.8877 | — | |
| | | | Sal vs. (2R,6R)-HNK (0.1) | — | — | 0.2856 | — | |
| | | | Sal vs. (2R,6R)-HNK (0.3) | — | — | 0.3614 | — | |
| | | | Sal vs. (2R,6R)-HNK (2.5) | — | — | 0.9867 | — | |
| | | | Sal vs. (2R,6R)-HNK (10) | — | — | 0.6743 | — | |
| | | | Sal vs. (2S,6S)-HNK (0.025) | — | — | >0.9999 | — | |
| | | | Sal vs. (2S,6S)-HNK (0.075) | — | — | 0.9436 | — | |
| | | | Sal vs. (2S,6S)-HNK (0.1) | — | — | 0.9869 | — | |
| | | | Sal vs. (2S,6S)-HNK (0.3) | — | — | 0.9482 | — | |
| | | | Sal vs. (2S,6S)-HNK (2.5) | — | — | 0.9958 | — | |
| | | | Sal vs. (2S,6S)-HNK (10) | — | — | 0.9952 | — | |
| | Immobility Time (min 6) | ANOVA Dunnett test | Drug | 2.572 | 15,159 | 0.0018 | ** | |
| | | | Sal vs. K (2.5) | — | — | 0.9999 | — | |
| | | | Sal vs. K (10) | — | — | 0.1488 | — | |
| | | | Sal vs. K (30) | — | — | 0.8254 | — | |
| | | | Sal vs. (2R,6R)-HNK (0.025) | — | — | 0.6406 | — | |
| | | | Sal vs. (2R,6R)-HNK (0.075) | — | — | 0.9994 | — | |
| | | | Sal vs. (2R,6R)-HNK (0.1) | — | — | 0.9218 | — | |
| | | | Sal vs. (2R,6R)-HNK (0.3) | — | — | 0.9996 | — | |
| | | | Sal vs. (2R,6R)-HNK (2.5) | — | — | 0.9994 | — | |
| | | | Sal vs. (2R,6R)-HNK (10) | — | — | 0.1601 | — | |
| | | | Sal vs. (2S,6S)-HNK (0.025) | — | — | 0.9993 | — | |
| | | | Sal vs. (2S,6S)-HNK (0.075) | — | — | 0.6982 | — | |
| | | | Sal vs. (2S,6S)-HNK (0.1) | — | — | >0.9999 | — | |
| | | | Sal vs. (2S,6S)-HNK (0.3) | — | — | 0.6194 | — | |
| | | | Sal vs. (2S,6S)-HNK (2.5) | — | — | 0.9992 | — | |
| | | | Sal vs. (2S,6S)-HNK (10) | — | — | 0.5393 | — | |
| | Immobility Time Average (min 3-6) | ANOVA Dunnett test | Drug | 3.271 | 15,159 | <0.0001 | *** | |
| | | | Sal vs. K (2.5) | — | — | 0.9994 | — | |
| | | | Sal vs. K (10) | — | — | 0.0733 | — | |
| | | | Sal vs. K (30) | — | — | 0.5081 | — | |
| | | | Sal vs. (2R,6R)-HNK (0.025) | — | — | 0.7004 | — | |
| | | | Sal vs. (2R,6R)-HNK (0.075) | — | — | 0.9526 | — | |
| | | | Sal vs. (2R,6R)-HNK (0.1) | — | — | 0.3240 | — | |
| | | | Sal vs. (2R,6R)-HNK (0.3) | — | — | 0.9455 | — | |
| | | | Sal vs. (2R,6R)-HNK (2.5) | — | — | 0.9997 | — | |
| | | | Sal vs. (2R,6R)-HNK (10) | — | — | 0.3035 | — | |
| | | | Sal vs. (2S,6S)-HNK (0.025) | — | — | 0.9997 | — | |
| | | | Sal vs. (2S,6S)-HNK (0.075) | — | — | 0.7901 | — | |
| | | | Sal vs. (2S,6S)-HNK (0.1) | — | — | 0.9992 | — | |
| | | | Sal vs. (2S,6S)-HNK (0.3) | — | — | 0.5532 | — | |
| | | | Sal vs. (2S,6S)-HNK (2.5) | — | — | 0.9990 | — | |
| | | | Sal vs. (2S,6S)-HNK (10) | — | — | 0.8035 | — | |

TABLE 1-7

Statistical analysis

| Cohort/ Behavioral Paradigm | Measurement | Statistical Test | Comparison | F | ° of freedom | p | * | FIG. |
|---|---|---|---|---|---|---|---|---|
| 3 day prophylactic drug/ Contextual Fear Conditioning Training | Freezing (min 1-5) | RMANOVA | Drug | 4.539 | 4,100 | 0.0068 | ** | 7A |
| | | | Time | 113.383 | 4,100 | <0.0001 | *** | |
| | | | Drug x Time | 3.012 | 16,100 | 0.0004 | ** | |
| | Freezing (min 1) | ANOVA | Drug | 0.463 | 4,25 | 0.7622 | — | |
| | Freezing (min 2) | ANOVA | Drug | 0.720 | 4,25 | 0.5863 | — | |
| | Freezing (min 3) | ANOVA | Drug | 1.012 | 4,25 | 0.4199 | — | |
| | Freezing (min 4) | ANOVA | Drug | 1.903 | 4,25 | 0.1413 | — | |
| | Freezing (min 5) | ANOVA | Drug | 4.933 | 4,25 | 0.0045 | ** | |
| | | Fisher's PLSD | Sal vs. K (2.5) | — | — | 0.0143 | * | |
| | | | Sal vs. K (10) | — | — | 0.0078 | ** | |
| | | | Sal vs. K (30) | — | — | 0.0606 | — | |
| | | | Sal vs. (2R,6R)-HNK (0.025) | — | — | 0.9911 | — | |
| 3 day prophylactic drug/ Contextual Fear Conditioning Re-exposure | Freezing (min 1-5) | RMANOVA | Drug | 2.041 | 4,100 | 0.1193 | — | 7B |
| | | | Time | 11.504 | 4,100 | <0.0001 | *** | |
| | | | Drug x Time | 1.163 | 16,100 | 0.3110 | — | |
| | Freezing Average (min 1-5) | ANOVA | Drug | 2.041 | 4,25 | 0.1193 | — | 7C |
| 3 day prophylactic drug/Forced Swim Test Day 1 | Immobility Time (min 1-6) | RMANOVA | Drug | 11.903 | 4,125 | <0.0001 | *** | |
| | | | Time | 15.387 | 5,125 | <0.0001 | *** | |
| | | | Drug x Time | 6.709 | 20,125 | <0.0001 | *** | |
| | Immobility Time (min 1) | ANOVA Fisher's PLSD | Drug | 15.099 | 4,25 | <0.0001 | *** | |
| | | | Sal vs. K (2.5) | — | — | 0.9401 | — | |
| | | | Sal vs. K (10) | — | — | 0.9371 | — | |
| | | | Sal vs. K (30) | — | — | 0.6395 | — | |
| | | | Sal vs. (2R,6R)-HNK (0.025) | — | — | <0.0001 | *** | |
| | Immobility Time (min 2) | ANOVA Fisher's PLSD | Drug | 9.393 | 4,25 | <0.0001 | *** | |
| | | | Sal vs. K (2.5) | — | — | 0.6027 | — | |
| | | | Sal vs. K (10) | — | — | 0.5853 | — | |
| | | | Sal vs. K (30) | — | — | 0.9313 | — | |
| | | | Sal vs. (2R,6R)-HNK (0.025) | — | — | 0.0005 | ** | |
| | Immobility Time (min 3) | ANOVA Fisher's PLSD | Drug | 5.512 | 4,25 | 0.0025 | ** | |
| | | | Sal vs. K (2.5) | — | — | 0.5146 | — | |
| | | | Sal vs. K (10) | — | — | 0.7490 | — | |
| | | | Sal vs. K (30) | — | — | 0.7755 | — | |
| | | | Sal vs. (2R,6R)-HNK (0.025) | — | — | 0.0073 | ** | |
| | Immobility Time (min 4) | ANOVA Fisher's PLSD | Drug | 4.276 | 4,25 | 0.0090 | ** | |
| | | | Sal vs. K (2.5) | — | — | 0.9632 | — | |
| | | | Sal vs. K (10) | — | — | 0.6033 | — | |
| | | | Sal vs. K (30) | — | — | 0.5198 | — | |
| | | | Sal vs. (2R,6R)-HNK (0.025) | — | — | 0.0039 | ** | |
| | Immobility Time (min 5) | ANOVA Fisher's PLSD | Drug | 8.425 | 4,25 | 0.0002 | ** | |
| | | | Sal vs. K (2.5) | — | — | 0.6706 | — | |
| | | | Sal vs. K (10) | — | — | 0.9482 | — | |
| | | | Sal vs. K (30) | — | — | 0.9023 | — | |
| | | | Sal vs. (2R,6R)-HNK (0.025) | — | — | 0.0006 | ** | |
| | Immobility Time (min 6) | ANOVA Fisher's PLSD | Drug | 7.873 | 4,25 | 0.0003 | ** | |
| | | | Sal vs. K (2.5) | — | — | 0.7202 | — | |
| | | | Sal vs. K (10) | — | — | 0.9756 | — | |
| | | | Sal vs. K (30) | — | — | 0.5995 | — | |
| | | | Sal vs. (2R,6R)-HNK (0.025) | — | — | 0.0006 | ** | |
| | Immobility Time Average (min 3-6) | ANOVA Fisher's PLSD | Drug | 7.524 | 4,5 | 0.0004 | ** | |
| | | | Sal vs. K (2.5) | — | — | 0.6884 | — | |
| | | | Sal vs. K (10) | — | — | 0.9690 | — | |
| | | | Sal vs. K (30) | — | — | 0.8325 | — | |
| | | | Sal vs. (2R,6R)-HNK (0.025) | — | — | 0.0008 | ** | |
| 24 hour prophylactic drug/ Contextual Fear Conditioning | Freezing (min 1-5) | RMANOVA | Drug | 1.400 | 1,72 | 0.2522 | — | 7D |
| | | | Time | 80.926 | 4,72 | <0.0001 | *** | |
| | | | Drug x Time | 2.019 | 4,72 | 0.1008 | — | |
| 24 hour prophylactic drug/ | Freezing (min 1-5) | RMANOVA | Drug | 1.527 | 1,68 | 0.2334 | — | 7E |
| | | | Time | 6.065 | 4,68 | 0.0003 | ** | |
| | | | Drug x Time | 0.216 | 4,68 | 0.9289 | — | |

TABLE 1-7-continued

| Cohort/ Behavioral Paradigm | Measurement | Statistical Test | Comparison | F | ° of freedom | p | * | FIG. |
|---|---|---|---|---|---|---|---|---|
| Contextual Fear Conditioning Re-exposure | Freezing Average (min 1-5) | r-test | Sal vs. (2R,6R)-HNK (0.025) | — | — | 0.2334 | — | 7F |
| 24 hour prophylactic drug/Forced Swim Test Day 1 | Immobility Time (min 6) | RMANOVA | Drug | 0.349 | 1,85 | 0.5622 | — | |
| | | | Time | 14.149 | 5,85 | <0.0001 | *** | |
| | | | Drug x Time | 0.394 | 5,85 | 0.8516 | — | |
| | Immobility Time Average (min 3-6) | Z-test | Sal vs. (2R,6R)-HNK (0.025) | — | — | 0.5779 | — | |

TABLE 1-8

Statistical analysis - Cohort: 1 week prophylactic drug, learned helplessness stress

| Behavioral Paradigm | Measurement | Statistical Test | Comparison | F | ° of freedom | p | * | FIG. |
|---|---|---|---|---|---|---|---|---|
| Forced Swim Test Day 1 | Immobility Time (min 1-6) | RMANOVA | Drug | 19.929 | 2,130 | <0.0001 | *** | |
| | | | Time | 35.450 | 5,130 | <0.0001 | *** | |
| | | | Drug x Time | 0.909 | 10,130 | 0.5271 | — | |
| | Immobility Time (min 1) | ANOVA Fisher's PLSD | Drug | 12.035 | 2,26 | 0.0002 | ** | |
| | | | Sal vs. K (10) | — | — | <0.0001 | *** | |
| | | | Sal vs. (2R,6R)-HNK (0.025) | — | — | 0.0043 | ** | |
| | Immobility Time (min 2) | ANOVA Fisher's PLSD | Drug | 13.321 | 2,26 | 0.0001 | *** | |
| | | | Sal vs. K (10) | — | — | 0.0002 | ** | |
| | | | Sal vs. (2R,6R)-HNK (0.025) | — | — | <0.0001 | *** | |
| | Immobility Time (min 3) | ANOVA Fisher's PLSD | Drug | 12.643 | 2,26 | 0.0001 | *** | |
| | | | Sal vs. K (10) | — | — | 0.0002 | ** | |
| | | | Sal vs. (2R,6R)-HNK (0.025) | — | — | 0.0001 | *** | |
| | Immobility Time (min 4) | ANOVA Fisher's PLSD | Drug | 7.556 | 2,26 | 0.0026 | ** | |
| | | | Sal vs. K (10) | — | — | 0.0090 | ** | |
| | | | Sal vs. (2R,6R)-HNK (0.025) | — | — | 0.0009 | ** | |
| | Immobility Time (min 5) | ANOVA Fisher's PLSD | Drug | 10.148 | 2,26 | 0.0006 | ** | |
| | | | Sal vs. K (10) | — | — | 0.0016 | ** | |
| | | | Sal vs. (2R,6R)-HNK (0.025) | — | — | 0.0002 | ** | |
| | Immobility Time (min 6) | ANOVA Fisher's PLSD | Drug | 12.774 | 2,26 | 0.0001 | *** | |
| | | | Sal vs. K (10) | — | — | 0.0001 | *** | |
| | | | Sal vs. (2R,6R)-HNK (0.025) | — | — | 0.0002 | ** | |
| | Immobility Time Average (min 1-6) | ANOVA Fisher's PLSD | Drug | 15.039 | 2,26 | <0.0001 | *** | |
| | | | Sal vs. K (10) | — | — | <0.0001 | *** | |
| | | | Sal vs. (2R,6R)-HNK (0.025) | — | — | 0.0001 | *** | |
| Elevated Plus Maze | Time in Open Arms (min 1-6) | RMANOVA | Drug | 5.438 | 2,60 | 0.0208 | * | 8A |
| | | | Time | 1.840 | 5,60 | 0.1186 | — | |
| | | | Drug x Time | 0.661 | 10,60 | 0.7552 | — | |
| | Time in Closed Arms (min 1-6) | RMANOVA | Drug | 3.777 | 2,60 | 0.0534 | — | 8B |
| | | | Time | 2.235 | 5,60 | 0.0623 | — | |
| | | | Drug x Time | 0.547 | 10,60 | 0.8498 | — | |
| | Time in Center (min 1-6) | RMANOVA | Drug | 0.826 | 2,60 | 0.4612 | — | 8C |
| | | | Time | 0.783 | 5,60 | 0.5657 | — | |
| | | | Drug x Time | 0.645 | 10,60 | 0.7696 | — | |
| | Distance Travelled in Open Arms (min 1-6) | RMANOVA | Drug | 2.322 | 2,60 | 0.1404 | — | |
| | | | Distance | 2.373 | 5,60 | 0.0496 | * | |
| | | | Drug x Distance | 1.873 | 10,60 | 0.0671 | — | |
| | Distance Travelled in Open Arms Average (min 1-6) | ANOVA | Drug | 2.322 | 2,12 | 0.1404 | — | |
| | Distance Travelled in Closed Arms (min 1-6) | RMANOVA | Drug | 1.284 | 2,60 | 0.3125 | — | |
| | | | Distance | 2.866 | 5,60 | 0.0219 | * | |
| | | | Drug x Distance | 1.438 | 10,60 | 0.1860 | — | |
| | Distance Travelled in Closed Arms Average (min 1-6) | ANOVA | Drug | 1.284 | 2,12 | 0.3125 | — | |
| | Distance Travelled in | RMANOVA | Drug | 0.689 | 2,60 | 0.5207 | — | |
| | | | Distance | 1.778 | 5,60 | 0.1310 | — | |

TABLE 1-8-continued

Statistical analysis - Cohort: 1 week prophylactic drug, learned helplessness stress

| Behavioral Paradigm | Measurement | Statistical Test | Comparison | F | ° of freedom | p | * | FIG. |
|---|---|---|---|---|---|---|---|---|
| | Center (min 1-6) | | Drug x Distance | 0.658 | 10,60 | 0.7582 | — | |
| | Distance Travelled in Center Average (min 1-6) | ANOVA | Drug | 0.689 | 2,12 | 0.5207 | — | |
| | Entries into Open Arms Average (min 1-6) | ANOVA | Drug | 3.352 | 2,12 | 0.0697 | — | 8D |
| | Entries into Closed Arms Average (min 1-6) | ANOVA | Drug | 0.079 | 2,12 | 0.9249 | — | 8E |
| | Entries into Center Average (min 1-6) | ANOVA | Drug | 0.389 | 2,12 | 0.6860 | — | 8F |
| Contextual Fear Conditioning Training | Freezing (min 1-5) | RMANOVA | Drug | 1.293 | 2,104 | 0.2915 | — | 8G |
| | | | Time | 30.514 | 4,104 | <0.0001 | *** | |
| | | | Drug x Time | 0.234 | 8,104 | 0.9836 | — | |
| Contextual Fear Conditioning Re-exposure | Freezing (min 1-5) | RMANOVA | Drug | 0.106 | 2,104 | 0.9002 | — | 8H |
| | | | Time | 43.734 | 4,104 | <0.0001 | *** | |
| | | | Drug x Time | 3.297 | 8,104 | 0.0021 | ** | |
| | Freezing (min 1) | ANOVA Fisher's PLSD | Drug | 3.738 | 2,26 | 0.0374 | * | |
| | | | Sal vs. K (10) | — | — | 0.0166 | * | |
| | | | Sal vs. (2R,6R)-HNK (0.025) | — | — | 0.0399 | * | |
| | Freezing (min 2) | ANOVA | Drug | 0.167 | 2,26 | 0.8473 | — | |
| | Freezing (min 3) | ANOVA | Drug | 0.160 | 2,26 | 0.8531 | — | |
| | Freezing (min 4) | ANOVA | Drug | 1.444 | 2,26 | 0.2543 | — | |
| | Freezing (min 5) | ANOVA | Drug | 1.623 | 2,26 | 0.2166 | — | |
| | Freezing Average (min 1-5) | ANOVA | Drug | 0.106 | 2,26 | 0.9002 | — | 8I |

TABLE 1-9

Statistical analysis

| Cohort/ Behavioral Paradigm | Measurement | Statistical Test | Comparison | F | ° of freedom | p | * | FIG. |
|---|---|---|---|---|---|---|---|---|
| Antidepressant drug/Forced Swim Test Day 1 | Immobility Time (min 1-6) | RMANOVA | Drug | 0.095 | 2,60 | 0.9102 | — | 9B |
| | | | Time | 14.724 | 5,60 | <0.0001 | *** | |
| | | | Drug x Time | 1.257 | 10,60 | 0.2749 | — | |
| | Immobility Time Average (min 3-6) | ANOVA | Drug | 0.294 | 2,12 | 0.7503 | — | |
| Antidepressant drug/Forced Swim Test Day 2 | Immobility Time (min 1-6) | RMANOVA | Drug | 1.136 | 2,60 | 0.3532 | — | 9C |
| | | | Time | 20.037 | 5,60 | <0.0001 | *** | |
| | | | Drug x Time | 1.709 | 10,60 | 0.0996 | — | |
| | Immobility Time (min 1) | ANOVA Fisher's PLSD | Drug | 3.695 | 2,12 | 0.0562 | — | |
| | | | Sal vs. K (10) | — | — | 0.0187 | * | |
| | | | Sal vs. (2R,6R)-HNK (0.025) | — | — | 0.2184 | — | |
| | Immobility Time Average Min 3-6) | ANOVA | Drug | 0.577 | 2,12 | 0.5763 | — | 9D |
| Stress, antidepressant drug/Forced Swim Test Day 1 | Immobility Time (min 1-6) | RMANOVA | Drug | 0.088 | 2,50 | 0.9166 | — | 9F |
| | | | Time | 16.293 | 5,50 | <.0001 | *** | |
| | | | Drug x Time | 0.548 | 10,50 | 0.8473 | — | |
| | Immobility Time Average (min 3-6) | ANOVA | Drug | 0.047 | 2,10 | 0.9540 | — | |
| Stress, antidepressant drug/Forced Swim Test Day 2 | Immobility Time (min 1-6) | RMANOVA | Drug | 0.703 | 2,50 | 0.5182 | — | 9G |
| | | | Time | 4.107 | 5,50 | 0.0033 | ** | |
| | | | Drug x Time | 0.234 | 2,10 | 0.7957 | — | |
| | Immobility Time Average (min 3-6) | ANOVA | Drug | 0.922 | 10,50 | 0.5207 | — | 9H |

TABLE 1-9-continued

Statistical analysis

| Cohort/ Behavioral Paradigm | Measurement | Statistical Test | Comparison | F | ° of freedom | p | * | FIG. |
|---|---|---|---|---|---|---|---|---|
| Stress, antidepressant drug/ Contextual Fear Conditioning Training | Freezing (min 1-5) | RMANOVA | Drug | 3.866 | 2,40 | 0.0570 | — | 9I |
| | | | Time | 79.288 | 4,40 | <.0001 | *** | |
| | | | Drug x Time | 3.473 | 8,40 | 0.0039 | ** | |
| | | Fisher's PLSD | Sal vs. K (10) | — | — | 0.1932 | — | |
| | | | Sal vs. (2R,6R)-HNK (0.025) | — | — | 0.2199 | — | |
| | Freezing (min 1) | ANOVA | Drug | 1.154 | 2,10 | 0.3541 | — | |
| | Freezing (min 2) | ANOVA | Drug | 0.746 | 2,10 | 0.4990 | — | |
| | Freezing (min 3) | ANOVA | Drug | 0.982 | 2,10 | 0.4079 | — | |
| | Freezing (min 4) | ANOVA | Drug | 2.684 | 2,10 | 0.1166 | — | |
| | Freezing (min 5) | ANOVA | Drug | 5.475 | 2,10 | 0.0248 | * | |
| | | Fisher's PLSD | Sal vs. K (10) | — | — | 0.2639 | — | |
| | | | Sal vs. (2R,6R)-HNK (0.025) | — | — | 0.0731 | — | |
| Stress, antidepressant drug/ Contextual Fear Conditioning Re-exposure | Freezing (min 1-5) | RMANOVA | Drug | 0.129 | 2,40 | 0.8804 | — | 9J |
| | | | Time | 2.908 | 4,40 | 0.0334 | * | |
| | | | Drug x Time | 0.879 | 8,40 | 0.5420 | — | |
| | Freezing Average (min 1-5) | ANOVA | Drug | 0.129 | 2,10 | 0.8804 | — | 9K |

TABLE 1-10

Statistical analysis

| Cohort/ Behavioral Paradigm | Measurement | Statistical Test | Comparison | F | ° of freedom | p | * | FIG. |
|---|---|---|---|---|---|---|---|---|
| Ovariectomized, 1 week prophylactic drug/ Contextual Fear Conditioning Training | Freezing (min 1-5) | RMANOVA | Surgery | 2.482 | 1,308 | 0.1193 | — | 10A |
| | | | Drug | 1.164 | 2,308 | 0.3175 | — | |
| | | | Time | 172.273 | 4,308 | <0.0001 | *** | |
| | | | Surgery x Time | 1.581 | 4,308 | 0.1791 | — | |
| | | | Drug x Time | 1.522 | 8,308 | 0.1488 | — | |
| | | | Surgery x Drug x Time | 1.514 | 8,308 | 0.1515 | — | |
| Ovariectomized, 1 week prophylactic drug/ Contextual Fear Conditioning Re-exposure | Freezing (min 1-5) | RMANOVA | Surgery | 0.002 | 1,308 | 0.9667 | — | 10B |
| | | | Drug | 4.751 | 2,308 | 0.0113 | * | |
| | | | Time | 21.391 | 4,308 | <0.0001 | *** | |
| | | | Surgery x Time | 2.126 | 4,308 | 0.0775 | — | |
| | | | Drug x Time | 0.488 | 8,308 | 0.8647 | — | |
| | | | Surgery x Drug x Time | 0.640 | 8,308 | 0.7437 | — | |
| | | Fisher's PLSD | Sham Sal vs. Sham K (10) | — | — | 0.0290 | * | |
| | | | Sham Sal vs. Sham (2R,6R)-HNK (0.025) | — | — | 0.0244 | * | |
| | | | OVX Sal vs. OVX K (10) | — | — | 0.1532 | — | |
| | | | OVX Sal vs. OVX (2R,6R)-HNK (0.025) | — | — | 0.2290 | — | |
| | | | Sham Sal vs. OVX Sal | — | — | 0.4289 | — | |
| | | | Sham K (10) vs. OVX K (10) | — | — | 0.7813 | — | |
| | | | Sham (2R,6R)-HNK (0.025) vs. OVX (2R,6R)-HNK (0.025 | — | — | 0.3764 | — | |
| | Freezing Average (min 1-5) | ANOVA | Surgery | 0.002 | 2,77 | 0.9667 | — | 10C |
| | | | Drug | 4.751 | 1,77 | 0.0113 | * | |
| | | | Surgery x Drug | 0.649 | 2,77 | 0.5252 | — | |
| | | Fisher's PLSD | Sham Sal vs. Sham K (10) | — | — | 0.0290 | * | |
| | | | Sham Sal vs. Sham (2R,6R)-HNK (0.025) | — | — | 0.0244 | * | |
| | | | OVX Sal vs. OVX K (10) | — | — | 0.1532 | — | |
| | | | OVX Sal vs. OVX (2R,6R)-HNK (0.025) | — | — | 0.2290 | — | |
| | | | Sham Sal vs. OVX Sal | — | — | 0.4289 | — | |
| | | | Sham K (10) vs. OVX K (10) | — | — | 0.7813 | — | |
| | | | Sham (2R,6R)-HNK (0.025) vs. OVX (2R,6R)-HNK (0.025 | — | — | 0.3764 | — | |

TABLE 1-10-continued

Statistical analysis

| Cohort/ Behavioral Paradigm | Measurement | Statistical Test | Comparison | F | ° of freedom | p | * | FIG. |
|---|---|---|---|---|---|---|---|---|
| Ovariectomized, 1 week prophylactic drug/Forced Swim Test Day 1 | Immobility Time (min 1-6) | RMANOVA | Surgery | 2.727 | 1,385 | 0.1028 | — | |
| | | | Drug | 0.795 | 2,385 | 0.4554 | — | |
| | | | Time | 113.921 | 5,385 | <0.0001 | *** | |
| | | | Surgery x Time | 4.092 | 5,385 | 0.0012 | ** | |
| | | | Drug x Time | 1.330 | 10,385 | 0.2122 | — | |
| | | | Surgery x Drug x Time | 1.073 | 10,385 | 0.3823 | — | |
| | | | Sham Sal vs. Sham K (10) | — | — | 0.0140 | * | |
| | | | Sham Sal vs. Sham (2R,6R)-HNK (0.025) | — | — | 0.7085 | — | |
| | | | OVX Sal vs. OVX K (10) | — | — | 0.0920 | — | |
| | | | OVX Sal vs. OVX (2R,6R)-HNK (0.025) | — | — | 0.2525 | — | |
| | | | Sham Sal vs. OVX Sal | — | — | 0.0765 | — | |
| | | | Sham K (10) vs. OVX K (10) | — | — | 0.0533 | — | |
| | | | Sham (2R,6R)-HNK (0.025) vs. OVX (2R,6R)-HNK (0.025 | — | — | <0.0001 | *** | |
| | Immobility Time Average (min 3-6) | ANOVA | Surgery | 0.853 | 1,77 | 0.3586 | — | |
| | | | Drug | 0.468 | 2,77 | 0.6277 | — | |
| | | | Surgery x Drug | 9.029 | 2,77 | 0.0003 | ** | |
| | | Fisher's PLSD | Sham Sal vs. Sham K (10) | — | — | 0.0114 | * | |
| | | | Sham Sal vs. Sham (2R,6R)-HNK (0.025) | — | — | 0.9957 | — | |
| | | | OVX Sal vs. OVX K (10) | — | — | 0.0570 | — | |
| | | | OVX Sal vs. OVX (2R,6R)-HNK (0.025) | — | — | 0.3199 | — | |
| | | | Sham Sal vs. OVX Sal | — | — | 0.1094 | — | |
| | | | Sham K (10) vs. OVX K (10) | — | — | 0.0233 | * | |
| | | | Sham (2R,6R)-HNK (0.025) vs. OVX (2R,6R)-HNK (0.025) | — | — | 0.0001 | *** | |
| Ovariectomized, E2/P4 replacement, 1 week prophylactic drug/ Contextual Fear Conditioning Training | Freezing (min 1-5) | RMANOVA | Hormone | 25.922 | 1,244 | <0.0001 | *** | 10D |
| | | | Drug | 0.051 | 2,244 | 0.9505 | — | |
| | | | Time | 205.080 | 4,244 | <0.0001 | *** | |
| | | | Hormone x Time | 17.439 | 4,244 | <0.0001 | *** | |
| | | | Drug x Time | 0.665 | 8,244 | 0.7218 | — | |
| | | | Hormone x Drug x Time | 0.454 | 8,244 | 0.8872 | — | |
| | | Fisher's PLSD | Vehicle Sal vs. Vehicle K (10) | — | — | 0.1466 | — | |
| | | | Vehicle Sal vs. Vehicle (2R,6R)-HNK (0.025) | — | — | 0.6290 | — | |
| | | | E2/P4 Sal vs. E2/P4 K (10) | — | — | 0.5725 | — | |
| | | | E2/P4 Sal vs. E2/P4 (2R,6R)-HNK (0.025) | — | — | 0.7901 | — | |
| | | | Vehicle Sal vs. E2/P4 Sal | — | — | 0.0731 | — | |
| | | | Vehicle K (10) vs. E2/P4 K (10) | — | — | 0.0004 | ** | |
| | | | Vehicle (2R,6R)-HNK (0.025) vs. E2/P4 (2R,6R)-HNK (0.025) | — | — | 0.0067 | ** | |
| Ovariectomized, E2/P4 replacement, 1 week prophylactic drug/ Contextual Fear Conditioning Re-exposure | Freezing (min 1-5) | RMANOVA | Hormone | 0.762 | 1,244 | 0.3861 | — | 10E |
| | | | Drug | 3.642 | 2,244 | 0.0321 | * | |
| | | | Time | 1.045 | 2,244 | 0.3579 | — | |
| | | | Hormone x Time | 1.028 | 4,244 | 0.3934 | — | |
| | | | Drug x Time | 0.876 | 8,244 | 0.5369 | — | |
| | | | Hormone x Drug x Time | 1.151 | 8,244 | 0.3297 | — | |
| | | Fisher's PLSD | Vehicle Sal vs. Vehicle K (10) | — | — | 0.0077 | ** | |
| | | | Vehicle Sal vs. Vehicle (2R,6R)-HNK (0.025) | — | — | 0.9324 | — | |
| | | | E2/P4 Sal vs. E2/P4 K (10) | — | — | 0.7946 | — | |
| | | | E2/P4 Sal vs. E2/P4 (2R,6R)-HNK (0.025) | — | — | 0.4219 | — | |
| | | | Vehicle Sal vs. E2/P4 Sal | — | — | 0.6088 | — | |
| | | | Vehicle K (10) vs. E2/P4 K (10) | — | — | 0.2095 | — | |
| | | | Vehicle (2R,6R)-HNK (0.025) vs. E2/P4 (2R,6R)-HNK (0.025) | — | — | 0.5588 | — | |
| | Freezing Average (min 1-5) | ANOVA | Hormone | 0.762 | 1,61 | 0.3861 | — | 10F |
| | | | Drug | 3.642 | 2,61 | 0.0321 | * | |
| | | | Hormone x Drug | 1.045 | 2,61 | 0.3579 | — | |
| | | Fisher's PLSD | Vehicle Sal vs. Vehicle K (10) | — | — | 0.0077 | ** | |
| | | | Vehicle Sal vs. Vehicle (2R,6R)-HNK (0.025) | — | — | 0.9324 | — | |
| | | | E2/P4 Sal vs. E2/P4 K (10) | — | — | 0.7946 | — | |
| | | | E2/P4 Sal vs. E2/P4 (2R,6R)-HNK (0.025) | — | — | 0.4219 | — | |

TABLE 1-10-continued

Statistical analysis

| Cohort/ Behavioral Paradigm | Measurement | Statistical Test | Comparison | F | ° of freedom | p | * | FIG. |
|---|---|---|---|---|---|---|---|---|
| | | | Vehicle Sal vs. E2/P4 Sal | — | — | 0.6088 | — | |
| | | | Vehicle K (10) vs. E2/P4 K (10) | — | — | 0.2095 | — | |
| | | | Vehicle (2R,6R)-HNK (0.025) vs. E2/P4 (2R,6R)-HNK (0.025) | — | — | 0.5588 | — | |
| Ovariectomized, E2/P4 replacement, 1 week prophylactic drug/Forced Swim Test Day 1 | Immobility Time (min 1-6) | RMANOVA | Hormone | 0.471 | 1,300 | 0.4953 | — | |
| | | | Drug | 2.243 | 2,300 | 0.1150 | — | |
| | | | Time | 51.009 | 5,300 | <0.0001 | *** | |
| | | | Hormone x Time | 0.531 | 5,300 | 0.7531 | — | |
| | | | Drug x Time | 0.958 | 10,300 | 0.4803 | — | |
| | | | Hormone x Drug x Time | 0.784 | 10,300 | 0.6441 | — | |
| | Immobility Time Average (min 3-6) | ANOVA | Hormone | 0.104 | 1,60 | 0.7476 | — | |
| | | | Drug | 2.450 | 2,60 | 0.0949 | — | |
| | | | Hormone x Drug | 0.787 | 2,60 | 0.4598 | — | |

TABLE 2

List of experimental n

| Figure | Drug | Dose (mg/kg) | Stress/Treatment | n |
|---|---|---|---|---|
| 1 | Saline | | CFC | 21 |
| | (R,S)-ketamine | 2.5 | CFC | 9 |
| | | 10 | CFC | 21 |
| | | 30 | CFC | 22 |
| | (2R,6R)-HNK | 0.025 | CFC | 10 |
| | | 0.075 | CFC | 9 |
| | | 0.1 | CFC | 10 |
| | | 0.3 | CFC | 8 |
| | | 2.5 | CFC | 8 |
| | | 10 | CFC | 8 |
| | (2S,6S)-HNK | 0.025 | CFC | 8 |
| | | 0.075 | CFC | 10 |
| | | 0.1 | CFC | 8 |
| | | 0.3 | CFC | 9 |
| | | 2.5 | CFC | 8 |
| | | 10 | CFC | 8 |
| 2A-2C | Saline | | CFC/3-day | 5 |
| | (R,S)-ketamine | 2.5 | CFC/3-day | 5 |
| | | 10 | CFC/3-day | 5 |
| | | 30 | CFC/3-day | 5 |
| | (2R,6R)-HNK | 0.025 | CFC/3-day | 10 |
| 2D-2E | Saline | | CFC/24-hr | 9 |
| | (2R,6R)-HNK | 0.025 | CFC/24-hr | 10 |
| 3 | Saline | | CIS | 10 |
| | (R,S)-ketamine | 10 | CIS | 9 |
| | (2R,6R)-HNK | 0.025 | CIS | 10 |
| 4 | Saline | | LH | 9 |
| | (R,S')-ketamine | 10 | LH | 10 |
| | (2R,6R)-HNK | 0.025 | LH | 10 |
| 5A-5C | Saline | | CFC/Sham | 13 |
| | (R,S)-ketamine | 10 | CFC/Sham | 10 |
| | (2R,6R)-HNK | 0.025 | CFC/Sham | 13 |
| | Saline | | CFC/OVX | 15 |
| | (R,S)-ketamine | 10 | CFC/OVX | 14 |
| | (2R,6R)-HNK | 0.025 | CFC/OVX | 15 |
| 5D-5F | Saline | | CFC/Vehicle | 14 |
| | (R,S)-ketamine | 10 | CFC/Vehicle | 9 |
| | (2R,6R)-HNK | 0.025 | CFC/Vehicle | 10 |
| | Saline | | CFC/E2-P4 | 7 |
| | (R,S)-ketamine | 10 | CFC/E2-P4 | 11 |
| | (2R,6R)-HNK | 0.025 | CFC/E2-P4 | 15 |
| 6A-6F | Saline | | CFC | 21 |
| | (R,S)-ketamine | 2.5 | CFC | 9 |
| | | 10 | CFC | 21 |
| | | 30 | CFC | 22 |
| | (2R,6R)-HNK | 0.025 | CFC | 10 |
| | | 0.075 | CFC | 9 |
| | | 0.1 | CFC | 10 |
| | | 0.3 | CFC | 8 |
| | | 2.5 | CFC | 8 |
| | | 10 | CFC | 8 |
| | (2S,6S)-HNK | 0.025 | CFC | 8 |
| | | 0.075 | CFC | 10 |
| | | 0.1 | CFC | 8 |
| | | 0.3 | CFC | 9 |
| | | 2.5 | CFC | 8 |
| | | 10 | CFC | 8 |
| 7A-7C | Saline | | CFC/3-day | 5 |
| | (R,S)-ketamine | 2.5 | CFC/3-day | 5 |
| | | 10 | CFC/3-day | 5 |
| | | 30 | CFC/3-day | 5 |
| | (2R,6R)-HNK | 0.025 | CFC/3-day | 10 |
| 7D-7F | Saline | | CFC/24-hr | 9 |
| | (2R,6R)-HNK | 0.025 | CFC/24-hr | 10 |
| 8A-8I | Saline | | LH | 9 |
| | (R,S)-ketamine | 10 | LH | 10 |
| | (2R,6R)-HNK | 0.025 | LH | 10 |
| 9A-9K | Saline | | Antidepressant | 5 |
| | (R,S)-ketamine | 10 | Antidepressant | 5 |
| | (2R,6R)-HNK | 0.025 | Antidepressant | 5 |
| 10A-10C | Saline | | CFC/Sham | 13 |
| | (R,S)-ketamine | 10 | CFC/Sham | 10 |
| | (2R,6R)-HNK | 0.025 | CFC/Sham | 13 |
| | Saline | | CFC/OVX | 15 |
| | (R,S)-ketamine | 10 | CFC/OVX | 14 |
| | (2R,6R)-HNK | 0.025 | CFC/OVX | 15 |
| 10D-10F | Saline | | CFC/Vehicle | 14 |
| | (R,S)-ketamine | 10 | CFC/Vehicle | 9 |
| | (2R,6R)-HNK | 0.025 | CFC/Vehicle | 10 |
| | Saline | | CFC/E2-P4 | 7 |
| | (R,S)-ketamine | 10 | CFC/E2-P4 | 11 |
| | (2R,6R)-HNK | 0.025 | CFC/E2-P4 | 15 |

TABLE 3

Summary of behavioral experiments

| Drug | Dose (mg/kg) | Stress Model | Time Interval | Sex | Learned Fear | Depressive-Like Behavior | Anxiety-Like Behavior |
|---|---|---|---|---|---|---|---|
| (R,S)-ketamine | 10 | Contextual Fear Conditioning | 1 week | F | — | ↓ | — |
| | 10 | | 3 days | F | — | — | — |
| | 10 | Chronic Immobilization Stress | 1 week | F | — | ↓ | — |
| | 10 | Learned Helplessness | 1 week | F | — | ↓ | ↓ |
| (2R,6R)-HNK | 0.025 | Contextual Fear Conditioning | 1 week | F | — | ↓ | — |
| | 0.025 | | 3 days | F | — | ↓ | — |
| | 0.025 | | 24 hours | F | — | — | — |
| | 0.025 | Chronic Immobilization Stress | 1 week | F | — | ↓ | — |
| | 0.025 | Learned Helplessness | 1 week | F | — | ↓ | — |

What is claimed is:

1. A method for inducing and/or enhancing stress resilience in a female subject, comprising administering a pharmaceutic composition to the female subject prior to a stressor, wherein the pharmaceutic composition comprises an effective amount of an agent selected from the group consisting of (R)-ketamine, (S)-ketamine, (R,S)-ketamine, hydroxyketamines, dehydronorketamine, (R,S)-norketamine, (2R,6R)-hydroxynorketamine ((2R,6R)-HNK), and (2S,6S)-hydroxynorketamine, (2R,6R;2S,6S)-HNK, and a pharmaceutically acceptable salt thereof, wherein the effective amount of the agent administered to the female subject is no greater than 70% of an effective amount of the agent administered to a male subject.

2. The method of claim 1, wherein the agent is (R,S)-ketamine.

3. The method of claim 1, wherein the agent is (2R,6R)-hydroxynorketamine ((2R,6R)-HNK).

4. The method of claim 1, wherein the effective amount of the agent administered to the female subject is no greater than 60% of the effective amount administered to a male subject.

5. The method of claim 1, wherein the effective amount of the agent administered to the female subject is no greater than 50% of the effective amount administered to a male subject.

6. The method of claim 1, wherein the pharmaceutic composition is administered to the female subject about 48 hours to about 3 weeks prior to a stressor.

7. The method of claim 1, wherein the pharmaceutic composition is administered to the female subject about 72 hours to about 2 weeks prior to a stressor.

8. The method of claim 1, wherein the pharmaceutic composition is administered to the female subject about 1 week prior to a stressor.

9. The method of claim 1, wherein the pharmaceutic composition is administered to the female subject about 3 days prior to a stressor.

10. The method of claim 1, wherein the pharmaceutic composition is administered to the subject once prior to a stressor.

11. The method of claim 1, wherein the pharmaceutic composition is administered orally, intravenously, intranasally, or via injection to the subject.

12. The method of claim 1, further comprising preventing or delaying stress-induced cognitive impairment and/or decline.

13. The method of claim 1, further comprising administering an effective amount of an anti-depressant, an anxiolytic, or combinations thereof.

14. The method of claim 1, further comprising administering an effective amount of a selective serotonin reuptake inhibitor (SSRI), or a pharmaceutically acceptable salt or derivative thereof.

15. The method of claim 1, further comprising administering an effective amount of fluoxetine, paroxetine, sertraline, lithium, riluzole, prazosin, lamotrigine, ifenprodil, or combinations thereof.

16. The method of claim 1, wherein the subject is a mammal.

17. The method of claim 1, wherein the subject is a human.

18. The method of claim 1, wherein the pharmaceutical composition is administered in a booster series.

19. The method of claim 1, wherein the agent is hydroxyketamine.

20. The method of claim 1, wherein the agent is dehydronorketamine.

* * * * *